(12) United States Patent
Lee et al.

(10) Patent No.: US 11,466,285 B2
(45) Date of Patent: Oct. 11, 2022

(54) PLANTS COMPRISING HERBICIDE-RESISTANT EVENT SEQUENCES, PLANT MATERIALS, AND METHODS FOR DETECTION THEREOF

(71) Applicant: OMS Investments, Inc., Los Angeles, CA (US)

(72) Inventors: Lisa Lee, Marysville, OH (US); Rebecca S. Torisky, Marysville, OH (US); Samuel L. Freshour, Marysville, OH (US); Matthew J. Koch, Dublin, OH (US); Robert W. Harriman, Delaware, OH (US)

(73) Assignee: OMS INVESTMENTS, INC., Los Angeles, CA (US)

( * ) Notice: Subject to any disclaimer, the term of this patent is extended or adjusted under 35 U.S.C. 154(b) by 326 days.

(21) Appl. No.: 16/193,135

(22) Filed: Nov. 16, 2018

(65) Prior Publication Data

US 2019/0276838 A1    Sep. 12, 2019

Related U.S. Application Data

(60) Provisional application No. 62/588,000, filed on Nov. 17, 2017.

(51) Int. Cl.
| | | |
|---|---|---|
| *C12N 15/82* | (2006.01) |
| *A01H 6/46* | (2018.01) |
| *C12Q 1/6895* | (2018.01) |
| *C12N 1/10* | (2006.01) |
| *C12N 9/10* | (2006.01) |

(52) U.S. Cl.
CPC ............ *C12N 15/8275* (2013.01); *A01H 6/46* (2018.05); *C12N 9/1092* (2013.01); *C12N 15/825* (2013.01); *C12N 15/8262* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2015/0020233 A1*  1/2015  Harriman ............. C12N 9/0071
                                                           800/260
2016/0194656 A1*  7/2016  Harriman et al. ..........................
                                                           C12Y 114/11013
                                                           800/266

OTHER PUBLICATIONS

Latham et al. (2006) J Biomed Biotechnol 2006:25376.*

* cited by examiner

*Primary Examiner* — Russell T Boggs
(74) *Attorney, Agent, or Firm* — ArentFox Schiff LLP

(57) ABSTRACT

The invention provides glyphosate-tolerant transgenic turfgrass plants, plant material, and propagules that have a specific transformation event. Also provided are assays for detecting the presence of the event.

19 Claims, 8 Drawing Sheets

Specification includes a Sequence Listing.

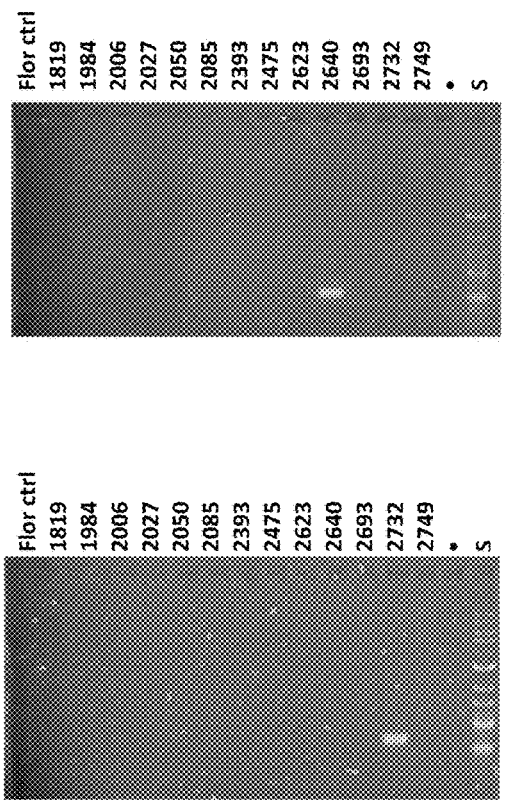
FIG. 6M
FIG. 6O
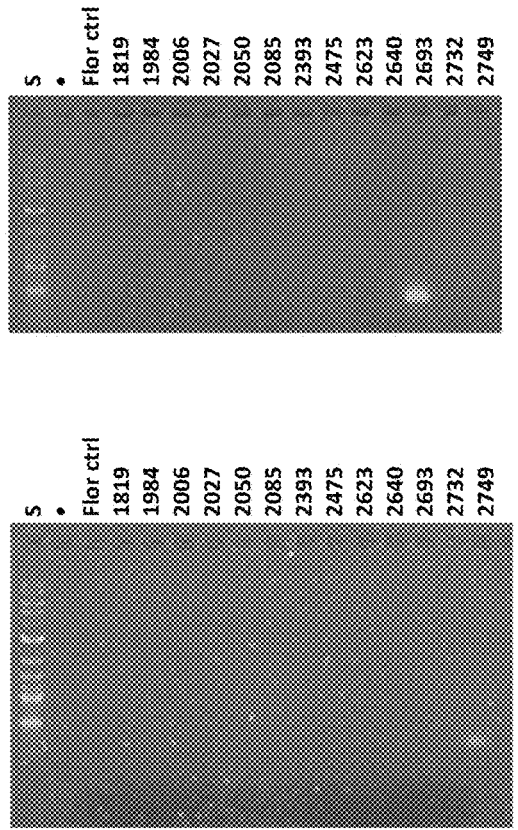
FIG. 6N
FIG. 6P

SEQUENCE LISTING

```
<160> NUMBER OF SEQ ID NOS: 55

<210> SEQ ID NO 1
<211> LENGTH: 1114
<212> TYPE: DNA
<213> ORGANISM: Artificial Sequence
<220> FEATURE:
<223> OTHER INFORMATION: Chromosomal flanking sequence from St.
      Augustinegrass event Ss026-1819
<220> FEATURE:
<221> NAME/KEY: primer_bind
<222> LOCATION: (1)..(28)
<223> OTHER INFORMATION: binding site for primer 1819 ZS Sn 1 3-1
<220> FEATURE:
<221> NAME/KEY: misc_feature
<222> LOCATION: (1)..(250)
<223> OTHER INFORMATION: genomic DNA
<220> FEATURE:
<221> NAME/KEY: misc_feature
<222> LOCATION: (251)..(1114)
<223> OTHER INFORMATION: transgene DNA
<220> FEATURE:
<221> NAME/KEY: primer_bind
<222> LOCATION: (1082)..(1114)
<223> OTHER INFORMATION: binding site for primer Sp3rev

<400> SEQUENCE: 1
ggtcctttat agggaaagca tatcatagag aattctaatt ctcatatatc atatagggta       60
ggttgtggta tttcattgct acaaacatgt cttatttttac aataagacat gtcatttgga     120
tacttctctt caacttcgaa gtattttgat acaaatagtt atagttgaag ttaattttac      180
gaaagaaaat aaggcggatt atgggagtgt gtgacttgaa ttattaattc ggccatgcag      240
atagagaatt gggctccccg accccgaact gcctctccca gctctcctgg tccgaggcct      300
tccacatccc gatgaacgac atctgctcca acgcccgag gaacattgcc aacggtaacc       360
cgaacatctc caacctctgc tccaccgtga gcagttcgc caccaccgtg tccgagctgg      420
ccaacaagct cgccaacatc ctcgtcgaga agctcggcca tgacgagctg accttcatcg     480
aggagaagtg ctccccgaac acgtgctacc tcaggatgaa ccgctacccg ccgtgcccaa    540
```

```
agtactccca cgtgctcggc ctcatgccac ataccgactc cgacttcctc accatcctct    600
accaggacca ggtgggcggc ctccagctcg tgaaggacgg ccgctggatt tccgtgaagc    660
cgaacccaga ggccctcatc gtgaacatcg gcgacctctt ccaggcctgg tctaacggcg    720
tgtacaagtc cgtggtgcat agggtggtgg ccaacccgag gttcgagagg ttctctaccg    780
cctacttcct ctgcccgtcc ggcgacgccg tgatccagtc ctaccgcgag ccgtctatgt    840
accgcaagtt cagcttcggc gagtacaggc agcaggtcca gcaggacgtg cgcgagttcg    900
gccacaagat cggcctctcc cgcttcctca tctgcaacga gctcgaattc gcatggcgtg    960
ggataataca gactgtatat aggaggaata atggtttgct gcttgtagct ctgtaaatag   1020
gaaaatgaag ctcagctttt actttcagtc atctagttcg gtagtgtagg ccgggtttgc   1080
tgaagtttgg ttaatgaagg ctctgtgtct ctgc                              1114
```

<210> SEQ ID NO 2
<211> LENGTH: 230
<212> TYPE: DNA
<213> ORGANISM: Artificial Sequence
<220> FEATURE:
<223> OTHER INFORMATION: Chromosomal flanking sequence from St.
      Augustinegrass event Ss026-1984
<220> FEATURE:
<221> NAME/KEY: primer_bind
<222> LOCATION: (1)..(24)
<223> OTHER INFORMATION: binding site for primer 1984 RU FNS 1 3-2
<220> FEATURE:
<221> NAME/KEY: misc_feature
<222> LOCATION: (1)..(101)
<223> OTHER INFORMATION: genomic DNA
<220> FEATURE:
<221> NAME/KEY: misc_feature
<222> LOCATION: (102)..(230)
<223> OTHER INFORMATION: transgene DNA
<220> FEATURE:
<221> NAME/KEY: primer_bind
<222> LOCATION: (205)..(230)
<223> OTHER INFORMATION: Binding site for primer PRU 761 f1-1

<400> SEQUENCE: 2

```
tggctggaca gggatttcgt gactgggttc cacgagggga agaagaaaag aagaaaggaa     60
gcacagaaga tgttgcagga gaaggagggg aagaacagaa tcgtggtacc gcggccgcaa    120
gcttgtcgac ctgatgatta ttttgttgat catgattttc ttttggctat ttgattttttt   180 gaaagatatt ttttcccctg ggaagacacc tatgggacga agatattatg                230
```

<210> SEQ ID NO 3
<211> LENGTH: 669
<212> TYPE: DNA
<213> ORGANISM: Artificial Sequence
<220> FEATURE:
<223> OTHER INFORMATION: Chromosomal flanking sequence from St.
      Augustinegrass event Ss026-2006
<220> FEATURE:
<221> NAME/KEY: primer_bind
<222> LOCATION: (1)..(31)
<223> OTHER INFORMATION: Binding site for primer 2006 TAIL GO 1 3-1
<220> FEATURE:
<221> NAME/KEY: misc_feature
<222> LOCATION: (1)..(535)
<223> OTHER INFORMATION: genomic DNA
<220> FEATURE:
<221> NAME/KEY: misc_feature
<222> LOCATION: (537)..(669)
<223> OTHER INFORMATION: transgene DNA
<220> FEATURE:
<221> NAME/KEY: primer_bind
<222> LOCATION: (636)..(669)
<223> OTHER INFORMATION: Binding site for primer PGO 761 f1-1

<400> SEQUENCE: 3

```
atccacatgt gcatctcgtt atggcctggg tgcctggcca ttcttttgtt gcattgcatt      60
gccacctacc gtgcgtgctt atattagtta gagtaagttg attaaactac ttagctcgtc     120
aaataatgcg cgtctgagcg ccgcttgcca ggagaattaa gtatgtgtca atgggcaaca     180
atcaacgaga ggtgggacat gctgttcggt cttgtgtcct gatccgcccg tttgtattgt     240
ttgtttatat gcagttaatt atgcggtctc gagagcgagt attgtaatcg caagaggttg     300
cagccagcac taccgccgat atcttgttag aggtcgcagt aacctgctgg taggagtagg     360
actgtaggag taacatggta agtggactcc tcatcttgtt gtatccggcg tcctgtacag     420
tgtacagtac agcttgggca aaggcccaaa gagattccgt cgtggcgatg gcgatccgga     480
tccatcgagc gcacgacact tgacaggtcg caccttgcag gcccgtcaat aatttgtacc     540
gcggccgcaa gctttctaga atccgaaaag tttctgcacc gttttcaccc cctaactaac     600
aatataggga acgtgtgcta aatataaaat gagaccttat atatgtagcg ctgataacta     660
gaactatgc                                                             669
```

<210> SEQ ID NO 4
<211> LENGTH: 482
<212> TYPE: DNA
<213> ORGANISM: Artificial Sequence
<220> FEATURE:
<223> OTHER INFORMATION: Chromosomal flanking sequence from St.
Augustinegrass event Ss026-2027
<220> FEATURE:
<221> NAME/KEY: primer_bind
<222> LOCATION: (1)..(29)
<223> OTHER INFORMATION: Binding site for primer 2027 ZS2 3-1
<220> FEATURE:
<221> NAME/KEY: misc_feature
<222> LOCATION: (1)..(34)
<223> OTHER INFORMATION: genomic DNA
<220> FEATURE:
<221> NAME/KEY: misc_feature
<222> LOCATION: (35)..(482)
<223> OTHER INFORMATION: transgene DNA
<220> FEATURE:
<221> NAME/KEY: primer_bind
<222> LOCATION: (450)..(482)
<223> OTHER INFORMATION: Binding site for primer Sp3 rev

<400> SEQUENCE: 4

```
cttaggtgga aggcgaagaa ggcccccttc cgggcagagg ccctcatcga gaacatccgc      60
gacctcttcc aggcctggtc taacggcgtg tacaagtccg tggtgcatag ggtggtggcc     120
aacccgaggt tcgagaggtt ctctaccgcc tacttcctct gcccgtccgg cgacgccgtg     180
atccagtcct accgcgagcc gtctatgtac cgcaagttca gcttcggcga gtacaggcag     240
caggtccagc aggacgtgcg cgagttcggc cacaagatcg gcctctcccg cttcctcatc     300
tgcaacgagc tcgaattcgc atggcgtggg ataatacaga ctgtatatag gaggaataat     360
ggtttgctgc ttgtagctct gtaaatagga aaatgaagct cagcttttac tttcagtcat     420
ctagttcggt agtgtaggtc gggtttgctg aagtttggtt aatgaaggct ctgtgtctct     480
gc                                                                   482
```

<210> SEQ ID NO 5
<211> LENGTH: 790
<212> TYPE: DNA
<213> ORGANISM: Artificial Sequence
<220> FEATURE:
<223> OTHER INFORMATION: Chromosomal flanking sequence from St.

Augustinegrass event Ss026-2050
<220> FEATURE:
<221> NAME/KEY: primer_bind
<222> LOCATION: (1)..(31)
<223> OTHER INFORMATION: Binding site for primer 2050 TAIL GO 1 3-3
<220> FEATURE:
<221> NAME/KEY: misc_feature
<222> LOCATION: (1)..(696)
<223> OTHER INFORMATION: genomic DNA
<220> FEATURE:
<221> NAME/KEY: misc_feature
<222> LOCATION: (697)..(790)
<223> OTHER INFORMATION: transgene DNA
<220> FEATURE:
<221> NAME/KEY: primer_bind
<222> LOCATION: (756)..(790)
<223> OTHER INFORMATION: Binding site for primer PGO 761 fl-1

<400> SEQUENCE: 5
gttgacgtgc gtacgaacaa acgagtttca gcaacggccg tcggtgcttc gtgcgtgctc      60
ttgtccatct ctgtctgtca ctcatctata atttaattaa tttgctgcac acaatttaat     120
tatatatcac ttttaccaac ggctaaccac ctgcatgagt acgtgtcttt gtttgtggct     180
gcactctcct gtggggaaga ttactagaag gatcctgctg ctgctagtat catatcatat     240
atcgacgatg gacggacgga tacgatgttt aattgcctga taagcactca catccaaccc     300
ccaaaccctc gctgacactg aatggattga attcggcctc caaatccagc tgctgcaaat     360
cagtcctgtt aggcggccgc tgctaattct tcaatactac tccaatactc ctacggtact     420
gtgtacaatt caattcaatt caccctgctg ctgctgcctc aactacgagc atagcatgca     480
tcatctagcc tgctgccggc ccaactccca actacctgca gccggtctct taattcccat     540
tccatcgagg ccgacaccaa cgacagggat ccaccgacga ccgaaactgc tggacaccat     600
gcccatggcc atgcatgcac ccatcatcag ctagcacctc cgatcccag gccatctcag      660 ctccgtcctc gtcagtcatc gctcgtcaca aaccacgcac cgttttcacc ccctaactaa     720
caatataggg aacgtgtgct aaatataaaa tgagacctta tatatgtagc gctgataact     780
agaactatgc                                                             790

<210> SEQ ID NO 6
<211> LENGTH: 678
<212> TYPE: DNA
<213> ORGANISM: Artificial Sequence
<220> FEATURE:
<223> OTHER INFORMATION: Chromosomal flanking sequence from St.
      Augustinegrass event Ss026-2085
<220> FEATURE:
<221> NAME/KEY: primer_bind
<222> LOCATION: (1)..(29)
<223> OTHER INFORMATION: Binding site for primer 2085 GO Sn 1 3-2
<220> FEATURE:
<221> NAME/KEY: misc_feature
<222> LOCATION: (1)..(604)
<223> OTHER INFORMATION: genomic DNA
<220> FEATURE:
<221> NAME/KEY: misc_feature
<222> LOCATION: (605)..(678)
<223> OTHER INFORMATION: transgene DNA
<220> FEATURE:
<221> NAME/KEY: primer_bind
<222> LOCATION: (644)..(678)
<223> OTHER INFORMATION: Binding site for primer PGO 761 fl-1

<400> SEQUENCE: 6
gagccgactc atgcctaatg cttctctaga ttcgaaacat tgatctcaat gtgatatctt      60
tataacttga tattttgact atagaccctt caatgaaaaa gctcaacctc cagagggtgt     120

| | |
|---|---|
| agtaccaggc atcaaacatg gactggcaag ggagcttttg agctcactgc tctgaccagt | 180 |
| ataatgcgtg caaagatggt agctctttag tgaactcttt gttatatgaa acaaccaata | 240 |
| cttgcttggt agtagacctg atcattttt gggtcgtgcc gagccgaaaa aagcctagtt | 300 |
| gattttggac caaagattcg ttcttgcggc tgtcccacgg gctttgtcga ctgggctctt | 360 |
| ttttagttga aaataaatca aataaattgt ctgggcagac tcgaaccaac ctgatttttt | 420 |
| ttgggcttgg ttttcgctaa acgcacccaa tcctataggc atcatgagtg gccaaatcc | 480 |
| tagtggactt gaaggcccat gggctgggcg ggctgggcca aaaaattctc aggtatactt | 540 |
| ggtagccatc tctcctgaag ttgtcgtatt tccgaaaagt ttctgcaccg ttttcacccc | 600 |
| ctaactaaca atatagggaa cgtgtgctaa atataaaatg agaccttata tatgtagcgc | 660 |
| tgataactag aactatgc | 678 |

```
<210> SEQ ID NO 7
<211> LENGTH: 358
<212> TYPE: DNA
<213> ORGANISM: Artificial Sequence
<220> FEATURE:
<223> OTHER INFORMATION: Chromosomal flanking sequence from St.
      Augustinegrass event Ss026-2085
<220> FEATURE:
<221> NAME/KEY: primer_bind
<222> LOCATION: (1)..(25)
<223> OTHER INFORMATION: Binding site for Primer 2085 SZ Sn 1 3-2
<220> FEATURE:
<221> NAME/KEY: misc_feature
<222> LOCATION: (1)..(182)
<223> OTHER INFORMATION: genomic DNA
<220> FEATURE:
<221> NAME/KEY: misc_feature
<222> LOCATION: (183)..(358)
<223> OTHER INFORMATION: transgene DNA
<220> FEATURE:
<221> NAME/KEY: primer_bind
<222> LOCATION: (329)..(358)
<223> OTHER INFORMATION: Binding sigte for Primer 2085 SZ Sn 1 5-1

<400> SEQUENCE: 7
```

| | |
|---|---|
| tattacagcg ccttctaata atgtcagtaa gccaaccacc cgggtggaca tatgagcatc | 60 |
| ccagaaatgg tgtaaactgt taacttacaa aggcatacct tcgtactttt tagggaaaa | 120 |
| agactctacg ctctgctgtt cttttgagcc caactagcg tgaactcaag ctgactgagt | 180 |
| ccgcaacgcc aacatctccg acccaccgtt cgaggagacc tacaagaacc tcctgctcaa | 240 |
| gcacaacatc acccccgctca ccaccaccac gaccacgacg accaccacgg cgaccatcga | 300 |
| ggtgagggat ctcccactca tcgacctctc caggctcgtg ccaccgccg ccaaggag | 358 |

```
<210> SEQ ID NO 8
<211> LENGTH: 551
<212> TYPE: DNA
<213> ORGANISM: Artificial Sequence
<220> FEATURE:
<223> OTHER INFORMATION: Chromosomal flanking sequence from St.
      Augustinegrass event Ss026-2393
<220> FEATURE:
<221> NAME/KEY: primer_bind
<222> LOCATION: (1)..(28)
<223> OTHER INFORMATION: Binding site for Primer 2393 GO Sn 1 3-2
<220> FEATURE:
<221> NAME/KEY: misc_feature
<222> LOCATION: (1)..(415)
<223> OTHER INFORMATION: genomic DNA
<220> FEATURE:
<221> NAME/KEY: misc_feature
<222> LOCATION: (416)..(551)
<223> OTHER INFORMATION: transgene DNA
```

-continued

```
<220> FEATURE:
<221> NAME/KEY: primer_bind
<222> LOCATION: (517)..(551)
<223> OTHER INFORMATION: Binding site for Primer PGO 761 fl-1

<400> SEQUENCE: 8
cggtgcgcct tcgcccactt tcggttagtt cggttggttt atcaaccacc ggtcaatagt      60
atttttctct cataataaat cagtaccagc tatcgattat taaccaacca gtagtatttt     120
tctctcacaa caaatcagca ccaacaacca accaaccgaa aagagttttt tttccgctgc     180
cggtgggccc actcccatct agttgcacca cgcacgcccc cagcgagcgt agttgactcg     240
tattgcagcc acgaaacgag gcccccaccc ttccttcctt ttttttgct atccaccgc       300 aacgagaggc caggagcggc cgccaaatat cttctatacg ccccgcgatc tctaccgccc     360
cgacaaaata aaaatcgcgc accaaaatat ctcccccgcc ggagggagca cgagatggta     420
ccgcggccgc aagctttcta gaatccgcaa agtttctgca ccgttttcac cccctaacta     480
acaatatagg gaacgtgtgc taaatataaa atgagacctt atatgtag cgctgataac       540 tagaactatg c                                                         551

<210> SEQ ID NO 9
<211> LENGTH: 571
<212> TYPE: DNA
<213> ORGANISM: Artificial Sequence
<220> FEATURE:
<223> OTHER INFORMATION: Chromosomal flanking sequence from St.
      Augustinegrass event Ss026-2475
<220> FEATURE:
<221> NAME/KEY: primer_bind
<222> LOCATION: (1)..(24)
<223> OTHER INFORMATION: Binding site for Primer 2475 TAIL GO 1 3-2
<220> FEATURE:
<221> NAME/KEY: misc_feature
<222> LOCATION: (1)..(309)
<223> OTHER INFORMATION: genomic DNA
<220> FEATURE:
<221> NAME/KEY: misc_feature
<222> LOCATION: (310)..(571)
<223> OTHER INFORMATION: transgene DNA
<220> FEATURE:
<221> NAME/KEY: primer_bind
<222> LOCATION: (543)..(571)
<223> OTHER INFORMATION: Binding site for Primer 415 GOB1 5-2

<400> SEQUENCE: 9
ctcgcgacat ccgaaaacta gaggacaaaa agagtcagat cggagagttg attggattgg      60
atgagtttga tggccgcgaa ggcatcggtt tggattcccc agattaccaa ttcagtctat     120
ggctgtctcc aagatgtcat gatacaacaa tcaagcacga accatcagca tagcataggt     180
ccttccatag ttctgtcgca atcagcagct ttctgtacca tgccagtacg ttgtagcaaa     240
gacaagtttt tgttttgtac acctgctgat gtgttttgta accgtcgttg taggaccagt     300
tgtctgatag tggtaccgcg gccgcaagct tctagaatc cgaaaagttt ctgcaccgtt      360
ttcaccccct aactaacaat atagggaacg tgtgctaaat ataaaatgag accttatata     420
tgtagcgctg ataactagaa ctatgcaaga aaaactcatc cacctacttt agtggcaatc     480
gggctaaata aaaagagtc gctacactag tttcgttttc cttagtaatt aagtgggaaa      540
atgaaatcat tattgcttag aatatacgtt c                                   571

<210> SEQ ID NO 10
<211> LENGTH: 345
<212> TYPE: DNA
<213> ORGANISM: Artificial Sequence
```

```
<220> FEATURE:
<223> OTHER INFORMATION: Chromosomal flanking sequence from St.
      Augustinegrass event Ss026-2623
<220> FEATURE:
<221> NAME/KEY: primer_bind
<222> LOCATION: (1)..(23)
<223> OTHER INFORMATION: Binding site for Primer 2623 GOB1 1-3 D
<220> FEATURE:
<221> NAME/KEY: misc_feature
<222> LOCATION: (1)..(244)
<223> OTHER INFORMATION: genomic DNA
<220> FEATURE:
<221> NAME/KEY: misc_feature
<222> LOCATION: (245)..(345)
<223> OTHER INFORMATION: transgene DNA
<220> FEATURE:
<221> NAME/KEY: primer_bind
<222> LOCATION: (322)..(345)
<223> OTHER INFORMATION: Binding site for Primer 761 EPJ 5-2

<400> SEQUENCE: 10
atgcttcaag ctggtcagat ccgtaagttt cctctcataa accccagcga agaaatactg      60
atggaactgc ttctccaaat cggcccaagt tatgatggaa ttggccggaa gtgaagtaaa     120
ccaagcaaag gctggaccag acaaagatga tgaaaacagc ctgactctaa gctcatcttg     180
catagctgcc tctccacact gaataatgaa tttattgatg tgctcaactg tggaggtttc     240
gtttatagtg ccctttttccc ctcttcctga tcttgtttag catggcggaa attttaaacc     300
ccccatcatc tccccaaca acggcggatc gcagatctac atccg                      345

<210> SEQ ID NO 11
<211> LENGTH: 572
<212> TYPE: DNA
<213> ORGANISM: Artificial Sequence
<220> FEATURE:
<223> OTHER INFORMATION: Chromosomal flanking sequence from St.
      Augustinegrass event Ss026-2640
<220> FEATURE:
<221> NAME/KEY: primer_bind
<222> LOCATION: (1)..(26)
<223> OTHER INFORMATION: Binding site for Primer 2640 RU Fs 1 3-1
<220> FEATURE:
<221> NAME/KEY: misc_feature
<222> LOCATION: (1)..(448)
<223> OTHER INFORMATION: genomic DNA
<220> FEATURE:
<221> NAME/KEY: misc_feature
<222> LOCATION: (449)..(572)
<223> OTHER INFORMATION: transgene DNA
<220> FEATURE:
<221> NAME/KEY: primer_bind
<222> LOCATION: (547)..(572)

<400> SEQUENCE: 11
gtattttgga cgagcatact gcatacataa tactttggtt gctcatatca tttgattcgt      60
atatggggtg gtgtgaaata atgataattt ttttgtttgg ttaggtgaac tgtaccatcc     120
catctaaaat gaagttatct cacctaatat ttttctgct aataaaaatg aatcatataa      180
ttcaagtaac ttggttgaac cctccgttca aaatcatctc atacatgcat cacatgatga     240
ttgcaccaaa cacaccctcc gccgcgttaa tgccggagat tactggagaa actgaagaaa     300
agaaagggag aggggagtcg agctctgggc cgccaaaacc ctttgctccg ttgattcagg     360
cccaacatgg aaatgggcta ggccagcgac gacttgtgac gaaaagcgga attccggaca     420
actgggcgca tgtggtccaa acaaaggata ccgcggccgc aagcttgtcg acctgatgat     480
tattttgttg atcatgattt tcttttggct atttgatttt ttgaaagata ttttttttccc     540 tgggaagaca cctatgggac gaagatatta tg                                  572
```

```
<210> SEQ ID NO 12
<211> LENGTH: 358
<212> TYPE: DNA
<213> ORGANISM: Artificial Sequence
<220> FEATURE:
<223> OTHER INFORMATION: Chromosomal flanking sequence from St.
      Augustinegrass event Ss026-2693
<220> FEATURE:
<221> NAME/KEY: primer_bind
<222> LOCATION: (1)..(25)
<223> OTHER INFORMATION: Binding site for primer 2693 RU Sn1 3-5
<220> FEATURE:
<221> NAME/KEY: misc_feature
<222> LOCATION: (1)..(16)
<223> OTHER INFORMATION: genomic DNA
<220> FEATURE:
<221> NAME/KEY: misc_feature
<222> LOCATION: (17)..(358)
<223> OTHER INFORMATION: transgene DNA
<220> FEATURE:
<221> NAME/KEY: primer_bind
<222> LOCATION: (326)..(358)
<223> OTHER INFORMATION: Binding site for primer PGO2 rev

<400> SEQUENCE: 12
gaagtacaaa ctgtccaaaa aatagaatga agatattctg aacgtattgg caaagattta      60
aacatataat tatataattt tatagtttgt gcattcgtca tatcgcacat cattaaggac     120
atgtcttact ccatcccaat tttatttag taattaaaga caattgactt attttatta     180 tttatctttt ttcgattaga tgcaaggtac ttacgcacac actttgtggt catgtgcatt     240
tgtgagtgca cctcctcaat acaagttcaa ctagcaaaca atctctaata ttactcgcct     300
atttaataca tttaggtagc aatatctgaa ttcaagcact ccaccatcac cagaccac      358

<210> SEQ ID NO 13
<211> LENGTH: 683
<212> TYPE: DNA
<213> ORGANISM: Artificial Sequence
<220> FEATURE:
<223> OTHER INFORMATION: Chromosomal flanking sequence from St.
      Augustinegrass event Ss026-2732
<220> FEATURE:
<221> NAME/KEY: primer_bind
<222> LOCATION: (1)..(24)
<223> OTHER INFORMATION: Binding site of Primer 2732 RU Fs 1 3-2
<220> FEATURE:
<221> NAME/KEY: misc_feature
<222> LOCATION: (1)..(557)
<223> OTHER INFORMATION: genomic DNA
<220> FEATURE:
<221> NAME/KEY: misc_feature
<222> LOCATION: (558)..(683)
<223> OTHER INFORMATION: transgene DNA
<220> FEATURE:
<221> NAME/KEY: primer_bind
<222> LOCATION: (658)..(683)
<223> OTHER INFORMATION: Binding site for Primer PRU 761 f1-1

<400> SEQUENCE: 13
cggcctgttt atctttggac tatgtccaac agagccatgt ggttcaatgt tcatcgctat      60
cgtgacaagc gttgtcatgg taatgaggtt cccaagatca tgttgcttga tgttcatact     120
ggaagtgcag aaactcatgg gaggtttgaa gtcgtagttt ggacatcacg catacccccg     180
taccacagct acctggtgag ctgcgagatg ggggcaccaa ttctgatggc caagaagaag     240
cggcctcact ccacggtgtg attcaaactc atctgcagat accaacacga tgtaactgtc     300
tctgttcatc aacaatttta atttcattgc tggagtcagt ttaacatgtt acaagttgcc     360
```

```
agacattatc tgaaattttt tcttaatttg cagttggcag ggacaatatg taatgaatga      420
ggctatccat ggacacactg gtagcagcag atgatgcttg catctgcaga cggcgtgccc      480
tctccctcat cagagcttgg agcgaaataa catctggctc tactttagtg gtacacaggg      540
taccagggca agtgagcggt accgcggccg caagcttgtc gacctgatga ttattttgtt      600
gatcatgatt ttcttttggc tatttgattt tttgaaagat attttttttcc ctgggaagac     660 acctatggga cgaagatatt atg                                              683
```

<210> SEQ ID NO 14
<211> LENGTH: 172
<212> TYPE: DNA
<213> ORGANISM: Artificial Sequence
<220> FEATURE:
<223> OTHER INFORMATION: Chromosomal flanking sequence from St.
      Augustinegrass event Ss026-2749
<220> FEATURE:
<221> NAME/KEY: primer_bind
<222> LOCATION: (1)..(26)
<223> OTHER INFORMATION: Binding site for Primer 2749 RU468 1-2 3-3
<220> FEATURE:
<221> NAME/KEY: misc_feature
<222> LOCATION: (1)..(134)
<223> OTHER INFORMATION: genomic DNA
<220> FEATURE:
<221> NAME/KEY: misc_feature
<222> LOCATION: (135)..(172)
<223> OTHER INFORMATION: transgene DNA
<220> FEATURE:
<221> NAME/KEY: primer_bind
<222> LOCATION: (147)..(172)
<223> OTHER INFORMATION: Binding site for Primer PRU761 f1-1

<400> SEQUENCE: 14

```
tggaggaaga gaagatagag agaatcaccc ccacgtgctt gcgctgcggg cgctcggaag       60
aagaatttga cggttgcagc ccggaaaggg cgaaagggaa aagggaaaag ggtacggtgt      120
aggttcccac gatctttccc tgggaagaca cctatgggac gaagatatta tg             172
```

<210> SEQ ID NO 15
<211> LENGTH: 28
<212> TYPE: DNA
<213> ORGANISM: Artificial Sequence
<220> FEATURE:
<223> OTHER INFORMATION: Primer for genomic/transgene junction 1819 ZS
      Sn 1

<400> SEQUENCE: 15

```
ggtcctttat agggaaagca tatcatag                                          28
```

<210> SEQ ID NO 16
<211> LENGTH: 33
<212> TYPE: DNA
<213> ORGANISM: Artificial Sequence
<220> FEATURE:
<223> OTHER INFORMATION: Primer for genomic/transgene junction 1819 ZS
      Sn 1

<400> SEQUENCE: 16

```
gcagagacac agagccttca ttaaccaaac ttc                                    33
```

<210> SEQ ID NO 17
<211> LENGTH: 24
<212> TYPE: DNA
<213> ORGANISM: Artificial Sequence
<220> FEATURE:
<223> OTHER INFORMATION: Primer for genomic/transgene junction 1984 RU
      FNS 1

```
<400> SEQUENCE: 17
tggctggaca gggatttcgt gact                                          24

<210> SEQ ID NO 18
<211> LENGTH: 26
<212> TYPE: DNA
<213> ORGANISM: Artificial Sequence
<220> FEATURE:
<223> OTHER INFORMATION: Primer for genomic/transgene junction 1984 RU
      FNS 1

<400> SEQUENCE: 18
cataatatct tcgtcccata ggtgtc                                        26

<210> SEQ ID NO 19
<211> LENGTH: 32
<212> TYPE: DNA
<213> ORGANISM: Artificial Sequence
<220> FEATURE:
<223> OTHER INFORMATION: Primer for genomic/transgene junction 2006 TAIL
      GO 1

<400> SEQUENCE: 19
gatccacatg tgcatctcgt tatggcctgg gt                                 32

<210> SEQ ID NO 20
<211> LENGTH: 35
<212> TYPE: DNA
<213> ORGANISM: Artificial Sequence
<220> FEATURE:
<223> OTHER INFORMATION: Primer for genomic/transgene junction 2006 TAIL
      GO 1

<400> SEQUENCE: 20
gcatagttct agttatcagc gctacatata taagg                              35

<210> SEQ ID NO 21
<211> LENGTH: 29
<212> TYPE: DNA
<213> ORGANISM: Artificial Sequence
<220> FEATURE:
<223> OTHER INFORMATION: Primer for genomic/transgene junction 2027 ZS 2

<400> SEQUENCE: 21
cttaggtgga aggcgaagaa ggccccctt                                     29

<210> SEQ ID NO 22
<211> LENGTH: 31
<212> TYPE: DNA
<213> ORGANISM: Artificial Sequence
<220> FEATURE:
<223> OTHER INFORMATION: Primer for genomic/transgene junction 2050 TAIL
      GO 1

<400> SEQUENCE: 22
gttgacgtgc gtacgaacaa acgagtttca g                                  31

<210> SEQ ID NO 23
<211> LENGTH: 29
<212> TYPE: DNA
<213> ORGANISM: Artificial Sequence
<220> FEATURE:
<223> OTHER INFORMATION: Primer for genomic/transgene junction 2085 GO
      Sn 1

<400> SEQUENCE: 23
```
gagccgactc atgcctaatg cttctctag                                    29

<210> SEQ ID NO 24
<211> LENGTH: 25
<212> TYPE: DNA
<213> ORGANISM: Artificial Sequence
<220> FEATURE:
<223> OTHER INFORMATION: Primer for genomic/transgene junction 2085 SZ
      Sn 1

<400> SEQUENCE: 24
tattacagcg ccttctaata atgtc                                        25

<210> SEQ ID NO 25
<211> LENGTH: 30
<212> TYPE: DNA
<213> ORGANISM: Artificial Sequence
<220> FEATURE:
<223> OTHER INFORMATION: Primer for genomic/transgene junction 2085 SZ
      Sn 1

<400> SEQUENCE: 25
ctccttggcg gcggtggcca cgagcctgga                                   30

<210> SEQ ID NO 26
<211> LENGTH: 28
<212> TYPE: DNA
<213> ORGANISM: Artificial Sequence
<220> FEATURE:
<223> OTHER INFORMATION: Primer for genomic/transgene junction 2393 GO
      Sn 1

<400> SEQUENCE: 26
cggtgcgcct tcgcccactt tcggttag                                     28

<210> SEQ ID NO 27
<211> LENGTH: 24
<212> TYPE: DNA
<213> ORGANISM: Artificial Sequence
<220> FEATURE:
<223> OTHER INFORMATION: Primer for genomic/transgene junction 2475 TAIL
      GO 1

<400> SEQUENCE: 27
ctcgcgacat ccgaaaacta gagg                                         24

<210> SEQ ID NO 28
<211> LENGTH: 29
<212> TYPE: DNA
<213> ORGANISM: Artificial Sequence
<220> FEATURE:
<223> OTHER INFORMATION: Primer for genomic/transgene junction 2475 TAIL
      GO 1

<400> SEQUENCE: 28
gaacgtatat tctaagcaat aatgatttc                                    29

<210> SEQ ID NO 29
<211> LENGTH: 23
<212> TYPE: DNA
<213> ORGANISM: Artificial Sequence
<220> FEATURE:
<223> OTHER INFORMATION: Primer for genomic/transgene junction 2623 TAIL
      GOB1 1-3

<400> SEQUENCE: 29

```
atgcttcaag ctggtcagat ccg                                           23

<210> SEQ ID NO 30
<211> LENGTH: 24
<212> TYPE: DNA
<213> ORGANISM: Artificial Sequence
<220> FEATURE:
<223> OTHER INFORMATION: Primer for genomic/transgene junction 2623 TAIL
      GOB1 1-3

<400> SEQUENCE: 30
cggatgtaga tctgcgatcc gccg                                          24

<210> SEQ ID NO 31
<211> LENGTH: 26
<212> TYPE: DNA
<213> ORGANISM: Artificial Sequence
<220> FEATURE:
<223> OTHER INFORMATION: Primer for genomic/transgene junction 2640 RU
      Fs 1

<400> SEQUENCE: 31
gtattttgga cgagcatact gcatac                                        26

<210> SEQ ID NO 32
<211> LENGTH: 25
<212> TYPE: DNA
<213> ORGANISM: Artificial Sequence
<220> FEATURE:
<223> OTHER INFORMATION: Primer 1:  2693 RU Sn1 3-5; Primer for
      genomic/transgene junction 2693 RU Sn 1

<400> SEQUENCE: 32
gaagtacaaa ctgtccaaaa aatag                                         25

<210> SEQ ID NO 33
<211> LENGTH: 33
<212> TYPE: DNA
<213> ORGANISM: Artificial Sequence
<220> FEATURE:
<223> OTHER INFORMATION: Primer 2:  PGO2 rev; Primer for
      genomic/transgene junction 2693 RU SN 1

<400> SEQUENCE: 33
gtggtctggt gatggtggag tgcttgaatt cag                                33

<210> SEQ ID NO 34
<211> LENGTH: 24
<212> TYPE: DNA
<213> ORGANISM: Artificial Sequence
<220> FEATURE:
<223> OTHER INFORMATION: Primer for genomic/transgene junction 2732 RU
      Fs 1

<400> SEQUENCE: 34
cggcctgttt atctttggac tatg                                          24

<210> SEQ ID NO 35
<211> LENGTH: 26
<212> TYPE: DNA
<213> ORGANISM: Artificial Sequence
<220> FEATURE:
<223> OTHER INFORMATION: Primer for genomic/transgene junction 2749
      RUrev468 1-2

<400> SEQUENCE: 35
tggaggaaga gaagatagag agaatc                                        26
```

-continued

```
<210> SEQ ID NO 36
<211> LENGTH: 1569
<212> TYPE: DNA
<213> ORGANISM: Artificial Sequence
<220> FEATURE:
<223> OTHER INFORMATION: cDNA for a variant of the enzyme 5-enolpyruvyl-
      3-phoshoshikimate synthase (EPSPS)

<400> SEQUENCE: 36
ccatggccca ggtgtcccgc atctgcaacg gcgtgcagaa cccatccctc atctccaacc      60
tctccaagtc ctcccagcgc aagtccccac tctccgtgtc cctcaagacc cagcaacacc     120
cacgcgccta cccaatctcc agctcctggg cctcaagaa gtccggcatg accctcatcg      180
gctccgagct gcgcccactc aaggtgatgt cctccgtgtc caccgccgag aaggcctccg     240
agatcgtgct ccagccaatc cgcgagattt ccggcctcat caagctccca ggctccaagt     300
ccctctccaa ccgcatcctc ctgctcgccg ctctctccga gggcaccacc gtggtggaca     360
acctgctcaa ctccgacgac atcaactaca tgctcgacgc cctcaagcgc ctcggcctca     420
acgtggagac cgactccgag aacaaccgcg ccgtggtgga gggctgcggc ggcatcttcc     480
cagcctccat cgattccaag tccgacatcg agctgtacct cggcaactcc ggcacctgca     540
tgaggtcact cacggcggcg gtcaccgcgg ctggcggcaa cgcctcctac gtgctcgacg     600
gcgtgccaag gatgcgcgag cgcccaatcg cgacctcgt ggtgggcctc aagcaactcg      660
gcgccgacgt ggagtgcacc ctcggcacca actgcccacc agtgcgcgtg aacgccaacg     720
gcggcctccc aggcggcaag gtgaagctct ccggctccat ctcctcccag tacctcaccg     780
ccctgctcat gtccgcccca ctcgccctcg gcgacgtgga gatcgagatc gtggacaagc     840
tcatctccgt gccatacgtg gagatgaccc tcaagtctca tggagcgcttc ggcgtgtccg     900
tggagcactc cgacagctgg gaccgcttct tcgtgaaggg cggccagaag tacaagtccc     960
caggcaacgc ctacgtggag ggcgacgcct cctccgcctc ctacttcctc gctggcgctg    1020
ccatcaccgg cgagaccgtg accgtggagg ggtgcggcac caccagcctc aaggcgacg     1080
tgaagttcgc cgaggtgctc gagaagatgg gctgcaaggt gtcctggacc gagaactccg    1140
tgaccgtgac cggcccacca agggacgcct tcggcatgag gcacctccgc gccatcgacg    1200
tgaacatgaa caagatgcca gacgtggcca tgacccctcgc cgtggtgcc ctcttcgccg    1260
acggcccaac caccatcagg gacgtggcca gctggcgcgt gaaggagacc gagcgcatga    1320
tcgccatctg caccgagctg agaaagctcg gcgccaccgt cgaggagggc tccgactact    1380
gcgtgatcac cccaccaaag aaggtcaaga ccgccgagat cgacacctac gacgaccacc    1440
gcatggcgat ggccttctcc ctcgccgcct gcgccgacgt gccgatcacc atcaacgacc    1500
caggctgcac ccgcaagacc ttcccagact acttccaggt gctcgagcgc atcaccaagc    1560
actgagctc                                                            1569

<210> SEQ ID NO 37
<211> LENGTH: 3446
<212> TYPE: DNA
<213> ORGANISM: Artificial Sequence
<220> FEATURE:
<223> OTHER INFORMATION: Transgene (cDNA) of the EPSPS cassette
<220> FEATURE:
<221> NAME/KEY: promoter
<222> LOCATION: (1)..(917)
<223> OTHER INFORMATION: PRUBQ promoter sequence
<220> FEATURE:
<221> NAME/KEY: Intron
```

```
<222> LOCATION: (918)..(1405)
<223> OTHER INFORMATION: rice actin intron
<220> FEATURE:
<221> NAME/KEY: gene
<222> LOCATION: (1406)..(2972)
<223> OTHER INFORMATION: EPSPS coding sequence
<220> FEATURE:
<221> NAME/KEY: misc_structure
<222> LOCATION: (2973)..(3446)
<223> OTHER INFORMATION: Zea mays alcohol dehydrogenase 3' untranslated
      region

<400> SEQUENCE: 37
```

| | | | | | |
|---|---|---|---|---|---|
| acgcgtggta | ccgcggccgc | aagcttgtcg | acctgatgat | tattttgttg | atcatgattt     60 |
| tcttttggct | atttgatttt | ttgaaagata | ttttttttccc | tgggaagaca | cctatgggac    120 |
| gaagatatta | tgttatatat | atatatatat | atatatcaca | tcagtctctg | cacaaagtgc    180 |
| atcctgggct | gcttcaatta | taaagcccca | ttcaccacat | ttgctagata | gtcgaaaagc    240 |
| accatcaata | ttgagcttca | ggtattttttg | gttgtgttgt | ggttggattg | attctaatat    300 |
| ataccaaatc | aatataattc | actaccaaaa | tataccatag | ccatcacaac | tttattaatt    360 |
| ttggtagctt | aagatggtat | atataataac | caattaacaa | ctgattctaa | ttttactacg    420 |
| gcccagtatc | taccaataca | aaacaacgag | tatgttttct | tccgtcgtaa | tcgtacacag    480 |
| tacaaaaaaa | cctggccagc | cttttcttggg | ctggggctct | ctttcgaaag | gtcacaaaac    540 |
| gtacacggca | gtaacgccgc | ttcgctgcgt | gttaacggcc | accaaccccg | ccgtgagcaa    600 |
| acggcatcag | ctttccacct | cctcgatatc | tccgcggcgc | cgtctggacc | cgccccttt     660 |
| ccgttccttt | ctttccttct | cgcgtttgcg | tggtggggac | ggactcccca | aaccgcctct    720 |
| ccctctcttt | atttgtctat | attctcactg | gccccaccc  | accgcacccc | tgggcccact    780 |
| cacgagtccc | cccctcccca | cctataaata | ccccacccccc | cctcgcctc  | ttcctccatc    840 |
| aatcgaatcc | ccaaaatcgc | agagaaaaaa | aaatctcccc | tcgaagcgaa | gcgtcgaatc    900 |
| gccttctcaa | gtctagatcc | gccgccgccg | gtaaccaccc | cgccccctctc | ctctttcttt   960 |
| ctccgttttt | tttttccgtc | tcggtctcga | tctttggcct | tggtagtttg | ggtgggcgag   1020 |
| aggcggcttc | gtgcgcgccc | agatcggtgc | gcgggagggg | cgggatctcg | cggctggggc   1080 |
| tctcgccggc | gtggatccgg | cccggatctc | gcggggaatg | gggctctcgg | atgtagatct   1140 |
| gcgatccgcc | gttgttgggg | gagatgatgg | ggggtttaaa | atttccgcca | tgctaaacaa   1200 |
| gatcaggaag | aggggaaaag | ggcactatgg | tttatatttt | tatatatttc | tgctgcttcg   1260 |
| tcaggcttag | atgtgctaga | tcttttctttc | ttcttttttgt | gggtagaatt | tgaatccctc   1320 |
| agcattgttc | atcggtagtt | tttctttttca | tgatttgtga | caaatgcagc | ctcgtgcgga   1380 |
| gcttttttgt | aggtagaagg | gatccatggc | ccaggtgtcc | cgcatctgca | acggcgtgca   1440 |
| gaacccatcc | ctcatctcca | acctctccaa | gtcctcccag | cgcaagtccc | cactctccgt   1500 |
| gtccctcaag | acccagcaac | acccacgcgc | ctacccaatc | tccagctcct | ggggcctcaa   1560 |
| gaagtccggc | atgaccctca | tcggctccga | gctgcgccca | ctcaaggtga | tgtcctccgt   1620 |
| gtccaccgcc | gagaaggcct | ccgagatcgt | gctccagcca | atccgcgaga | tttccggcct   1680 |
| catcaagctc | ccaggctcca | agtccctctc | caaccgcatc | ctcctgctcg | ccgctctctc   1740 |
| cgagggcacc | accgtggtgg | acaacctgct | caactccgac | gacatcaact | acatgctcga   1800 |
| cgccctcaag | cgcctcggcc | tcaacgtgga | gaccgactcc | gagaacaacc | gcgccgtggt   1860 |
| ggagggctgc | ggcggcatct | tcccagccctc | catcgattac | aagtccgaca | tcgagctgta   1920 |
| cctcggcaac | tccggcaccc | gcatgaggtc | actcacggcg | gcggtcaccg | cggctggcgg   1980 |

```
caacgcctcc tacgtgctcg acggcgtgcc aaggatgcgc gagcgcccaa tcggcgacct    2040
cgtggtgggc ctcaagcaac tcggcgccga cgtggagtgc accctcggca ccaactgccc    2100
accagtgcgc gtgaacgcca acggcggcct cccaggcggc aaggtgaagc tctccggctc    2160
catctcctcc cagtacctca ccgccctgct catgtccgcc ccactcgccc tcggcgacgt    2220
ggagatcgag atcgtggaca agctcatctc cgtgccatac gtggagatga ccctcaagct    2280
catggagcgc ttcggcgtgt ccgtggagca ctccgacagc tgggaccgct tcttcgtgaa    2340
gggcggccag aagtacaagt ccccaggcaa cgcctacgtg gagggcgacg cctcctccgc    2400
ctcctacttc ctcgctggcg ctgccatcac cggcgagacc gtgaccgtgg aggggtgcgg    2460
caccaccagc ctccaaggcg acgtgaagtt cgccgaggtg ctcgagaaga tgggctgcaa    2520
ggtgtcctgg accgagaact ccgtgaccgt gaccggccca ccaagggacg ccttcggcat    2580
gaggcacctc cgcgccatcg acgtgaacat gaacaagatg ccagacgtgg ccatgaccct    2640
cgccgtggtg gccctcttcg ccgacggccc aaccaccatc agggacgtgg ccagctggcg    2700
cgtgaaggag accgagcgca tgatcgccat ctgcaccgag ctgagaaagc tcggcgccac    2760
cgtcgaggag ggctccgact actgcgtgat caccccacca aagaaggtca agaccgccga    2820
gatcgacacc tacgacgacc accgcatggc gatggccttc tccctcgccg cctgcgccga    2880
cgtgccgatc accatcaacg acccaggctg cacccgcaag accttcccag actacttcca    2940
ggtgctcgag cgcatcacca agcactgagc tcgaattcag cttcattgca agctagctcc    3000
tcctgcaggg caggcatgtc gcacagcaaa tgggcatgaa agttgaagg cgctccagtc    3060 ctccagcttg tgtagtacac agtagcaata aacgttagt gtttgtcctg tgcccatcct    3120
gtattattct gttccagggt ttcacctta tcgtcagtgt gtggtcaggt ttcaacccctt    3180 ctcagaacaa cccccctccca gaaaaaaaac aaaggaagaa gtttgtgtcc aggtttcaga    3240
atcccctgtc tgtaattacc attttgcatg acaataatga gatactgtag atattaataa    3300
tgttccagac cttcaaggcc tccctccctc gcaaattgca gatttacttg aggtatcatt    3360
cggtattcac aaaatgtaac gtaaatagta gtgattaaca ctcgattacc agcgataggc    3420
agtttgaata agacggcccg gggcgg                                          3446
```

<210> SEQ ID NO 38
<211> LENGTH: 1137
<212> TYPE: DNA
<213> ORGANISM: Artificial Sequence
<220> FEATURE:
<223> OTHER INFORMATION: Transgene (cDNA) for Gibberellic Acid 2-Oxidase
      (GA2OX) Nucleic Acid

<400> SEQUENCE: 38

```
ggatccatgg cctccaccaa ggtggtcgag cacctcaagg agaacgtcct ctggaagcag     60
gccatcatgg accgcaacgc caacatctcc gaccccaccgt tcgaggagac ctacaagaac   120
ctcctgctca agcacaacat caccccgctc accaccacca cgaccacgac gaccaccacg    180
gcgaccatcg aggtgaggga tctcccactc atcgacctct ccaggctcgt ggccaccgcc    240
gccaaggagc gcgagaactg caagagggat atcgccaacg cctcccgcga gtggggcttc    300
ttccaggtgg tgaaccacgg catcccgcat aggatgctcg aggagatgaa caaggagcag    360
gtcaaggtgt ccgcgagcc gttcaacaag aagaagggcg acaactgcat gaacctcagg    420
ctctccccag gctcctacag gtggggctcc ccgaccccga actgcctctc ccagctctcc    480
tggtccgagg ccttccacat cccgatgaac gacatctgct ccaacgcccc gaggaacatt    540
```

-continued

| | |
|---|---|
| gccaacggca acccgaacat ctccaacctc tgctccaccg tgaagcagtt cgccaccacc | 600 |
| gtgtccgagc tggccaacaa gctcgccaac atcctcgtcg agaagctcgg ccatgacgag | 660 |
| ctgaccttca tcgaggagaa gtgctccccg aacacgtgct acctcaggat gaaccgctac | 720 |
| ccgccgtgcc caaagtactc ccacgtgctc ggcctcatgc acataccga ctccgacttc | 780 |
| ctcaccatcc tctaccagga ccaggtgggc ggcctccagc tcgtgaagga cggccgctgg | 840 |
| atttccgtga agccgaaccc agaggccctc atcgtgaaca tcggcgacct cttccaggcc | 900 |
| tggtctaacg gcgtgtacaa gtccgtggtg catagggtgg tggccaaccc gaggttcgag | 960 |
| aggttctcta ccgcctactt cctctgcccg tccggcgacg ccgtgatcca gtcctaccgc | 1020 |
| gagccgtcta tgtaccgcaa gttcagcttc ggcgagtaca ggcagcaggt ccagcaggac | 1080 |
| gtgcgcgagt tcggccacaa gatcggcctc tcccgcttcc tcatctgcaa cgagctc | 1137 |

<210> SEQ ID NO 39
<211> LENGTH: 3696
<212> TYPE: DNA
<213> ORGANISM: Artificial Sequence
<220> FEATURE:
<223> OTHER INFORMATION: Transgene (cDNA) of the GA2OX cassette
<220> FEATURE:
<221> NAME/KEY: promoter
<222> LOCATION: (1)..(2222)
<223> OTHER INFORMATION: GOS2 promoter site
<220> FEATURE:
<221> NAME/KEY: gene
<222> LOCATION: (2226)..(3362)
<223> OTHER INFORMATION: GA2OX coding sequence
<220> FEATURE:
<221> NAME/KEY: 3'UTR
<222> LOCATION: (3363)..(3696)
<223> OTHER INFORMATION: SpH 3' untranslated region (3'-UTR)

<400> SEQUENCE: 39

| | |
|---|---|
| acgcgtggta ccgcggccgc aagctttcta gaatccgaaa agtttctgca ccgttttcac | 60 |
| cccctaacta acaatatagg gaacgtgtgc taaatataaa atgagacctt atatatgtag | 120 |
| cgctgataac tagaactatg caagaaaaac tcatccacct actttagtgg caatcgggct | 180 |
| aaataaaaaa gagtcgctac actagtttcg ttttccttag taattaagtg ggaaaatgaa | 240 |
| atcattattg cttagaatat acgttcacat ctctgtcatg aagttaaatt attcgaggta | 300 |
| gccataattg tcatcaaact cttcttgaat aaaaaaatct ttctagctga actcaatggg | 360 |
| taaagagaga gatttttttt aaaaaaatag aatgaagata ttctgaacgt attggcaaag | 420 |
| atttaaacat ataattatat aatttttatag tttgtgcatt cgtcatatcg cacatcatta | 480 |
| aggacatgtc ttactccatc ccaatttta tttagtaatt aaagacaatt gacttatttt | 540 |
| tattatttat ctttttcga ttagatgcaa ggtacttacg cacacacttt gtgctcatgt | 600 |
| gcatgtgtga gtgcacctcc tcaatacacg ttcaactagc aacacatctc taatatcact | 660 |
| cgcctattta atacatttag gtagcaatat ctgaattcaa gcactccacc atcaccagac | 720 |
| cactttttaat aatatctaaa atacaaaaaa taattttaca gaatagcatg aaaagtatga | 780 |
| aacgaactat ttaggttttt cacatacaaa aaaaaaaga attttgctcg tgcgcgagcg | 840 |
| ccaatctccc atattgggca cacaggcaac aacagagtgg ctgcccacag aacaacccac | 900 |
| aaaaaacgat gatctaacgg aggacagcaa gtccgcaaca accttttaac agcaggcttt | 960 |
| gcggccagga gagaggagga gaggcaaaga aaaccaagca tcctcctcct cccatctata | 1020 |
| aattcctccc ccctttttccc ctctctatat aggaggcatc caagccaaga agagggagag | 1080 |

-continued

```
caccaaggac acgcgactag cagaagccga gcgaccgcct tcttcgatcc atatcttccg    1140
gtcgagttct tggtcgatct cttccctcct ccacctcctc ctcacagggt atgtgccctt    1200
cggttgttct tggatttatt gttctaggtt gtgtagtacg ggcgttgatg ttaggaaagg    1260
ggatctgtat ctgtgatgat tcctgttctt ggatttggga tagaggggtt cttgatgttg    1320
catgttatcg gttcggtttg attagtagta tggttttcaa tcgtctggag agctctatgg    1380
aaatgaaatg gtttagggta cggaatcttg cgattttgtg agtaccttt gtttgaggta     1440 aaatcagagc accggtgatt ttgcttggtg taataaaagt acggttgttt ggtcctcgat    1500
tctggtagtg atgcttctcg atttgacgaa gctatccttt gtttattccc tattgaacaa    1560
aaataatcca actttgaaga cggtcccgtt gatgagattg aatgattgat tcttaagcct    1620
gtccaaaatt tcgcagctgg cttgtttaga tacagtagtc cccatcacga aattcatgga    1680
aacagttata atcctcagga acaggggatt ccctgttctt ccgatttgct ttagtcccag    1740 aattttttt cccaaatatc ttaaaaagtc actttctggt tcagttcaat gaattgattg     1800
ctacaaataa tgctttata gcgttatcct agctgtagtt cagttaatag gtaatacccc     1860
tatagtttag tcaggagaag aacttatccg atttctgatc tccatttta attatatgaa     1920 atgaactgta gcataagcag tattcatttg gattatttt tttattagct ctcaccctt      1980 cattattctg agctgaaagt ctggcatgaa ctgtcctcaa ttttgttttc aaattcacat    2040
cgattatcta tcgattatcc tcttgtatct acctgtagaa gttctttttt ggttattcct    2100
tgactgcttg attacagaaa gaaatttatg aagctgtaat cgggatagtt atactgcttg    2160
ttcttatgat tcatttcctt tgtgcagttc ttggtgtagc ttgccacttt caccagcaaa    2220
gtttcggatc catggcctcc accaaggtgg tcgagcacct caaggagaac gtcctctgga    2280
agcaggccat catggaccgc aacgccaaca tctccgaccc accgttcgag gagacctaca    2340
agaacctcct gctcaagcac aacatcaccc cgctcaccac caccacgacc acgacgacca    2400
ccacggcgac catcgaggtg agggatctcc cactcatcga cctctccagg ctcgtggcca    2460
ccgccgccaa ggagcgcgag aactgcaaga gggatatcgc caacgcctcc cgcgagtggg    2520
gcttcttcca ggtggtgaac cacggcatcc cgcataggat gctcgaggag atgaacaagg    2580
agcaggtcaa ggtgttccgc gagccgttca acaagaagaa gggcgacaac tgcatgaacc    2640
tcaggctctc cccaggctcc tacaggtggg gctccccgac cccgaactgc ctctcccagc    2700
tctcctggtc cgaggccttc cacatcccga tgaacgacat ctgctccaac gccccgagga    2760
acattgccaa cggcaacccg aacatctcca acctctgctc caccgtgaag cagttcgcca    2820
ccaccgtgtc cgagctggcc aacaagctcg ccaacatcct cgtcgagaag ctcggccatg    2880
acgagctgac cttcatcgag gagaagtgct ccccgaacac gtgctacctc aggatgaacc    2940
gctacccgcc gtgcccaaag tactcccacg tgctcggcct catgccacat accgactccg    3000
acttcctcac catcctctac caggaccagg tgggcggcct ccagctcgtg aaggacggcc    3060
gctggatttc cgtgaagccg aacccagagg ccctcatcgt gaacatcggc gacctcttcc    3120
aggcctggtc taacggcgtg tacaagtccg tggtgcatag ggtggtggcc aacccgaggt    3180
tcgagaggtt ctctaccgcc tacttcctct gcccgtccgg cgacgccgtg atccagtcct    3240
accgcgagcc gtctatgtac cgcaagttca gcttcggcga gtacaggcag caggtccagc    3300
aggacgtgcg cgagttcggc cacaagatcg gcctctcccg cttcctcatc tgcaacgagc    3360
tcgaattcgc atggcgtggg ataatacaga ctgtatatag gaggaataat ggtttgctgc    3420
ttgtagctct gtaaatagga aaatgaagct cagcttttac tttcagtcat ctagttcggt    3480
```

```
agtgtaggtc gggtttgctg aagtttggtt aatgaaggct ctgtgtctct gcaaattaag    3540
gcgttgttct gtcaataatc atcttttttc tgcaacatgc tttctttcaa atttgccgag    3600
ttacttttgt aatgatcatt aatggcattg tataatcatt gattggtcga cgataatcaa    3660
ttgcctgtat cacaaattca agacttcccg gggcgg                              3696
```

```
<210> SEQ ID NO 40
<211> LENGTH: 28
<212> TYPE: DNA
<213> ORGANISM: Artificial Sequence
<220> FEATURE:
<223> OTHER INFORMATION: Primer for GSP2 for HT end

<400> SEQUENCE: 40
catgatcaac aaaataatca tcaggtcg                                       28

<210> SEQ ID NO 41
<211> LENGTH: 36
<212> TYPE: DNA
<213> ORGANISM: Artificial Sequence
<220> FEATURE:
<223> OTHER INFORMATION: Primer for GSP2 for DWF end

<400> SEQUENCE: 41
cattttatat ttagcacacg ttccctatat tgttag                              36

<210> SEQ ID NO 42
<211> LENGTH: 31
<212> TYPE: DNA
<213> ORGANISM: Artificial Sequence
<220> FEATURE:
<223> OTHER INFORMATION: Primer for GSP1 for middle

<400> SEQUENCE: 42
cacctttatc gtcagtgtgt ggtcaggttt c                                   31

<210> SEQ ID NO 43
<211> LENGTH: 33
<212> TYPE: DNA
<213> ORGANISM: Artificial Sequence
<220> FEATURE:
<223> OTHER INFORMATION: Primer for GSP1 for middle

<400> SEQUENCE: 43
gaagtttggt taatgaaggc tctgtgtctc tgc                                 33

<210> SEQ ID NO 44
<211> LENGTH: 31
<212> TYPE: DNA
<213> ORGANISM: Artificial Sequence
<220> FEATURE:
<223> OTHER INFORMATION: Primer for GSP2 for middle

<400> SEQUENCE: 44
gaaacctgac cacacactga cgataaaggt g                                   31

<210> SEQ ID NO 45
<211> LENGTH: 29
<212> TYPE: DNA
<213> ORGANISM: Artificial Sequence
<220> FEATURE:
<223> OTHER INFORMATION: PRUrev608; alternate GSP1 for HT end

<400> SEQUENCE: 45
```
gatgccgttt gctcacggcg gggttggtg                                    29

<210> SEQ ID NO 46
<211> LENGTH: 33
<212> TYPE: DNA
<213> ORGANISM: Artificial Sequence
<220> FEATURE:
<223> OTHER INFORMATION: Primer PRUrev468; alternate GSP2 for HT end

<400> SEQUENCE: 46
gtactgtgta cgattacgac ggaagaaaac ata                               33

<210> SEQ ID NO 47
<211> LENGTH: 27
<212> TYPE: DNA
<213> ORGANISM: Artificial Sequence
<220> FEATURE:
<223> OTHER INFORMATION: Primer 415 GOB1 5-1; alternative GSP1 for DWF
      end

<400> SEQUENCE: 47
gaataattta acttcatgac agagatg                                      27

<210> SEQ ID NO 48
<211> LENGTH: 33
<212> TYPE: DNA
<213> ORGANISM: Artificial Sequence
<220> FEATURE:
<223> OTHER INFORMATION: Degenerate 1
<220> FEATURE:
<221> NAME/KEY: misc_feature
<222> LOCATION: (24)..(24)
<223> OTHER INFORMATION: n at position 24 may be any nucleotide selected
      from G, C and A
<220> FEATURE:
<221> NAME/KEY: misc_feature
<222> LOCATION: (25)..(25)
<223> OTHER INFORMATION: n at position 25 may be any nucleotide
<220> FEATURE:
<221> NAME/KEY: misc_feature
<222> LOCATION: (26)..(26)
<223> OTHER INFORMATION: n at position 26 may be any nucleotide selected
      from G, C and A
<220> FEATURE:
<221> NAME/KEY: misc_feature
<222> LOCATION: (27)..(29)
<223> OTHER INFORMATION: n at positions 27-29 may be any nucleotide

<400> SEQUENCE: 48
acgatggact ccagagcggc cgcnnnnnng gaa                               33

<210> SEQ ID NO 49
<211> LENGTH: 33
<212> TYPE: DNA
<213> ORGANISM: Artificial Sequence
<220> FEATURE:
<223> OTHER INFORMATION: Degenerate 2
<220> FEATURE:
<221> NAME/KEY: misc_feature
<222> LOCATION: (24)..(24)
<223> OTHER INFORMATION: n at position 24 may be any nucleotide selected
      from G, C and T
<220> FEATURE:
<221> NAME/KEY: misc_feature
<222> LOCATION: (25)..(25)
<223> OTHER INFORMATION: n at position 25 may be any nucleotide
<220> FEATURE:
<221> NAME/KEY: misc_feature
<222> LOCATION: (26)..(26)
<223> OTHER INFORMATION: n at position 26 may be any nucleotide selected
      from G, C and T
<220> FEATURE:

```
<221> NAME/KEY: misc_feature
<222> LOCATION: (27)..(29)
<223> OTHER INFORMATION: n at position, 27-29 may be any nucleotide

<400> SEQUENCE: 49
acgatggact ccagagcggc cgcnnnnnng gtt                                 33

<210> SEQ ID NO 50
<211> LENGTH: 33
<212> TYPE: DNA
<213> ORGANISM: Artificial Sequence
<220> FEATURE:
<223> OTHER INFORMATION: Degenerate 3
<220> FEATURE:
<221> NAME/KEY: misc_feature
<222> LOCATION: (24)..(24)
<223> OTHER INFORMATION: n at position 24 may be any nucleotide selected
      from G, C and A
<220> FEATURE:
<221> NAME/KEY: misc_feature
<222> LOCATION: (25)..(25)
<223> OTHER INFORMATION: n at position 25 may be any nucleotide selected
      from G, C and A
<220> FEATURE:
<221> NAME/KEY: misc_feature
<222> LOCATION: (26)..(26)
<223> OTHER INFORMATION: n at position 26 may be any nucleotide
<220> FEATURE:
<221> NAME/KEY: misc_feature
<222> LOCATION: (27)..(27)
<223> OTHER INFORMATION: n at position 27 may be any nucleotide selected
      from G, C and A
<220> FEATURE:
<221> NAME/KEY: misc_feature
<222> LOCATION: (28)..(30)
<223> OTHER INFORMATION: n at position 28-30 may be any nucleotide

<400> SEQUENCE: 50
acgatggact ccagagcggc cgcnnnnnnc caa                                 33

<210> SEQ ID NO 51
<211> LENGTH: 34
<212> TYPE: DNA
<213> ORGANISM: Artificial Sequence
<220> FEATURE:
<223> OTHER INFORMATION: Degenerate 4
<220> FEATURE:
<221> NAME/KEY: misc_feature
<222> LOCATION: (24)..(24)
<223> OTHER INFORMATION: n at position 24 may be any nucleotide selected
      from G, C and T
<220> FEATURE:
<221> NAME/KEY: misc_feature
<222> LOCATION: (25)..(25)
<223> OTHER INFORMATION: n at position 25 may be any nucleotide selected
      from G, A and T
<220> FEATURE:
<221> NAME/KEY: misc_feature
<222> LOCATION: (26)..(26)
<223> OTHER INFORMATION: n at position 26 may be any nucleotide
<220> FEATURE:
<221> NAME/KEY: misc_feature
<222> LOCATION: (27)..(27)
<223> OTHER INFORMATION: n at position 27 may be any nucleotide selected
      from G, C and T
<220> FEATURE:
<221> NAME/KEY: misc_feature
<222> LOCATION: (28)..(30)
<223> OTHER INFORMATION: n at positions 28-30 may be any nucleotide

<400> SEQUENCE: 51
acgatggact ccagagcggc cgcnnnnnnn cggt                                34
```

```
<210> SEQ ID NO 52
<211> LENGTH: 16
<212> TYPE: DNA
<213> ORGANISM: Artificial Sequence
<220> FEATURE:
<223> OTHER INFORMATION: "Tail"-specific

<400> SEQUENCE: 52
acgatggact ccagag                                                        16

<210> SEQ ID NO 53
<211> LENGTH: 48
<212> TYPE: DNA
<213> ORGANISM: Artificial Sequence
<220> FEATURE:
<223> OTHER INFORMATION: Sequence Shown in Figure 4 - Adaptor Sequence
      from GenomeWalker Manual

<400> SEQUENCE: 53
gtaatacgac tcactatagg gcacgcgtgg tcgacggccc gggctggt                     48

<210> SEQ ID NO 54
<211> LENGTH: 22
<212> TYPE: DNA
<213> ORGANISM: Artificial Sequence
<220> FEATURE:
<223> OTHER INFORMATION: Sequence Shown in Figure 4 - Nested Adaptor
      Primer 1 Sequence from GenomeWalker Manual

<400> SEQUENCE: 54
gtaatacgac tcactatagg gc                                                 22

<210> SEQ ID NO 55
<211> LENGTH: 19
<212> TYPE: DNA
<213> ORGANISM: Artificial Sequence
<220> FEATURE:
<223> OTHER INFORMATION: Sequence Shown in Figure 4 - Nested Adaptor
      Primer 2 Sequence from GenomeWalker Manual

<400> SEQUENCE: 55
actatagggc acgcgtggt                                                     19
```

PLANTS COMPRISING HERBICIDE-RESISTANT EVENT SEQUENCES, PLANT MATERIALS, AND METHODS FOR DETECTION THEREOF

INCORPORATION OF SEQUENCE LISTING

The sequence listing that is contained in the file named "54936-004843US02_Sequence_Listing.txt," which is 40.2 kilobytes as measured in Windows 10 operating system and was created on Nov. 16, 2018, is filed electronically herewith and incorporated herein by reference. The sequence listing that is contained in the file named "54936.004843US02_Sequence_Listing_2.txt," which is 41.0 kilobytes as measured in Windows 10 operating system and was created on May 24, 2019, is incorporated herein by reference.

FIELD OF THE INVENTION

The invention relates to the field of plant molecular biology. More specifically, the invention relates to plant events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749, as well as to plants, plant material, and propagules comprising one of these events, and methods for detecting the presence of the events. Turfgrasses comprising Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749 possess desirable characteristics including glyphosate tolerance and enhanced turfgrass qualities, such as a shorter growth habit, darker green color and/or a thicker, fuller stand.

BACKGROUND OF THE INVENTION

Turf grasses are a well-accepted and defined class of grasses that are natural or hybridized and are used extensively in landscaping, parks, golf courses, sports playing fields, lawn tennis courts, gardens, walkpaths and the like for their unique and individualized characteristics. Among the more common turf grasses are bluegrass, rough bluegrass, ryegrass (e.g., perennial or annual), bahiagrass, bermudagrass, hybrid bermudagrass, blue grammagrass, buffalograss, carpetgrass, centipedegrass, creeping bentgrass, colonial bentgrass, fescue (e.g., fine, tall, needle-leaved, broad-leaved, etc.), kikuyugrass, orchardgrass, quackgrass, seashore paspalum, St. Augustinegrass, and zoysiagrass.

Use and appearance are prime considerations for turfgrass. To best serve a particular function, the turf should be suitable for the use for which it is intended and aesthetically appealing. It should also be well-adapted to the environment where it will be planted. Based on climatic adaptation, turfgrass species have been placed into four categories: adapted for cool humid regions, warm humid regions, cool arid regions, and warm arid regions.

Reduced vertical growth in turfgrass plants has many advantages in agriculture, including denser growth, darker green color, and less need for mowing. Levels of gibberellins (GAs), a group of tetracyclic, diterpene carboxylic acids involved in a variety of developmental processes, are commonly modified to alter plant size. GAs are plant hormones that control many aspects of plant growth and development, including stem elongation. Genes encoding enzymes related to the GA biosynthetic and metabolic pathway have been isolated and characterized in many plant species. Gibberellin 2-oxidase (GA2OX) catalyzes bioactive GAs or their immediate precursors to inactive forms. Plants comprising events that confer reduced vertical growth by expressing GA2OX are known in the art. For example, WO 2015/006774 discloses Kentucky Bluegrass plants comprising plant event Pp009-401, Pp009-415, and Pp009-469. See also, e.g., F. M. Schomburg et al., *The Plant Cell* 15:151-163 (2003); D. J. Lee and A. D. Zeevaart, *Plant Physiol* 138:243-254 (2005).

SUMMARY OF VARIOUS EMBODIMENTS OF THE INVENTION

The present invention provides constructs useful for generating transgenic events and materials and methods useful for identifying particular transgenic events that resulted in transgenic turf grass plants that are glyphosate-tolerant and that have enhanced turfgrass quality than do closely related plants that do not include the construct.

The present invention provides for glyphosate-tolerant turf grasses (e.g., St. Augustinegrass), methods of making glyphosate-tolerant turf grasses, and methods of controlling weeds in a field comprising glyphosate-tolerant turf grasses by treating the field with an effective amount of an herbicide comprising glyphosate. The invention also provides for turf grasses that have enhanced turfgrass quality (e.g., require less mowing, have a darker green color, and generate a thicker, fuller stand).

The invention provides St. Augustinegrass transgenic events designated Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749. In one aspect, the invention includes plants grown from, or obtainable from, seeds comprising events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749. The invention also includes progeny plants, seeds, or regenerable parts of plants comprising Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749. In a particular aspect, plant parts, such as tuber, crown, stem, tiller, cuttings including unrooted cuttings, rooted cuttings, and callus cuttings or callus-generated plantlets; apical meristems, pollen, ovule, flowers, shoots, stolons, propagules, seeds, runners, corms, rhizomes, roots, and leaves may comprise events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749. In another aspect, the invention provides for a St. Augustinegrass plant, cell, plant part, or seed comprising event Ss026-1819, event Ss026-1984, event Ss026-2006, event Ss026-2027, event Ss026-2050, event Ss026-2085, event Ss026-2393, event Ss026-2475, event Ss026-2623, event Ss026-2640, event Ss026-2693, event Ss026-2732, or event Ss026-2749.

With respect to identifying a plant or seed derived from a particular transgenic event, compositions and methods are provided for detecting the presence of the genomic insertion region from a novel plant comprising one or more events selected from events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749, i.e., the site in the genome where the construct resides. DNA molecules are provided that comprise at least a portion of the exogenous DNA inserted into the genome and a portion of the DNA from the plant genome flanking the insertion site (referred to herein as a "junction sequence").

In another aspect, the invention provides for DNA comprising the transgene/genomic junction regions contained in the genome of events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749. In another aspect, the invention provides for genomic DNA comprising events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749. In a particular aspect, the invention provides for an isolated DNA molecule comprising SEQ ID NOs: 1-14, the complements thereof, or combinations thereof. In another aspect, the invention provides for a plant, plant cell, plant part, or seed comprising the DNA molecule of SEQ ID NOs: 1-14, the complements thereof, or combinations thereof.

In another aspect, the invention provides for a plant, plant cell, plant part, or seed comprising a DNA molecule with at least 80%, 81%, 82%, 83%, 84%, 85%, 86%, 87%, 88%, 89%, 90%, 91%, 92%, 93%, 94%, 95%, 96%, 97%, 98%, or 99% homology to the nucleic acid sequence of SEQ ID NOs: 1-14, the complements thereof, or combinations thereof.

In a further aspect, a DNA molecule may have at least about 80%, 81%, 82%, 83%, 84%, 85%, 86%, 87%, 88%, 89%, 90%, 91%, 92%, 93%, 94%, 95%, 96%,97%, 98%, or 99% homology to the nucleic acid sequence of SEQ ID NOs: 1-14. In a further aspect, a kit may comprise a DNA molecule with at least about 80%, 81%, 82%, 83%, 84%, 85%, 86%, 87%, 88%, 89%, 90%, 91%, 92%, 93%, 94%, 95%, 96%, 97%, 98%, or 99% homology to the nucleic acid sequence of SEQ ID NOs: 1-14.

The invention also provides an expression vector comprising a nucleotide encoding a DNA molecule with at least 80%, 81%, 82%, 83%, 84%, 85%, 86%, 87%, 88%, 89%, 90%, 91%, 92%, 93%, 94%, 95%, 96%, 97%, 98%, or 99% homology to the nucleic acid sequence of SEQ ID NOs: 1-14.

In another aspect, the invention provides for a host cell comprising a DNA molecule with at least 80%, 81%, 82%, 83%, 84%, 85%, 86%, 87%, 88%, 89%, 90%, 91%, 92%, 93%, 94%, 95%, 96%, 97%, 98%, or 99% homology to the nucleic acid sequence of SEQ ID NOs: 1-14.

The invention further provides for methods of expressing a DNA molecule with at least 80%, 81%, 82%, 83%, 84%, 85%, 86%, 87%, 88%, 89%, 90%, 91%, 92%, 93%, 94%, 95%, 96%, 97%, 98%, or 99% homology to the nucleic acid sequence of SEQ ID NOs: 1-14, in a host cell and collecting the expressed polypeptide.

The invention also provides for a polypeptide encoded by a DNA molecule may have at least about 80%, 81%, 82%, 83%, 84%, 85%, 86%, 87%, 88%, 89%, 90%, 91%, 92%, 93%, 94%, 95%, 96%, 97%, 98%, or 99% homology to the nucleic acid sequence of SEQ ID NOs: 1-14.

In one aspect, the invention provides for a method of detecting the transgene/genomic junction region of events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749 in a plant. In another aspect, the invention provides for a method of detecting genomic DNA comprising events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749 in a plant. These methods may involve the use of primers or probes specific for the transgene/genomic junction of events Ss026-1819, Ss026-1984, Ss026-2050, Ss026-2085, Ss026-2393, Ss026-2475, Ss026-2623, Ss026-2640, Ss026-2693, Ss026-2693, Ss026-2732, and Ss026-2749. In a particular aspect, the invention provides for a method of detection comprising amplifying DNA from a plant, plant cell, plant part, or seed using the primers described herein. In an alternative aspect, the invention provides for a method of detection comprising hybridizing DNA from a plant, plant cell, plant part, or seed with the probes described herein.

In another aspect, the invention provides for compositions and methods for detecting the presence of a transgene/genomic junction region from St. Augustinegrass plant event Ss026-1819. DNA molecules are provided that comprise the transgene/genomic junction DNA molecule of SEQ ID NO: 1, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-1819. A St. Augustinegass plant and seed comprising event Ss026-1819 and seed are another aspect of this invention.

In another aspect, the invention provides for compositions and methods for detecting the presence of a transgene/genomic junction region from St. Augustinegrass plant event Ss026-1984. DNA molecules are provided that comprise the transgene/genomic junction DNA molecule of SEQ ID NO: 2, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-1984. A St. Augustinegass plant and seed comprising event Ss026-1984 and seed are another aspect of this invention.

In another aspect, the invention provides for compositions and methods for detecting the presence of a transgene/genomic junction region from St. Augustinegrass plant event Ss026-2006. DNA molecules are provided that comprise the transgene/genomic junction DNA molecule of SEQ ID NO: 3, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2006. A St. Augustinegass plant and seed comprising event Ss026-2006 and seed are another aspect of this invention.

In another aspect, the invention provides for compositions and methods for detecting the presence of a transgene/genomic junction region from St. Augustinegrass plant event Ss026-2027. DNA molecules are provided that comprise the transgene/genomic junction DNA molecule of SEQ ID NO: 4, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2027. A St. Augustinegass plant and seed comprising event Ss026-2027 and seed are another aspect of this invention.

In another aspect, the invention provides for compositions and methods for detecting the presence of a transgene/genomic junction region from St. Augustinegrass plant event Ss026-2050. DNA molecules are provided that comprise the transgene/genomic junction DNA molecule of SEQ ID NO: 5, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2050. A St. Augustinegass plant and seed comprising event Ss026-2050 and seed are another aspect of this invention.

In another aspect, the invention provides for compositions and methods for detecting the presence of a transgene/genomic junction region from St. Augustinegrass plant event Ss026-2085. DNA molecules are provided that comprise the transgene/genomic junction DNA molecule of SEQ ID NO: 6, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2085. A St. Augustinegass plant and seed comprising event Ss026-2085 and seed are another aspect of this invention.

In another aspect, the invention provides for compositions and methods for detecting the presence of another transgene/genomic junction region from St. Augustinegrass plant event Ss026-2085. DNA molecules are provided that comprise the transgene/genomic junction DNA molecule of SEQ ID NO: 7, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2085. A St. Augustinegass plant and seed comprising event Ss026-2085 and seed are another aspect of this invention.

In another aspect, the invention provides for compositions and methods for detecting the presence of a transgene/genomic junction region from St. Augustinegrass plant event Ss026-2393. DNA molecules are provided that comprise the transgene/genomic junction DNA molecule of SEQ ID NO: 8, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2393. A St. Augustinegass plant and seed comprising event Ss026-2393 and seed are another aspect of this invention.

In another aspect, the invention provides for compositions and methods for detecting the presence of a transgene/genomic junction region from St. Augustinegrass plant event Ss026-2475. DNA molecules are provided that comprise the transgene/genomic junction DNA molecule of SEQ ID NO: 9, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2475. A St. Augustinegass plant and seed comprising event Ss026-2475 and seed are another aspect of this invention.

In another aspect, the invention provides for compositions and methods for detecting the presence of a transgene/genomic junction region from St. Augustinegrass plant event Ss026-2623. DNA molecules are provided that comprise the transgene/genomic junction DNA molecule of SEQ ID NO: 10, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2623. A St. Augustinegass plant and seed comprising event Ss026-2623 and seed are another aspect of this invention.

In another aspect, the invention provides for compositions and methods for detecting the presence of a transgene/genomic junction region from St. Augustinegrass plant event Ss026-2640. DNA molecules are provided that comprise the transgene/genomic junction DNA molecule of SEQ ID NO: 11, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2640. A St. Augustinegass plant and seed comprising event Ss026-2640 and seed are another aspect of this invention.

In another aspect, the invention provides for compositions and methods for detecting the presence of a transgene/genomic junction region from St. Augustinegrass plant event Ss026-2693. DNA molecules are provided that comprise the transgene/genomic junction DNA molecule of SEQ ID NO: 12, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2693. A St. Augustinegass plant and seed comprising event Ss026-2693 and seed are another aspect of this invention In another aspect, the invention provides for compositions and methods for detecting the presence of a transgene/genomic junction region from St. Augustinegrass plant event Ss026-2732. DNA molecules are provided that comprise the transgene/genomic junction DNA molecule of SEQ ID NO: 13, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2732. A St. Augustinegass plant and seed comprising event Ss026-2732 and seed are another aspect of this invention.

In another aspect, the invention provides for compositions and methods for detecting the presence of a transgene/genomic junction region from St. Augustinegrass plant event Ss026-2749. DNA molecules are provided that comprise the transgene/genomic junction DNA molecule of SEQ ID NO: 14, or complements thereof, wherein the junction molecule spans the insertion site that comprises a heterologous DNA inserted into the St. Augustinegass genome and the genomic DNA from the St. Augustinegass cell flanking the insertion site in St. Augustinegass event Ss026-2749. A St. Augustinegass plant and seed comprising event Ss026-2749 and seed are another aspect of this invention.

In another aspect, the invention provides for two DNA molecules (primers) that, when used together in a DNA amplification method, produce an amplicon diagnostic for St. Augustinegrass event Ss026-1819. In one aspect, the primers are derived from SEQ ID NO: 1. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 1, or the complement thereof, and the second DNA molecule is of similar length and comprises any portion of a 5' flanking St. Augustingrass genomic DNA region of SEQ ID NO: 1, or the complement thereof. In a particular aspect, the DNA primers comprise the nucleic acid sequence of SEQ ID NO: 15 and SEQ ID NO: 16. In an alternative aspect, the invention provides for a DNA probe that, when used in a DNA hybridization method, detects St. Augustinegrass event Ss026-1819. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 1. In a particular aspect, the DNA probe comprises SEQ ID NO: 15 or SEQ ID NO: 16.

In another aspect, the invention provides for two DNA molecules (primers) that, when used together in a DNA amplification method, produce an amplicon diagnostic for St. Augustinegrass event Ss026-1984. In one aspect, the primers are derived from SEQ ID NO: 2. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 2, or the complement thereof, and the second DNA molecule is of similar length and comprises any portion of a 5' flanking St. Augustingrass genomic DNA region of SEQ ID NO: 2, or the complement thereof. In a particular aspect, the DNA primers comprise the nucleic acid sequence of SEQ ID NO: 17 and SEQ ID NO: 18. In an alternative aspect, the invention provides for a DNA probe that, when used in a DNA hybridization method, detects St. Augustinegrass event Ss026-1984. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 2. In a particular aspect, the DNA probe comprises SEQ ID NO: 17 or SEQ ID NO: 18.

In another aspect, the invention provides for two DNA molecules (primers) that, when used together in a DNA amplification method, produce an amplicon diagnostic for St. Augustinegrass event Ss026-2006. In one aspect, the primers are derived from SEQ ID NO: 3. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 3, or the complement thereof, and the second DNA molecule is of similar length and comprises any portion of a 5' flanking St. Augustingrass genomic DNA region of SEQ ID NO: 3, or the complement thereof. In a particular aspect, the DNA primers comprise the nucleic acid sequence of SEQ ID NO: 19 and SEQ ID NO: 20. In an alternative aspect, the invention provides for a DNA probe that, when used in a DNA hybridization method, detects St. Augustinegrass event Ss026-2006. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 3. In a particular aspect, the DNA probe comprises SEQ ID NO: 19 or SEQ ID NO: 20.

In another aspect, the invention provides for two DNA molecules (primers) that, when used together in a DNA amplification method, produce an amplicon diagnostic for St. Augustinegrass event Ss026-2027. In one aspect, the primers are derived from SEQ ID NO: 4. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 4, or the complement thereof, and the second DNA molecule is of similar length and comprises any portion of a 5' flanking St. Augustingrass genomic DNA region of SEQ ID NO: 4, or the complement thereof. In a particular aspect, the DNA primers comprise the nucleic acid sequence of SEQ ID NO: 21 and SEQ ID NO: 16. In an alternative aspect, the invention provides for a DNA probe that, when used in a DNA hybridization method, detects St. Augustinegrass event Ss026-2027. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 4. In a particular aspect, the DNA probe comprises SEQ ID NO: 21 or SEQ ID NO: 16.

In another aspect, the invention provides for two DNA molecules (primers) that, when used together in a DNA amplification method, produce an amplicon diagnostic for St. Augustinegrass event Ss026-2050. In one aspect, the primers are derived from SEQ ID NO: 5. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 5, or the complement thereof, and the second DNA molecule is of similar length and comprises any portion of a 5' flanking St. Augustingrass genomic DNA region of SEQ ID NO: 5, or the complement thereof. In a particular aspect, the DNA primers comprise the nucleic acid sequence of SEQ ID NO: 22 and SEQ ID NO: 20. In an alternative aspect, the invention provides for a DNA probe that, when used in a DNA hybridization method, detects St. Augustinegrass event Ss026-2050. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 5. In a particular aspect, the DNA probe comprises SEQ ID NO: 22 or SEQ ID NO: 20.

In another aspect, the invention provides for two DNA molecules (primers) that, when used together in a DNA amplification method, produce an amplicon diagnostic for St. Augustinegrass event Ss026-2085. In one aspect, the primers are derived from SEQ ID NO: 6. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 6, or the complement thereof, and the second DNA molecule is of similar length and comprises any portion of a 5' flanking St. Augustingrass genomic DNA region of SEQ ID NO: 6, or the complement thereof. In a particular aspect, the DNA primers comprise the nucleic acid sequence of SEQ ID NO: 23 and SEQ ID NO: 20. In an alternative aspect, the invention provides for a DNA probe that, when used in a DNA hybridization method, detects St. Augustinegrass event Ss026-2085. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 6. In a particular aspect, the DNA probe comprises SEQ ID NO: 23 or SEQ ID NO: 20.

In another aspect, the invention provides for two DNA molecules (primers) that, when used together in a DNA amplification method, produce ANOTHER amplicon diagnostic for St. Augustinegrass event Ss026-2085. In one aspect, the primers are derived from SEQ ID NO: 7. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 7, or the complement thereof, and the second DNA molecule is of similar length and comprises any portion of a 5' flanking St. Augustingrass genomic DNA region of SEQ ID NO: 7, or the complement thereof. In a particular aspect, the DNA primers comprise the nucleic acid sequence of SEQ ID NO: 24 and SEQ ID NO: 25. In an alternative aspect, the invention provides for a DNA probe that, when used in a DNA hybridization method, detects St. Augustinegrass event Ss026-2085. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 7. In a particular aspect, the DNA probe comprises SEQ ID NO: 24 or SEQ ID NO: 25.

In another aspect, the invention provides for two DNA molecules (primers) that, when used together in a DNA amplification method, produce an amplicon diagnostic for St. Augustinegrass event Ss026-2393. In one aspect, the primers are derived from SEQ ID NO: 8. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 8, or the complement thereof, and the second DNA molecule is of similar length and comprises any portion of a 5' flanking St. Augustingrass genomic DNA region of SEQ ID NO: 8, or the complement thereof. In a particular aspect, the DNA primers comprise the nucleic acid sequence of SEQ ID NO: 26 and SEQ ID NO: 20. In an alternative aspect, the invention provides for a DNA probe that, when used in a DNA hybridization method, detects St. Augustinegrass event Ss026-2393. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 8. In a particular aspect, the DNA probe comprises SEQ ID NO: 26 or SEQ ID NO: 20.

In another aspect, the invention provides for two DNA molecules (primers) that, when used together in a DNA amplification method, produce an amplicon diagnostic for St. Augustinegrass event Ss026-2475. In one aspect, the primers are derived from SEQ ID NO: 9. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 9, or the complement thereof, and the second DNA molecule is of similar length and comprises any portion of a 5' flanking St. Augustingrass genomic DNA region of SEQ ID NO: 9, or the complement thereof. In a particular aspect, the DNA primers comprise the nucleic acid sequence of SEQ ID NO: 27 and SEQ ID NO: 28. In an alternative aspect, the invention provides for a DNA probe that, when used in a DNA hybridization method, detects St. Augustinegrass event Ss026-2475. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 9. In a particular aspect, the DNA probe comprises SEQ ID NO: 27 or SEQ ID NO: 28.

In another aspect, the invention provides for two DNA molecules (primers) that, when used together in a DNA amplification method, produce an amplicon diagnostic for St. Augustinegrass event Ss026-2623. In one aspect, the primers are derived from SEQ ID NO: 10. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 10, or the complement thereof, and the second DNA molecule is of similar length and comprises any portion of a 5' flanking St. Augustingrass genomic DNA region of SEQ ID NO: 10, or the complement thereof. In a particular aspect, the DNA primers comprise the nucleic acid sequence of SEQ ID NO: 29 and SEQ ID NO: 30. In an alternative aspect, the invention provides for a DNA probe that, when used in a DNA hybridization method, detects St. Augustinegrass event Ss026-2623. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 10 In a particular aspect, the DNA probe comprises SEQ ID NO: 29 or SEQ ID NO: 30.

In another aspect, the invention provides for two DNA molecules (primers) that, when used together in a DNA amplification method, produce an amplicon diagnostic for St. Augustinegrass event Ss026-2640. In one aspect, the primers are derived from SEQ ID NO: 11. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 11, or the complement thereof, and the second DNA molecule is of similar length and comprises any portion of a 5' flanking St. Augustingrass genomic DNA region of SEQ ID NO: 11, or the complement thereof. In a particular aspect, the DNA primers comprise the nucleic acid sequence of SEQ ID NO: 31 and SEQ ID NO: 18. In an alternative aspect, the invention provides for a DNA probe that, when used in a DNA hybridization method, detects St. Augustinegrass event Ss026-2640. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 11. In a particular aspect, the DNA probe comprises SEQ ID NO: 31 or SEQ ID NO: 18.

In another aspect, the invention provides for two DNA molecules (primers) that, when used together in a DNA amplification method, produce an amplicon diagnostic for St. Augustinegrass event Ss026-2693. In one aspect, the primers are derived from SEQ ID NO: 12. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 12, or the complement thereof, and the second DNA molecule is of similar length and comprises any portion of a 5' flanking St. Augustingrass genomic DNA region of SEQ ID NO: 12, or the complement thereof. In a particular aspect, the DNA primers comprise the nucleic acid sequence of SEQ ID NO: 32 and SEQ ID NO: 33. In an alternative aspect, the invention provides for a DNA probe that, when used in a DNA hybridization method, detects St. Augustinegrass event Ss026-2693. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 12. In a particular aspect, the DNA probe comprises SEQ ID NO: 32 or SEQ ID NO: 33.

In another aspect, the invention provides for two DNA molecules (primers) that, when used together in a DNA amplification method, produce an amplicon diagnostic for St. Augustinegrass event Ss026-2732. In one aspect, the primers are derived from SEQ ID NO: 13. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 13, or the complement thereof, and the second DNA molecule is of similar length and comprises any portion of a 5' flanking St. Augustingrass genomic DNA region of SEQ ID NO: 13, or the complement thereof. In a particular aspect, the DNA primers comprise the nucleic acid sequence of SEQ ID NO: 34 and SEQ ID NO: 18. In an alternative aspect, the invention provides for a DNA probe that, when used in a DNA hybridization method, detects St. Augustinegrass event Ss026-2732. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 13. In a particular aspect, the DNA probe comprises SEQ ID NO: 34 or SEQ ID NO: 18.

In another aspect, the invention provides for two DNA molecules (primers) that, when used together in a DNA amplification method, produce an amplicon diagnostic for St. Augustinegrass event Ss026-2749. In one aspect, the primers are derived from SEQ ID NO: 14. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 14, or the complement thereof, and the second DNA molecule is of similar length and comprises any portion of a 5' flanking St. Augustingrass genomic DNA region of SEQ ID NO: 14, or the complement thereof. In a particular aspect, the DNA primers comprise the nucleic acid sequence of SEQ ID NO: 35 and SEQ ID NO: 18. In an alternative aspect, the invention provides for a DNA probe that, when used in a DNA hybridization method, detects St. Augustinegrass event Ss026-2749. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 14. In a particular aspect, the DNA probe comprises SEQ ID NO: 35 or SEQ ID NO: 18.

In one embodiment of the invention, the primer pair or probe may be attached to a solid support. In another embodiment, the solid support may be a bead, fiber, plate, or multi-well plate. In another embodiment, the primer pair or probe may be arranged in an array. In another embodiment, the kit may further comprise a buffer or solution. In another embodiment, the primer pair or probe may be labeled. In another embodiment, the label may be a florescent molecule, a radioactive isotope, ligand, chemifluorescent, chemiluminescent agent, or enzyme.

In another embodiment of the invention, a kit may comprise the primer pair or probe of SEQ ID NO: 15 and/or SEQ ID NO: 16, In another embodiment, a kit may comprise the primer pair or probe of of SEQ ID NO: 17 and/or SEQ ID NO: 18. In another embodiment, a kit may comprise the primer pair or probe of SEQ ID NO: 19 and/or SEQ ID NO: 20. In another embodiment, a kit may comprise the primer pair or probe of SEQ ID NO: 21 and/or SEQ ID NO: 16. In another embodiment, a kit may comprise the primer pair or probe of SEQ ID NO: 22 and/or SEQ ID NO: 20. In another embodiment, a kit may comprise the primer pair or probe of SEQ ID NO: 23 and/or SEQ ID NO: 20. In another embodiment, a kit may comprise the primer pair or probe of SEQ ID NO: 24 and/or SEQ ID NO: 25. In another embodiment, a kit may comprise the primer pair or probe of SEQ ID NO: 26 and/or SEQ ID NO: 20. In another embodiment, a kit may comprise the primer pair or probe of SEQ ID NO: 27 and/or SEQ ID NO: 28. In another embodiment, a kit may comprise the primer pair or probe of SEQ ID NO: 29 and/or SEQ ID NO: 30. In another embodiment, a kit may comprise the primer pair or probe of SEQ ID NO: 31 and/or SEQ ID NO: 18. In another embodiment, a kit may comprise the primer pair or probe of SEQ ID NO: 32 and/or SEQ ID NO: 33. In another embodiment, a kit may comprise the primer pair or probe of SEQ ID NO: 34 and/or SEQ ID NO: 18. In another embodiment, a kit may comprise the primer pair or probe of SEQ ID NO: 35 and/or SEQ ID NO: 18.

In another aspect, the invention provides for methods of detecting the presence of DNA corresponding specifically to the St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749 DNA in a sample. These methods comprise: (a) contacting a DNA sample with a primer pair that, when used in a nucleic acid amplification reaction with genomic DNA from St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 produces an amplicon diagnostic for St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749; (b) performing a nucleic acid amplification reaction, thereby producing the amplicon; and (c) detecting the amplicon. In yet another aspect, the methods comprise: (a) contacting a DNA sample with a probe that hybridizes, under stringent hybridization conditions, with genomic DNA from St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749; (b) subjecting the sample and probe to stringent hybridization conditions; and (c) detecting hybridization of the probe to the Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 DNA.

In another aspect, the invention provides for methods of producing a St. Augustinegrass plant that tolerates application of glyphosate comprising sexually crossing a first parental St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 and a second parental plant (e.g., St. Augustinegrass) that lacks Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 (or that lacks glyphosate tolerance), thereby producing a plurality of progeny plants. In another aspect, the methods comprise: (a) sexually crossing a first parental St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 and a second parental plant (e.g., St. Augustinegrass) that lacks Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 (or that lacks glyphosate tolerance), thereby producing a plurality of progeny plants; and (b) selecting a progeny plant that tolerates application of glyphosate. Such methods may optionally comprise the further step of back-crossing the progeny plant to the second parental St. Augustinegrass plant and selecting for glyphosate-tolerant progeny to produce a true-breeding St. Augustinegrass variety that tolerates application of glyphosate.

In another aspect, the invention provides for a turfgrass stand, lawn, sports field, or golf course comprising event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749. In another aspect, the invention provides for a method of controlling weeds in a turfgrass stand of St. Augustinegrass Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749 comprising the step of applying a glyphosate-containing herbicide formulation to the turfgrass stand.

In another embodiment, the invention provides for methods of producing a St. Augustinegrass plant that tolerates application of glyphosate comprising sexually crossing a first parental St. Augustinegrass comprising the EPSPS transgene nucleic acid (SEQ ID NO: 36) or the EPSPS-containing expression cassette (SEQ ID NO: 37) and a second parental plant (e.g., St. Augustinegrass) that lacks the nucleic acid of SEQ ID NO: 36 or SEQ ID NO: 37 (or that lacks glyphosate tolerance), thereby producing a plurality of progeny plants.

In another embodiment, the invention provides for methods of producing a St. Augustinegrass plant that tolerates application of glyphosate comprising: (a) sexually crossing a first parental St. Augustinegrass the nucleic acid of SEQ ID NO: 36 or SEQ ID NO: 37 and a second parental plant (e.g., St. Augustinegrass) that lacks the nucleic acid of SEQ ID NO: 36 or SEQ ID NO: 37 (or that lacks glyphosate tolerance), thereby producing a plurality of progeny plants; and (b) selecting a progeny plant that tolerates application of glyphosate. Such methods may optionally comprise the further step of back-crossing the progeny plant to the second parental St. Augustinegrass plant and selecting for glyphosate-tolerant progeny to produce a true-breeding St. Augustinegrass variety that tolerates application of glyphosate.

In another embodiment, the invention provides for a turfgrass stand, lawn, sports field, or golf course comprising the nucleic acid of SEQ ID NO: 36 or SEQ ID NO: 37. In another embodiment, the invention provides for a method of controlling weeds in a turfgrass stand of St. Augustinegrass the nucleic acid of SEQ ID NO: 36 or SEQ ID NO: 37 comprising the step of applying a glyphosate containing herbicide formulation to the turfgrass stand.

In another embodiment, the method for producing St. Augustinegrass plant or seed may comprise selfing or crossing a St. Augustinegrass plant comprising event Ss026-1819, event Ss026-1984, event Ss026-2006, event Ss026-2027, event Ss026-2050, event Ss026-2085, event Ss026-2393, event Ss026-2475, event Ss026-2623, event Ss026-2640, event Ss026-2693, event Ss026-2732, and/or event Ss026-2749 with a plant lacking event Ss026-1819, event Ss026-1984, event Ss026-2006, event Ss026-2027, event Ss026-2050, event Ss026-2085, event Ss026-2393, event Ss026-2475, event Ss026-2623, event Ss026-2640, event Ss026-2693, event Ss026-2732, and/or event Ss026-2749, and planting seed obtained from said cross.

In another embodiment, the invention provides for methods of producing a St. Augustinegrass plant that exhibits enhanced turfgrass qualities (e.g., darker green color and/or a thicker, fuller stand) comprising sexually crossing a first parental St. Augustinegrass comprising the GA2OX transgene nucleic acid (SEQ ID NO: 38) or the GA2OX-containing expression cassette (SEQ ID NO: 39) and a second parental plant (e.g., St. Augustinegrass) that lacks the nucleic acid of SEQ ID NO: 38 or SEQ ID NO: 39 (or that lacks enhanced turfgrass qualities conferred by the short growth-habit trait), thereby producing a plurality of progeny plants.

In another embodiment, the invention provides for methods of producing a St. Augustinegrass plant that exhibits enhanced turfgrass qualities (e.g., darker green color and/or a thicker, fuller stand) comprising: (a) sexually crossing a first parental St. Augustinegrass the nucleic acid of SEQ ID NO: 37 or SEQ ID NO: 39 and a second parental plant (e.g., St. Augustinegrass) that lacks the nucleic acid of SEQ ID NO: 37 or SEQ ID NO: 39 (or that lacks enhanced turfgrass qualities conferred by the short growth-habit trait), thereby producing a plurality of progeny plants; and (b) selecting a progeny plant that exhibits enhanced turfgrass qualities. Such methods may optionally comprise the further step of back-crossing the progeny plant to the second parental St. Augustinegrass plant and selecting for progeny exhibiting enhanced turfgrass qualities to produce a true-breeding St. Augustinegrass variety that exhibits enhanced turfgrass qualities.

In another embodiment, the invention provides for a turfgrass stand, lawn, sports field, or golf course comprising the nucleic acid of SEQ ID NO: 36, SEQ ID NO: 37, SEQ ID NO: 38, and/or SEQ ID NO: 39. In another embodiment, the invention provides for a method of controlling weeds in a turfgrass stand of St. Augustinegrass harboring the nucleic acid of SEQ ID NO: 36 or SEQ ID NO: 37, comprising the step of applying a glyphosate-containing herbicide formulation to the turfgrass stand. In another embodiment, the invention provides for a method of enhancing the qualities in a turfgrass stand of St. Augustinegrass harboring the nucleic acid of SEQ ID NO: 38 or SEQ ID NO: 39, comprising the step of selectively screening turfgrass plants for enhanced turgrass qualities (e.g., darker green color and/or a thicker, fuller stand).

In one embodiment, the invention provides a nucleic acid comprising the nuclotide sequence of SEQ ID NO: 36, SEQ ID NO: 37, SEQ ID NO: 38, or SEQ ID NO: 39. In another embodiment, the invention provides for an isolated plasmid comprising the nucleotide sequence of SEQ ID NO: 36, SEQ ID NO: 37, SEQ ID NO: 38, or SEQ ID NO: 39. In another embodiment, the invention provides for an isolated cell comprising the nucleotide sequence of SEQ ID NO: 36, SEQ ID NO: 37, SEQ ID NO: 38, or SEQ ID NO: 39. In some embodiments, the cell is a bacterial cell or a plant cell.

In another embodiment, the invention provides for a St. Augustinegrass plant, cell, plant part, or seed comprising the nucleotide sequence of SEQ ID NO: 36, SEQ ID NO: 37, SEQ ID NO: 38, or SEQ ID NO: 39. In some embodiments, the plant part may be a cell, tuber, crown, stem, tiller, cuttings including un-rooted cuttings, rooted cuttings, and callus cuttings or callus-generated plantlets; apical meristems, pollen, ovule, flower, shoot, stolon, propagule, seed, runner, corm, rhizome, root, or leaf.

In another embodiment, the invention provides for a turfgrass stand, lawn, sports field, or golf course comprising plants comprising the nucleotide sequence SEQ ID NO: 36, SEQ ID NO: 37, SEQ ID NO: 38, or SEQ ID NO: 39. In some embodiments, the plants include St. Augustinegrass.

In another embodiment, the invention provides for a method of producing a St. Augustinegrass plant or seed, the method comprising growing a seed comprising the nucleotide sequence of SEQ ID NO: 36, SEQ ID NO: 37, SEQ ID NO: 38, or SEQ ID NO: 39.

In another embodiment, the invention provides for a method for controlling weeds in a field, the method comprising growing a seed comprising the nucleotide sequence SEQ ID NO: 36, SEQ ID NO: 37, SEQ ID NO: 38, and/or SEQ ID NO: 39, and treating the field with an effective amount of an herbicide comprising glyphosate.

In another embodiment, the invention provides for a method of producing a St. Augustinegrass plant that tolerates application of glyphosate, the method comprising sexually crossing a first parental St. Augustinegrass comprising the nucleic acid of SEQ ID NO: 36 or SEQ ID NO: 37 and a second parental plant lacking the nucleic acid of SEQ ID NO: 38 or SEQ ID NO: 39 or lacking glyphosate tolerance, thereby producing a plurality of progeny plants. In some embodiments, the method may further comprise selecting a progeny plant that tolerates application of glyphosate. In some embodiments, the method may further comprise backcrossing the progeny plant to the second parental St. Augustinegrass plant and selecting for glyphosate-tolerant progeny to produce a true-breeding St. Augustinegrass variety that tolerates application of glyphosate.

In another embodiment, the invention provides for a method of controlling weeds in a turfgrass stand of St. Augustinegrass comprising the nucleic acid of SEQ ID NO: 36 or SEQ ID NO: 37, the method comprising the step of applying a glyphosate-containing herbicide formulation to the turfgrass stand.

The foregoing and other aspects of the invention will become more apparent from the following detailed description and accompanying drawings.

BRIEF DESCRIPTION OF THE SEQUENCES

Figure 1:
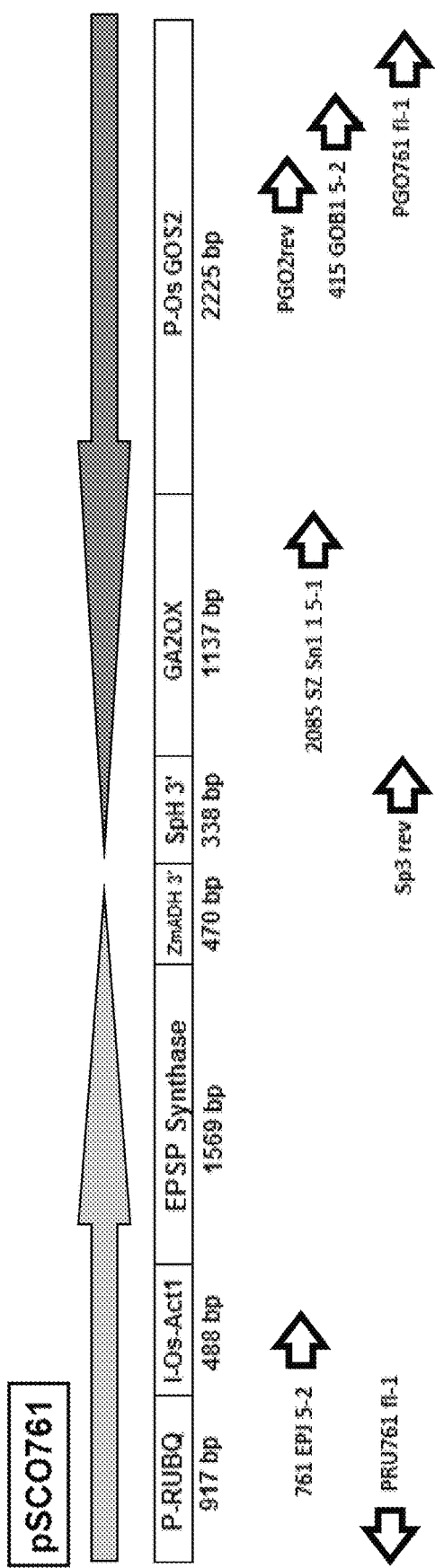
FIG. 1 depicts a map of the pSCO761 transgene, containing the EPSP synthase cassette and the GA2OX cassette. The shaded arrows above the map indicate the orientations of transcription of each gene. Arrows below the map indicate the location of sequence identity, and orientation, of transgene-specific oligonucleotides used as primers in identifying flanking sequences unique to each transgenic event.

SEQ ID NO: 1 is 1819 ZS Sn 1, a 1114 nucleotide sequence representing the junction region of a genomic DNA sequence and an integrated transgenic expression cassette (positions 2669 through 3532 of SEQ ID NO: 39) in St. Augustinegrass event Ss026-1819.

SEQ ID NO: 2 is 1984 RU FNS 1, a 230 nucleotide sequence representing the junction region of a genomic DNA sequence and an integrated transgenic expression cassette (positions 4 through 132 of SEQ ID NO: 37) in St. Augustinegrass event Ss026-1984.

SEQ ID NO: 3 is 2006 TAIL GO 1, a 669 nucleotide sequence representing the junction region of a genomic DNA sequence and an integrated transgenic expression cassette (positions 8 through 141 of SEQ ID NO: 39) in St. Augustinegrass event Ss026-2006.

SEQ ID NO: 4 is 2027 ZS 2, a 482 nucleotide sequence representing the junction region of a genomic DNA sequence and an integrated transgenic expression cassette (positions3085 through 3532 of SEQ ID NO: 39) in St. Augustinegrass event Ss026-2027.

SEQ ID NO: 5 is 2050 TAIL GO 1, a 790 nucleotide sequence representing the junction region of a genomic DNA sequence and an integrated transgenic expression cassette (positions 48 through 141 of SEQ ID NO: 39) in St. Augustinegrass event Ss026-2050.

SEQ ID NO: 6 is 2085 GO Sn 1, a 678 nucleotide sequence representing the junction region of a genomic DNA sequence and an integrated transgenic expression cassette (positions 34 through 141 of SEQ ID NO: 39) in St. Augustinegrass event Ss026-2085.

SEQ ID NO: 7 is 2085 SZ Sn 1, a 358 nucleotide sequence representing the junction region of a genomic DNA sequence and an integrated transgenic expression cassette (positions 2299 through 2474 of SEQ ID NO: 39) in St. Augustinegrass event Ss026-2085.

SEQ ID NO: 8 is 2393 GO Sn 1, a 551 nucleotide sequence representing the junction region of a genomic DNA sequence and an integrated transgenic expression cassette (positions 6 through 141 of SEQ ID NO: 39) in St. Augustinegrass event Ss026-2393.

SEQ ID NO: 9 is 2475 TAIL GO 1, a 571 nucleotide sequence representing the junction region of a genomic DNA sequence and an integrated transgenic expression cassette (positions 5 through 266 of SEQ ID NO: 39) in St. Augustinegrass event Ss026-2475.

SEQ ID NO: 10 is 2623 TAIL GOBI 1-3, a 345 nucleotide sequence representing the junction region of a genomic DNA sequence and an integrated transgenic expression cassette (positions 1128 through 1228 of SEQ ID NO: 37) in St. Augustinegrass event Ss026-2623.

SEQ ID NO: 11 is 2640 RU Fs 1, a 572 nucleotide sequence representing the junction region of a genomic DNA sequence and an integrated transgenic expression cassette (positions 7 through 132 of SEQ ID NO: 37) in St. Augustinegrass event Ss026-2640.

SEQ ID NO: 12 is 2693 RU Sn 1, a 358 nucleotide sequence representing the junction region of a genomic DNA sequence and an integrated transgenic expression cassette (positions 382 through 723 of SEQ ID NO: 39) in St. Augustinegrass event Ss026-2693.

SEQ ID NO: 13 is 2732 RU Fs 1, a 683 nucleotide sequence representing the junction region of a genomic DNA sequence and an integrated transgenic expression cassette (positions 7 through 132 of SEQ ID NO: 37) in St. Augustinegrass event Ss026-2732.

SEQ ID NO: 14 is 2749 RUrev468 1-2, a 172 nucleotide sequence representing the junction region of a genomic DNA sequence and an integrated transgenic expression cassette (positions 95 through 132 of SEQ ID NO: 37) in St. Augustinegrass event Ss026-2749.

SEQ ID NO: 15 is primer 1819 RU Sn 1 3-1, used in combination with SEQ ID NO: 16 to identify the genomic/transgene junction 1819 ZS Sn 1 in St. Augustinegrass event Ss026-1819.

SEQ ID NO: 16 is primer Sp3 rev, used in combination with SEQ ID NO: 15 to identify the genomic/transgene junction 1819 ZS Sn 1 in St. Augustinegrass event Ss026-1819, also used in combination with SEQ ID NO: 21 to identify the genomic/transgene junction 2027 ZS 2 in St. Augustinegrass event Ss026-2027.

SEQ ID NO: 17 is primer 1984 RU FNS 3-2, used in combination with SEQ ID NO: 18 to identify the genomic/transgene junction 1984 RU FNS 1 in St. Augustinegrass event Ss026-1984.

SEQ ID NO: 18 is primer PRU761 fl-1, used in combination with SEQ ID NO: 17 to identify the genomic/transgene junction 1984 RU FNS in St. Augustinegrass event Ss026-1984, also used in combination with SEQ ID NO: 31 to identify the genomic/transgene junction 2640 RU Fs 1 in St. Augustinegrass event Ss026-2640, also used in combination with SEQ ID NO: 34 to identify the genomic/transgene junction 2732 RU Fs 1 in St. Augustinegrass event Ss026-2732, and also used in conjunction with SEQ ID NO: 35 to identify the genomic/transgene junction 2749 RUrev468 1-2 in St. Augustinegrass event Ss026-2749.

SEQ ID NO: 19 is primer 2006 TAIL GO 1 3-1, used in combination with SEQ ID NO: 20 to identify the genomic/transgene junction 2006 TAIL GO 1 in St. Augustinegrass event Ss026-2006.

SEQ ID NO: 20 is PGO761 fl-1, used in combination with SEQ ID NO: 19 to identify the genomic/transgene junction 2006 TAIL GO 1 in St. Augustinegrass event Ss026-2006, also used in combination with SEQ ID NO: 22 to identify the genomic/transgene junction 2050 TAIL GO 1 in St. Augustinegrass event Ss026-2050, also used in combination with SEQ ID NO: 23 to identify the genomic/transgene junction 2085 GO Sn 1 in St. Augustinegrass event Ss026-2085, also used in combination with SEQ ID NO: 26 to identify the genomic/transgene junction 2393 GO Sn 1 in St. Augustinegrass event Ss026-2393.

SEQ ID NO: 21 is primer 2027 ZS2 3-1, used in combination with SEQ ID NO: 16 to identify the genomic/transgene junction 2027 ZS 2 in St. Augustinegrass event Ss026-2027.

SEQ ID NO: 22 is primer 2050 TAIL GO 1 3-2, used in combination with SEQ ID NO: 20 to identify the genomic/transgene junction 2050 TAIL GO 1 in St. Augustinegrass event Ss026-2050.

SEQ ID NO: 23 primer 2085 GO Sn 1 3-2, used in combination with SEQ ID NO: 20 to identify the genomic/transgene junction 2085 GO Sn 1 in St. Augustinegrass event Ss026-2085.

SEQ ID NO: 24 is primer 2085 SZ Sn 1 3-2, used in combination with SEQ ID NO: 25 to identify the genomic/transgene junction 2085 SZ Sn 1 in St. Augustinegrass event Ss026-2085.

SEQ ID NO: 25 is primer 2085 SZ Sn 1 5-1, used in combination with SEQ ID NO: 24 to identify the genomic/transgene junction 2085 SZ Sn 1 in St. Augustinegrass event Ss026-2085.

SEQ ID NO: 26 is primer 2393 GO Sn 1 3-2, used in combination with SEQ ID NO: 20 to identify the genomic/transgene junction 2393 GO Sn 1 in St. Augustinegrass event Ss026-2393.

SEQ ID NO: 27 is primer 2475 TAIL GO 1 3-2, used in combination with SEQ ID NO: 28 to identify the genomic/transgene junction 2475 TAIL GO 1 in St. Augustinegrass event Ss026-2475.

SEQ ID NO: 28 is primer 415 GOBI 5-2, used in combination with SEQ ID NO: 27 to identify the genomic/transgene junction 2475 TAIL GO 1 in St. Augustinegrass event Ss026-2475.

SEQ ID NO: 29 is primer 2623 GOBI LAD1-3 D, used in combination with SEQ ID NO: 30 to identify the genomic/transgene junction 2623 TAIL GOBI 1-3 in St. Augustinegrass event Ss026-2623.

SEQ ID NO: 30 is primer 761 EPJ 5-2, used in combination with SEQ ID NO: 29 to identify the genomic/transgene junction 2623 TAIL GOBI 1-3 in St. Augustinegrass event Ss026-2623.

SEQ ID NO: 31 is primer 2640 RU Fs 1 3-1, used in combination with SEQ ID NO: 18 to identify the genomic/transgene junction 2640 RU Fs 1 in St. Augustinegrass event Ss026-2640.

SEQ ID NO: 32 is primer 2693 RU Sn 1 3-5, used in combination with SEQ ID NO: 33 to identify the genomic/transgene junction 2693 RU Sn 1 in St. Augustinegrass event Ss026-2693.

SEQ ID NO: 33 is primer PRU761 fl-1, used in combination with SEQ ID NO: 32 to identify the genomic/transgene junction 2693 RU Sn 1 in St. Augustinegrass event Ss026-2693.

SEQ ID NO: 34 is primer 2732 RU Fs 1 3-2, used in combination with SEQ ID NO: 18 to identify the genomic/transgene junction 2732 RU Fs 1 in event Ss026-2732.

SEQ ID NO: 35 is primer 2749 RU468 1-2 3-3, used in combination with SEQ ID NO: 18 to identify the genomic/transgene junction 2749 RUrev468 1-2 in event Ss026-2749.

SEQ ID NO: 36 is a 1569 nucleotide sequence representing the transgene (cDNA) for a variant of the enzyme 5-enolpyruvyl-3-phosphoshikimate synthase (EPSPS).

SEQ ID NO: 37 is a 3446 nucleotide sequence representing the transgene (cDNA) of the enzyme 5-enolpyruvyl-3-phosphoshikimate synthase (EPSPS) expression cassette.

SEQ ID NO: 38 is a 1137 nucleotide sequence representing the transgene (cDNA) for Gibberellic Acid 2-Oxidase (GA2OX).

SEQ ID NO: 39 is a 3696 nucleotide sequence representing the transgene (cDNA) of the Gibberellic Acid 2-Oxidase (GA2OX) expression cassette.

SEQ ID NO: 40 is a transgene-specific primer PRU761 fl-2 (37) homologous to the EPSPS end from positions 29-56 of SEQ ID NO: 37, used for both GenomeWalker™ and TAIL-PCR methods for cloning flanking sequences.

SEQ ID NO: 41 is a transgene-specific primer PGO761 fl-2 (38) homologous to the GA2OX end from positions 67-103 of SEQ ID NO: 39, used for both GenomeWalker™ and TAIL-PCR methods for cloning flanking sequences.

SEQ ID NO: 42 is a transgene-specific primer ZD fwd (39) homologous to a portion of the 3'UTR of the EPSPS cassette from positions 3142-3173 of SEQ ID NO: 37, used for both GenomeWalker™ and TAIL-PCR methods for cloning flanking sequences under the scenario of a truncated transgene insertion.

SEQ ID NO: 43 is a transgene-specific primer Sp3fwd (40) homologous to a portion of the 3'UTR of the GA2OX cassette from positions 3499-3532 of SEQ ID NO: 39, used for both GenomeWalker™ and TAIL-PCR methods for cloning flanking sequences under the scenario of a truncated transgene insertion.

SEQ ID NO: 44 is a transgene-specific primer ZDrev (41) homologous to a portion of the 3'UTR of the EPSPS cassette from positions 3142-3173 of SEQ ID NO: 37, used for both GenomeWalker™ and TAIL-PCR methods for cloning flanking sequences, under the scenario of a truncated transgene insertion.

SEQ ID NO: 45 is a transgene-specific primer PRUrev608 homologous to a promoter region of the EPSPS cassette from positions 579-608 of SEQ ID NO: 37, used for both GenomeWalker™ and TAIL-PCR methods for cloning flanking sequences, under the scenario of an insertion with a truncated EPSPS promoter.

SEQ ID NO: 46 is a transgene-specific primer ("GSP") PRUrev468 homologous to a promoter region of the EPSPS cassette from positions 450-483 of SEQ ID NO: 37, used for both GenomeWalker™ and TAIL-PCR methods for cloning flanking sequences, under the scenario of an insertion with a truncated EPSPS promoter.

SEQ ID NO: 47 is a transgene-specific primer 415 GOBI 5-1 homologous to a promoter region of the GA2OX cassette from positions 267-294 of SEQ ID NO: 39, used for both GenomeWalker™ and TAIL-PCR methods for cloning flanking sequences, under the scenario of an insertion with a truncated GA2OX promoter.

SEQ ID NO: 48 is a degenerate primer LAD1-1 used for the TAIL-PCR method for cloning flanking sequences; wherein positions 24 and 26 may be occupied by G, C or A; and positions 25, 27, 28, and 29 may be occupied by any nucleotide.

SEQ ID NO: 49 is a degenerate primer LAD1-2 used for the TAIL-PCR method for cloning flanking sequences; wherein positions 24 and 26 may be occupied by G, C, or T, and positions 25, 27, 28, and 29 may be occupied by any nucleotide.

SEQ ID NO: 50 is a degenerate primer LAD1-3 used for the TAIL-PCR method for cloning flanking sequences; wherein positions 24, 25, and 27 may be occupied by G, C, or A, and positions 26, 28, 29, and 30 may be occupied by any nucleotide.

SEQ ID NO: 51 is a degenerate primer LAD1-4 used for the TAIL-PCR method for cloning flanking sequences; wherein positions 24 and 27 may be occupied by G, C, or T, position 25 may be occupied by G, A, or T, and positions 26, 28, 29 and 30 may be occupied by any nucleotide.

SEQ ID NO: 52 is a primer AC1 which is specific for the first 15 nucleotides of conserved sequence in all four LAD degenerate primers (SEQ ID NOs: 48-51), and which is used for the TAIL-PCR method for cloning flanking sequences.

DETAILED DESCRIPTION OF PREFERRED EMBODIMENTS OF THE INVENTION

The invention provides St. Augustinegrass plant events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749, turfgrasses, plants, seeds, and plant material comprising these events, and methods for detecting the presence of the events. Turfgrass plants comprising events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 possess desirable characteristics, including glyphosate tolerance and enhanced turfgrass quality.

In addition, the invention provides plants, tubers, crowns, stems, tillers, cuttings (including un-rooted cuttings, rooted cuttings, and callus cuttings), and callus-generated plantlets; apical meristems, pollen, ovules, flowers, shoots, stolons, propagules, seeds, runners, corms, rhizomes, roots, leaves, and plant material comprising a variant enzyme 5-enolpyruvyl-3-phosphoshikimate synthase (EPSP synthase) transgene, as well as methods for detecting the presence of the variant EPSP synthase transgene. Plants comprising the variant EPSP synthase transgene possess glyphosate tolerance.

In addition, the invention provides plants, tubers, crowns, stems, tillers, cuttings (including un-rooted cuttings, rooted cuttings, and callus cuttings), and callus-generated plantlets; apical meristems, pollen, ovules, flowers, shoots, stolons, propagules, seeds, runners, corms, rhizomes, roots, leaves, and plant material comprising a gibberellic acid 2-oxidase (GA2OX) transgene and variant EPSP synthase transgene, as well as methods for detecting the presence of the GA2OX transgene or variant EPSP synthase transgene. Plants comprising the variant GA2OX transgene exhibit enhanced turfgrass quality, such as shorter stature, darker green color, thicker/more density, shorter stolons, better nutrient use efficiency, and better water use efficiency.

In addition, the invention provides plants, tubers, crowns, stems, tillers, cuttings (including un-rooted cuttings, rooted cuttings, and callus cuttings), and callus-generated plantlets; apical meristems, pollen, ovules, flowers, shoots, stolons, propagules, seeds, runners, corms, rhizomes, roots, leaves, and plant material comprising a variant enzyme 5-enolpyruvyl-3-phosphoshikimate synthase (EPSP synthase) transgene and a gibberellic acid 2-oxidase (GA2OX)

transgene, as well as methods for detecting the presence of the EPSP synthase and/or GA2OX transgenes.

Definitions

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR 1.822 is used.

As used herein, the term "isolated" refers to at least partially separating a molecule from other molecules normally associated with it in its native or natural state. In one embodiment, the term "isolated" refers to a DNA molecule that is at least partially separated from the nucleic acids that normally flank the DNA molecule in its native or natural state. DNA molecules fused to regulatory or coding sequences with which they are not normally associated, for example as the result of recombinant techniques, are considered isolated herein. Thus, any transgenic, recombinant, chimeric or artificial nucleotide sequence would be considered to be an isolated nucleotide sequence since these are not naturally occurring sequences. A transgenic, recombinant, chimeric or artificial nucleotide sequence would be considered to be an isolated nucleotide sequence whether it is present within the plasmid, vector or construct used to transform plant cells, within the genome of the plant, or is present in detectable amounts in tissues, progeny, biological samples or commodity products derived from the plant. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the transgenically altered plant.

"Specific," for (a target sequence), as used herein, refers broadly to a probe or primer hybridizing under standard stringent hybridization conditions only to the target sequence in a sample comprising the target sequence.

"Sequence identity," with regard to nucleotide sequences (DNA or RNA), as used herein, refers broadly to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the sequence analysis software package of the Genetics Computer Group (GCG, University of Wisconsin Biotechnology center).

As used herein, the term "turfgrass" means any species of grass plant used to create a stand (lawn) which can be maintained by regular mowing to a uniform height, and includes all plant varieties that can be bred with turfgrasses, including wild turfgrass species.

"Variant," as used herein, refers broadly to means a nucleotide sequence that codes for the amino acid sequence differs from the base sequence from which it is derived in that one or more amino acids within the encoded sequence are substituted for other amino acids.

An "event" is a genetic locus that, as a result of genetic engineering, carries a transgene of interest. An "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. An "event" refers to the original transformant and progeny of the transformant that includes the heterologous DNA. An "event" also refers to progeny produced by a sexual outcross between the transformant and another event that include the heterologous DNA. Even after repeated back-crossing to a recurrent parent, the inserted DNA and flanking genomic DNA from the transformed parent is present in the progeny of the cross at the same chromosomal location. An "event" also refers to DNA from the original transformant comprising the inserted DNA and flanking genomic sequence immediately adjacent to the inserted DNA, that would be expected to be transferred to a progeny that receives the inserted DNA including the transgene of interest as the result of a sexual cross of one parental line that includes the inserted DNA (e.g., the original transformant and progeny resulting from selfing) and a parental line that does not contain the inserted DNA.

The transformation of a plant with heterologous DNA, or by back-crossing with plants obtained by such transformation, typically results in a population of transformants comprising a multitude of separate events. Individual events from this group of events are selected based on various criteria such as expression and stability of the transgene(s) and its compatibility with optimal agronomic characteristics of the plant comprising it. As described herein, events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749 were selected based on such characteristics including glyphosate tolerance and enhanced turfgrass quality.

The heterologous (or foreign) DNA can be characterized by the particular location in which it is incorporated into the plant genome. The foreign DNA can be detected by identifying regions or sequences that flank the foreign DNA. These flanking/junction regions or sequences are different from the introduced DNA, and are preferably DNA from the plant genome which is located either immediately upstream of and contiguous with, or immediately downstream of and contiguous with the foreign DNA.

As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene incorporated into a host cell's genomic DNA and the associated flanking DNA of the host cell's genome. An example of a recombinant DNA molecule is a DNA molecule described herein resulting from the insertion of the transgene into the Zea mays genome, which may ultimately result in the expression of a recombinant RNA and/or protein molecule in that organism. The nucleotide sequence or any fragment derived therefrom would also be considered a recombinant DNA molecule if the DNA molecule can be extracted from cells, or tissues, or homogenate from a plant or seed or plant tissue; or can be produced as an amplicon from extracted DNA or RNA from cells, or tissues, or homogenate from a plant or seed or plant tissue, any of which is derived from such materials derived from a plant comprising the events provided herein.

The region spanning the location where the transgenic DNA connects to and is linked to the genomic DNA is referred to herein as the junction. A "junction sequence" or "border sequence" spans the point at which DNA inserted into the genome is linked to DNA from the native genome flanking the insertion point, the identification or detection of one or the other junction sequences in a plant's genetic material being sufficient to be diagnostic for the event. Included are the DNA sequences that span the insertions in herein-described events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention. Examples of a junction sequence of transgenic events designated Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 are provided herein as SEQ ID NOs:1-14. The identification of one of these junction sequences in a nucleotide molecule derived from a plant or seed is conclusive that the DNA was obtained from transgenic events designated Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 and is diagnostic for the presence of DNA from transgenic events designated Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749.

As used herein, the term "progeny" denotes the offspring of any generation of a parent plant, which comprises an event described herein.

Event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749

The invention relates to St. Augustinegrass transgenic events designated Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749, and to plants, cells, plant parts, and seeds comprising these events. These events involve the transformation of two expression cassettes depicted in FIG. 1. The first cassette includes a 5-enol-pyruvylshikimate-3-phosphate synthase (EPSP synthase) gene from *Arabidopsis*, and the second cassette includes a gibberellic acid 2-oxidase gene from spinach. Plants comprising this event are glyphosate-tolerant and possess enhanced turfgrass qualities (e.g., require less mowing, have a darker green color, and/or generate a thicker, fuller stand). The events described herein may be in the original transformant and progeny of the transformant that include the heterologous DNA.

Plants comprising Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 may be produced by growing seeds comprising these events. Plants comprising these events may also be obtained by propagation of and/or breeding of plants comprising the events. Plant parts, such as tuber, crown, stem, tiller, cuttings including un-rooted cuttings, rooted cuttings, and callus cuttings or callus-generated plantlets; apical meristems, pollen, ovule, flowers, shoots, stolons, propagules, seeds, runners, corms, rhizomes, roots, or leaves may that comprise events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 are also encompassed herein.

Progeny comprising the events may be produced by a sexual outcross between a parental plant comprising Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 (e.g., original transformant, plant grown from seed comprising event), and itself or another parental plant that lacks Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749, respectively. The other plant may also lack glyphosate tolerance. The other plant may, however, comprise other events and/or desirable characteristics.

In one embodiment, the invention provides for a method of producing a turfgrass (e.g., St. Augustinegrass) plant or seed comprising crossing a St. Augustinegrass plant comprising event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 with a plant lacking event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 (or by selfing with a plant comprising event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749), and planting seed obtained from the cross or selfing, wherein the seed comprises event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749. The plant lacking the event can be a St. Augustinegrass plant or other plant species that can breed with St. Augustinegrass. The method may also involve selecting progeny plants tolerant to glyphosate. The method may further include backcrossing (or selfing) the progeny plants with a St. Augustinegrass plant comprising event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749. The backcrossing or selfing step may be performed more than once. Plants and seeds comprising event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 obtained from any of these methods are encompassed herein.

In another embodiment, a glyphosate-tolerant, enhanced turfgrass quality St. Augustinegrass plant can be bred by first sexually crossing a parental St. Augustinegrass plant, or other sexually compatible St. Augustinegrass plant, grown from the transgenic St. Augustinegrass plant derived from transformation with the plant expression cassettes contained in plasmid pSCO761 (FIG. 1) that tolerates application of glyphosate herbicide, and a second parental St. Augustinegrass plant that lacks the tolerance to glyphosate herbicide, thereby producing a plurality of first progeny plants; and then selecting a first progeny plant that is tolerant to application of glyphosate herbicide (i.e, first glyphosate herbicide-tolerant plant); and selfing or crossing the first progeny plant, thereby producing a plurality of second progeny plants; and then selecting from the second progeny plants, a glyphosate herbicide tolerant plant (i.e, second glyphosate herbicide-tolerant plant). These steps can further include the back-crossing or crossing of the first glyphosate-tolerant progeny plant or the second glyphosate-tolerant progeny plant to the second parental St. Augustinegrass plant or sexually compatible species or a third parental St. Augustinegrass plant or sexually compatible species, thereby producing a St. Augustinegrass plant that tolerates the application of glyphosate herbicide. Plants and seeds comprising events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 are encompassed herein.

The below Table 1 provides a list of events and transgenes.

TABLE 1

Events and Transgenes

| SEQ ID NO | Sequence Name | Type |
|---|---|---|
| | | Chromosomal flanking sequence from St. Augustinegrass event: |
| 1 | 1819 Sn 1 | Ss026-1819 (1.11 kb) |
| 2 | 1984 RU FNS 1 | Ss026-1984 (230 bp) |
| 3 | 2006 TAIL GO 1 | Ss026-2006 (669 bp) |
| 4 | 2027 ZS 2 | Ss026-2027 (482 bp) |
| 5 | 2050 TAIL GO 1 | Ss026-2050 (790 bp) |
| 6 | 2085 GO Sn 1 | Ss026-2085 (678 bp) |
| 7 | 2085 SZ Sn 1 | Ss026-2085 (358 bp) |
| 8 | 2393 GO Sn 1 | Ss026-2393 (551 bp) |
| 9 | 2475 TAIL GO 1 | Ss026-2475 (571 bp) |
| 10 | 2623 TAIL GOB1 1-3 | Ss026-2623 (345 bp) |
| 11 | 2640 RU Fs 1 | Ss026-2640 (572 bp) |
| 12 | 2693 RU Sn 1 3-5 | Ss026-2693 (358 bp) |
| 13 | 2732 RU Fs 1 | Ss026-2732 (683 bp) |
| 14 | 2749 RUrev468 1-2 | Ss026-1984 (172 bp) |
| | | Transgene |
| 36 | Variant EPSP synthase transgene | transgene (cDNA) |
| 37 | EPSP synthase expression cassette | transgene cassette |
| 38 | GA2OX transgene | transgene (cDNA) |
| 39 | GA2OX expression casette | transgene cassette |

EPSPS Variant Nucleic Acid

The nucleic acid of SEQ ID NO: 36 is a cDNA and encodes a variant of the enzyme 5-enolpyruvyl-3-phoshikimate synthase (EPSPS).

This EPSPS variant has a lower affinity for glyphosate and thus can retain catalytic activity in the presence of glyphosate. The first transgene expression cassette of SEQ ID NO: 37 is a nucleic acid comprises the rice ubiquitin promoter (P-Os.UBQ, also referred to as P-RUBQ) and rice actin 1 intron (I-Os.Actl, also referred to as R-act intron), operably connected to a glyphosate-tolerant 5-enol-pyruvylshikimate-3-phosphate synthase (EPSPS) variant (SEQ ID NO: 36), and operably connected to a Zea mays alcohol dehydrogenase transcriptional terminator. The first transgene expression cassette confers glyphosate resistance in grasses.

Gibberellic Acid 2-Oxidase (GA2QX) Nucleic Acid

The nucleic acid of SEQ ID NO: 38 is a cDNA and encodes gibberellic acid 2-oxidase (GA2OX).

The second transgene expression cassette of SEQ IQ NO: 39 is a nucleic acid construct comprising the Os.GOS2 promoter, operably connected to gibberellic acid 2-oxidase (SEQ ID NO: 38), and operably connected to a *Solanum pennellii* histone HI gene transcriptional terminator. The second transgene expression cassette confers enhanced turfgrass quality in grasses.

Plant Cells Comprising Events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749

DNA molecules useful for identifying events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749 are provided herein. In a particular embodiment, the invention provides for DNA molecules comprising SEQ ID NOs: 1-14, 36-39, or complements thereof, or combinations thereof. Plants, plant cells, plant parts, and seeds comprising one or more of these DNA molecules is also encompassed herein.

Nucleic acid molecules comprising the junction regions for event Ss026-1819, event Ss026-1984, event Ss026-2006, event Ss026-2027, event Ss026-2050, event Ss026-2085, event Ss026-2393, event Ss026-2475, event Ss026-2623, event Ss026-2640, event Ss026-2693, event Ss026-2732, and event Ss026-2749 are also provided herein. In a particular embodiment, the invention provides for nucleic acid molecules comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 or complements thereof. Plants, plant cells, plant parts, and seeds comprising these nucleic acid molecules are also encompassed herein.

Primers, Probes, Variants, and Markers

Primers and probes useful in the detection of event Ss026-1819, event Ss026-1984, event Ss026-2006, event Ss026-2027, event Ss026-2050, event Ss026-2085, event Ss026-2393, event Ss026-2475, event Ss026-2623, event Ss026-2640, event Ss026-2693, event Ss026-2732, and/or event Ss026-2749, and methods of detecting these events are provided herein.

Primers and probes useful in the detection of nucleic acid molecules comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or complements thereof, and/or methods of detecting these nucleic acid molecules are provided herein.

A "primer" is a nucleic acid capable of priming the synthesis of a nascent nucleic acid in a template-dependent process, such as polymerase chain reaction (PCR). A primer anneals to a complementary target DNA strand by nucleic acid hybridization to form a hybrid between the primer and the target DNA strand, and is then extended along the target DNA strand by a polymerase, e.g., a DNA polymerase. Typically, primers are oligonucleotides from 10 to 30 nucleotides (e.g., 11, 12, 13, 14, 15, 16, 17, 18, 19, 20, 21, 22, 23, 24, 25, 26, 27, 28, or 29 nucleotides), but longer sequences may be employed. A "probe" can be used as a primer, but is designed to bind to target DNA or RNA and need not be used in an amplification reaction. Probes, like primers, may range from 10 to 30 nucleotides (e.g., 11, 12, 13, 14, 15, 16, 17, 18, 19, 20, 21, 22, 23, 24, 25, 26, 27, 28, or 29 nucleotides), but longer sequences may be employed.

Primers and probes are selected to be of sufficient length to specifically hybridize to a target sequence under stringent conditions. Preferably, the probes and primers have complete sequence similarity or complementarity with the target sequence, although primers and probes differing from the target sequence (e.g., by 1, 2, 3, 4, 5, 6, 7, 8, 9, or 10 mismatches) that retain the ability to hybridize to target sequences are encompassed herein.

Primers are said to be of "sufficient length" when they are of a length that allows the primer to function in a PCR reaction and specifically amplify a target sequence; a length of about 11 nucleotides or more is sufficient, more preferably about 18 nucleotides or more, yet more preferably about 24 nucleotides or more, even more preferably about 30 nucleotides is sufficient to perform and specifically amplify a target sequence. One skilled in the art would know that a primer of even greater length than about 30 nucleotides can be usefully employed in a PCR reaction and, accordingly, is of a sufficient length. In one or more embodiments of the invention, the primer will have a length of from about 10-50 nucleotides. In another embodiment, the primer will have a length of from about 11-30 nucleotides. In another embodiment, the primer will have a length of from about 18-22 nucleotides.

Regarding the amplification of a target nucleic acid sequence (e.g. by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction. Specificity may be determined by the presence of positive and negative controls. For example, an analysis for event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749 plant tissue sample may include a positive tissue control from Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749, respectively, a negative control from a plant (e.g., a St. Augustinegrass) that is not event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749, respectively, and a negative control that contains no DNA from the plant. In another example, when performing a PCR to identify the presence of event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749 in unknown samples, a control is included of a set of primers with which a fragment within a "housekeeping gene" of the plant species of the event can be amplified. Housekeeping genes are genes expressed in most cell types and that are concerned with basic metabolic activities common to all cells. Preferably, the fragment amplified from the housekeeping gene is a fragment larger than the amplified integration fragment. Depending on the samples to be analyzed, other controls can be included.

Regarding the amplification of a target nucleic acid sequence (e.g. by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction. Specificity may be determined by the presence of positive and negative controls. For example, an analysis for plant tissue sample comprising nucleic acid molecules of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, may include a positive tissue control from nucleic acid molecules of one or more of these SEQ ID NOs, respectively, a negative control from a plant that is does not comprise nucleic acid molecules of these SEQ ID NOs, respectively, and a negative control that contains none of the plant DNA. In another example, when performing a PCR to identify the presence of nucleic acid molecules of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, in unknown samples, a control is included of a set of primers with which a fragment within a "housekeeping gene" of the plant species of the event can be amplified. Housekeeping genes are genes expressed in most cell types and that are concerned with basic metabolic activities common to all cells. Preferably, the fragment amplified from the housekeeping gene is a fragment larger than the amplified integration fragment. Depending on the samples to be analyzed, other controls can be included.

Regarding the hybridization of a target sequence and a probe, the probe will specifically hybridize to the complement of the target nucleic acid sequence under standard stringency conditions. Standard stringency conditions as used herein refers to the conditions for hybridization described herein or to the conventional hybridizing conditions as described in *Molecular Cloning: A Laboratory Manual*, 3rd ed., Vols 1,2 and 3; J. F. Sambrook and D. W. Russell, ed., Cold Spring Harbor Laboratory Press, 20 ("Sambrook"), which, for instance, can comprise the following steps: (1) immobilizing plant genomic DNA fragments on a filter, (2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, (3) adding the hybridization probe which has been labeled, (4) incubating for 16 to 24 hours, (5) washing the filter for 20 minutes at room temperature in 1×SSC, 0.1% SDS, (6) washing the filter three times for 20 minutes each at 68° C. in 0.2×SSC, 0.1% SDS, and (7) exposing the filter for 24 to 48 hours to X-ray film at −70° C. with an intensifying screen.

Contacting nucleic acid of a biological sample with the probe under conditions which allow hybridization of the probe with its corresponding fragment in the nucleic acid, results in the formation of a nucleic acid/probe hybrid. The formation of this hybrid can be detected, whereby the formation of this hybrid indicates the presence of event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749. The formation of this hybrid can be detected, whereby the formation of this hybrid indicates the presence of nucleic acid molecules of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14. Such identification methods based on hybridization with a specific probe (either on a solid phase carrier or in solution) are well-known and described in the art. The target nucleic acid target or the probe may be labeled with a conventional detectable label or reporter molecule, e.g., a florescent molecule, a radioactive isotope, ligand, chemifluorescent, chemiluminescent agent, or enzyme.

Techniques for the manipulation of nucleic acids, such as, for example, for generating mutations in sequences, subcloning, labeling probes, sequencing, hybridization are well described in the scientific and patent literature. See, e.g., Sambrook; see also Ausubel, et al. (2011) Ed., *Current*

*Protocols in Molecular Biology*, John Wiley & Sons, Inc., New York (Ausubel"); Tijssen (1993) Ed., *Laboratory Techniques in Biochemistry and Molecular Biology: Hybridization With Nucleic Acid Probes, Part L Theory and Nucleic Acid Preparation*, Elsevier, N.Y. ("Tijssen").

The invention provides for a primer pair for detecting the transgene/junction regions of event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749. These primer pairs are used to produce an amplicon diagnostic for the events. In one aspect, any primer pair derived from SEQ ID NO: 1, SEQ ID NO: 2, SEQ ID NO: 3, SEQ ID NO: 4, SEQ ID NO: 5, (SEQ ID NO: 6 or SEQ ID NO: 7), SEQ ID NO: 8, SEQ ID NO: 9, SEQ ID NO: 10, SEQ ID NO: 11, SEQ ID NO: 12, SEQ ID NO: 13 or SEQ ID NO: 14 that, in a DNA amplification reaction produces an amplicon diagnostic for St. Augustinegrass event Ss026-1819, Ss026-1984, Ss026-2006, Ss026-2027, Ss026-2050, (Ss026-2085), Ss026-2393, Ss026-2475, Ss026-2623, Ss026-2640, Ss026-2693, Ss026-2732, and/or Ss026-2749, respectively, is encompassed herein. In another aspect, any isolated DNA polynucleotide primer or primer pair comprising at least 11 (e.g., 12, 13, 14, 15, 16, 17, 18, 19, 20, 21, 22, 23, 24, 25, 26, 27, 28, or 29) contiguous nucleotides of SEQ ID NO: 1, SEQ ID NO: 2, SEQ ID NO: 3, SEQ ID NO: 4, SEQ ID NO: 5, (SEQ ID NO: 6 or SEQ ID NO: 7), SEQ ID NO: 8, SEQ ID NO: 9, SEQ ID NO: 10, SEQ ID NO: 11, SEQ ID NO: 12, SEQ ID NO: 13, or SEQ ID NO: 14, or their complement, useful in a DNA amplification method to produce an amplicon diagnostic for St. Augustinegrass event Ss026-1819, Ss026-1984, Ss026-2006, Ss026-2027, Ss026-2050, (Ss026-2085), Ss026-2393, Ss026-2475, Ss026-2623, Ss026-2640, Ss026-2693, Ss026-2732, and Ss026-2749, respectively, is an aspect of the invention. In a particular aspect, Ss026-1819, Ss026-1984, Ss026-2006, Ss026-2027, Ss026-2050, (Ss026-2085), Ss026-2393, Ss026-2475, Ss026-2623, Ss026-2640, Ss026-2693, Ss026-2732, or Ss026-2749 event primer pairs that will produce a diagnostic amplicon for St. Augustinegrass events Ss026-1819, Ss026-1984, Ss026-2006, Ss026-2027, Ss026-2050, (Ss026-2085), Ss026-2393, Ss026-2475, Ss026-2623, Ss026-2640, Ss026-2693, Ss026-2732, or Ss026-2749, respectively, include, but are not limited to, a primer pair comprising Ss026-1819 event primers 1 and 2; Ss026-1984 event primers 1 and 2; Ss026-2006 event primers 1 and 2; Ss026-2027 event primers 1 and 2; Ss026-2050 event primers 1 and 2; Ss026-2085 event primers 1 and 2 (both junction sequences); Ss026-2393 event primers 1 and 2; Ss026-2475 event primers 1 and 2; Ss026-2623 event primers 1 and 2; Ss026-2640 event primers 1 and 2; Ss026-2693 event primers 1 and 2; Ss026-2732 event primers 1 and 2; and Ss026-2749 event primers 1 and 2. In another aspect, amplicons diagnostic for events Ss026-1819, Ss026-1984, Ss026-2006, Ss026-2027, Ss026-2050, (Ss026-2085), Ss026-2393, Ss026-2475, Ss026-2623, Ss026-2640, Ss026-2693, Ss026-2732, and/or Ss026-2749 comprise at least one junction sequence comprising SEQ ID NO: 1, SEQ ID NO: 2, SEQ ID NO: 3, SEQ ID NO: 4, SEQ ID NO: 5, (SEQ ID NO: 6 or SEQ ID NO: 7), SEQ ID NO: 8, SEQ ID NO: 9, SEQ ID NO: 10, SEQ ID NO: 11, SEQ ID NO: 12, SEQ ID NO: 13, and/or SEQ ID NO: 14, respectively.

The invention also provides for probes specific for the transgene/junction regions of event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749. The probes are DNA molecules that hybridize specifically to a region within the 5' flanking region of the event and a region of the foreign/transgene DNA contiguous therewith. Exemplary probes include, but are not limited to DNA molecules comprising SEQ ID NO: 1 (event Ss026-1819), SEQ ID NO: 2 (event Ss026-1984), SEQ ID NO: 3 (event Ss026-2006), SEQ ID NO: 4 (event Ss026-2027), SEQ ID NO: 5 (event Ss026-2050), SEQ ID NO: 6 (event Ss026-2085), SEQ ID NO: 7 (event Ss026-2085), SEQ ID NO: 8 (event Ss026-2393), SEQ ID NO: 9 (event Ss026-2475), SEQ ID NO: 10 (event Ss026-2623), SEQ ID NO: 11 (event Ss026-2640), SEQ ID NO: 12 (event Ss026-2693), SEQ ID NO: 13 (event Ss026-2732), and SEQ ID NO: 14 (event Ss026-2749). In another aspect, the probe comprises a sequence of between 50 basepairs (bp) and 500 bp, preferably of 100 to 350 bp which is at least 80%, 85%, 90%, 95%, 97%, 98%, 99%, or 100% identical to an event junction nucleotide sequence (e.g., nucleic acid molecule comprising SEQ ID NOs: 1-14, or the complement(s) thereof). In a particular embodiment, the probe comprises or specifically hybridizes to one or more of the nucleic acid molecules set forth in SEQ ID NOs: 1-14, or the complement(s) thereof, or fragment(s) thereof, under standard stringency conditions.

In another aspect, the probe comprises a sequence of between 50 bp and 500 bp, preferably of 100 to 350 bp which is at least 80%, 85%, 90%, 91% 92%, 93%, 94%, 95%, 96%, 97%, 98%, 99%, or 100% identical to the nucleotide sequence comprising SEQ ID NO: 36, SEQ ID NO: 37, SEQ ID NO: 38, and/or SEQ ID NO: 39. In a particular embodiment, the probe comprises or specifically hybridizes to one or more of the nucleic acid molecules comprising SEQ ID NO: 36, SEQ ID NO: 37, SEQ ID NO: 38, and/or SEQ ID NO: 39, or the complement(s) thereof, or fragment(s) thereof, under standard stringency conditions.

The present invention also encompasses variants of the nucleic acids described herein. The variant nucleic acids may encode amino acid substitutions that may be regarded as "conservative," i.e., where an amino acid is replaced with a different amino acid with broadly similar properties. Non-conservative substitutions are where amino acids are replaced with amino acids of a different type.

As is well-known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region that is critical in determining the peptide's conformation. This substitution may be accomplished by changing the codon in the underlying nucleic acid.

The invention encompasses variant nucleic acids encoding the polypeptide of the invention. The term "variant" in relation to a nucleic acid sequences means any substitution of, variation of, modification of, replacement of deletion of, or addition of one or more nucleic acid(s) from or to a polynucleotide sequence providing the resultant polypeptide sequence encoded by the polynucleotide exhibits at least the same properties as the polypeptide encoded by the basic sequence. The term therefore includes allelic variants and also includes a polynucleotide that substantially hybridizes to the polynucleotide sequence of the present invention. Such hybridization may occur at or between low and high stringency conditions. In general terms, low stringency conditions can be defined a hybridization in which, e.g., the washing step takes place in a 0.330-0.825 M NaCl buffer solution at a temperature of about 40-48° C. below the calculated or actual melting temperature of the probe sequence (for example, about ambient laboratory temperature to about 55° C.), while high stringency conditions involve, e.g., a wash in a 0.0165-0.0330 M NaCl buffer solution at a temperature of about 5-10° C. below the calculated or actual melting temperature of the probe (for example, about 65° C.). The buffer solution may, for example, be SSC buffer (0.15M NaCl and 0.015M trisodium citrate), with the low stringency wash taking place in 3×SSC buffer and the high stringency wash taking place in 0.1×SSC buffer. Steps involved in hybridization of nucleic acid sequences have been described for example in Sambrook, and by Hames, et al. (1985) in *Nucleic Acid Hybridization, a Practical Approach* (IRL Press, DC) ("Hames").

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules isolated from St. Augustinegrass events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749.

As used herein, "amplified DNA" or "amplicon" refers to the product of polynucleic acid amplification of a target polynucleic acid molecule that is part of a polynucleic acid template. For example, to determine whether a St. Augustinegrass plant resulting from a sexual cross contains transgenic event genomic DNA from the St. Augustinegrass Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749, DNA extracted from a St. Augustinegrass plant tissue sample may be subjected to polynucleic acid amplification method using a primer pair described herein (e.g., a primer pair that includes a primer derived from flanking DNA in the genome of a Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749 plant adjacent to the insertion site of the inserted heterologous DNA, and a second primer derived from the inserted heterologous DNA to produce an amplicon diagnostic for the presence of the Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, or Ss026-2749 event DNA). The amplicon is of a length and has a polynucleotide sequence that is also diagnostic for the event. The amplicon may range in length from the combined length of the primer pairs plus one nucleotide base pair, preferably plus about 50 nucleotide base pairs, more preferably plus about 250 nucleotide base pairs, and even more preferably plus about 450 nucleotide base pairs or more. In one or more embodiments, the amplicon diagnostic is between 25-2500 base pairs. In another embodiment, the amplicon diagnostic is between 50-2000 base pairs. In another embodiment, the amplicon diagnostic is between 100-1000 base pairs. In another aspect, the amplicon diagnostic for Ss026-1819 is between 250-2500 base pairs. In another aspect, the amplicon diagnostic for Ss026-1984 is between 250-2500 base pairs. In another aspect, the amplicon diagnostic for Ss026-2006 is between 250-2500 base pairs. In another aspect, the amplicon diagnostic for Ss026-2027 is between 250-2500 base pairs. In another aspect, the amplicon diagnostic for Ss026-2050 is between 250-2500 base pairs. In another aspect, the amplicon diagnostic for Ss026-2085 is between 250-2500 base pairs. In another aspect, the amplicon diagnostic for Ss026-2393 is between 250-2500 base pairs. In another aspect, the amplicon diagnostic for Ss026-2475 is between 250-2500 base pairs. In another aspect, the amplicon diagnostic for Ss026-2623 is between 250-2500 base pairs. In another aspect, the amplicon diagnostic for Ss026-2640 is between 250-2500 base pairs. In another aspect, the amplicon diagnostic for Ss026-2693 is between 250-2500 base pairs. In another aspect, the amplicon diagnostic for Ss026-2732 is between 250-2500 base pairs. In another aspect, the amplicon diagnostic for Ss026-2749 between 250-2500 base pairs. The use of the term "amplicon" specifically excludes primer dimers that may be formed in the DNA thermal amplification reaction.

A member of a primer pair used herein may be derived from genomic sequence located a distance from the inserted DNA molecule. This distance can range from one nucleotide base pair up to about 20,000 nucleotide base pairs. Alternatively, a primer pair can be derived from genomic sequence flanking one or both sides of the inserted heterologous DNA so as to produce an amplicon that includes the entire insert polynucleotide sequence (e.g., a primer pair that amplifies an inserted DNA molecule comprising the expression cassette of plasmid pSCO761 that was transformed into St. Augustinegrass.

The invention also encompasses marker nucleic acid molecules comprising the nucleic acid sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 and/or complements and fragments thereof. The marker nucleic acid molecules may share 80%, 85%, 90%, 91%, 92%, 93%, 94%, 95%, 97%, 98%, 99%, or 100% sequence identity with the nucleic acid sequence set forth in SEQ ID NO: 1-14, complements thereof, or fragments of either. The marker nucleic acid molecules may be used as markers in plant breeding methods to identify the progeny of genetic crosses similar to the methods described for simple sequence repeat DNA marker analysis, in Cregan, et al., "DNA markers: Protocols, applications, and overviews," 173-185, Wiley-Liss NY (1997). The hybridization of the probe to the target DNA molecule can be detected by any number of methods known to those skilled in the art, including fluorescent tags, radioactive tags, antibody based tags, and chemiluminescent tags.

Amplication and Identification Techniques

Polynucleic acid amplification can be accomplished by any of the various polynucleic acid amplification methods known in the art, including the polymerase chain reaction (PCR) and are described, for example, in U.S. Pat. Nos. 4,683,195 and 4,683,202 and in *PCR Protocols: A Guide to Methods and Applications*, ed. Innis, et al., Academic Press, San Diego, 1990. PCR amplification methods have been developed to amplify up to 22 kb of genomic DNA and up to 42 kb of bacteriophage DNA (Cheng, et al., Proc. Natl. Acad. Sci. USA 91:5695-5699, 1994). These methods as well as other methods known in the art of DNA amplification may be used in the practice of the invention. Suitable DNA amplification conditions may be determined and/or modified by those skilled in the art to produce an amplicon diagnostic for event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749. Further, it is understood that these conditions may be modified by those skilled in the art to produce an amplicon diagnostic for the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:

8, SEQ ID NO: 9, SEQ ID NO: 10, SEQ ID NO: 11, SEQ ID NO: 12, SEQ ID NO: 13, 14, SEQ ID NO: 33, SEQ ID NO: 34, SEQ ID NO: 35, SEQ ID NO: 36, SEQ ID NO: 37, SEQ ID NO: 38, SEQ ID NO: 39 or complements thereof.

The sequence of the heterologous DNA insert or flanking genomic DNA from St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749 can be verified by amplifying such DNA molecules from the event using primers derived from the sequences provided herein followed by standard DNA sequencing of the PCR amplicon or of the cloned DNA. DNA detection kits that are based on DNA amplification methods contain DNA primers that specifically amplify a diagnostic amplicon. The kit may provide an agarose gel based detection method or any number of methods of detecting the amplicon known in the art.

The amplicon produced by these methods may be detected by a plurality of techniques. For example, Genetic Bit Analysis (Nikiforov, et al., Nucleic Acid Res. 22:4167-4175, 1994) is a method where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphate (ddNTPs) specific for the expected next base. Readout may be fluorescent or ELISA-based. A signal indicates presence of the insert/flanking sequence due to successful amplification, hybridization, and single base extension.

In pyrosequencing (Winge, Innov. Pharma. Tech. 00:18-24, 2000), an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. Deoxyribonucleotides (DNTPs) are added individually and the incorporation results in a light signal that is measured. A light signal indicates the presence of the transgene insert/flanking sequence due to successful amplification, hybridization, and single or multi-base extension.

Fluorescence Polarization (Chen, et al., Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (Applied Biosystems, Foster City, Calif.) is another method of detecting and quantifying the presence of a DNA sequence. Briefly, a FRET (Fluorescence Resonance Energy Transfer) oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons (Tyagi et al., Nature Biotech. 14:303-308, 1996) may also be used. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

Identification of unknown nucleotide sequences flanking already characterized DNA regions can be pursued by a number of different PCR-based methods, including genome-walking (also known as gene walking PCR), thermal asymmetric interlaced PCR (TAIL-PCR), inverse PCR, novel Alu-PCR and vectorette- or splinkerette-PCR, restriction-site PCR, capture PCR, and panhandle PCR, and boomerang DNA amplification. See generally, E. K. Hui et al., "Strategies for cloning unknown cellular flanking DNA sequences from foreign integrants," Cell Mol Life Sci 54, 1403-1411 (1998).

Genome-walking and TAIL-PCR are particularly advantageous methods of identifying, amplifying, and/or analyzing the DNA sequence of unknown genomic regions flanking a region of known DNA sequence. Genome-walking can capture 6-7 KB (kilobases) of sequence in a single round. Genome-walking also has significant utility for capturing homologous genes in new species when there are areas in the target gene with strong sequence conservation to the characterized species. The only requirement is the availability of a known nucleotide sequence from which to start. Several genome-walking methods have been developed in the last 25 years, with continuous improvements added to the first basic strategies, including the recent coupling with next generation sequencing technologies. See, e.g., C. Leoni et al., "Genome-walking in eukaryotes," FEBS J. 278:21 3953-3977 (2011); F. M. Shafter and D. L. Waters, "Genome-walking," Methods of Mol. Biol. 1099:133-146 (2014). Genome-walking begins with having a known sequence present in genomic DNA, and using probes based on that known sequence to read into the surrounding, unknown DNA.

Prior to the advent of PCR, the method involved hybridization of a labeled piece of that known sequence to a collection of restriction-digested genomic fragments cloned into a vector, such as modified bacteriophage vector Charon 4A (See Sambrook et al, "Molecular Cloning: a laboratory manual, 2nd Ed, 1989). A field of plaques on a bacteria lawn will be screened with the probe, each plaque containing a cloned genomic fragment. Typically, a fragment hybridizing to the target sequence will also overlap with the desired unknown flanking sequence. In essence, identifying adjacent sequence allows the researcher to "walk" a new step along the genome.

With PCR, more rapid and direct methods are available for probing from known into unknown sequence. They capitalize on the properties of single-strand DNA to recognize and bind to its exact complement, even short pieces (oligonucleotides) of 20 or 30 bases. When an oligonucleotide within the transgene is paired with another oligonucleotide recognizing another sequence within 1 to 5 KB distant, the length of DNA in between the binding sites can be copied, and cloned.

For both methods used in cloning flanking sequences for this invention, we used an oligonucleotide that recognizes the transgene, and paired it with either a degenerate oligonucleotide that could randomly bind in unknown sequence (TAIL—PCR) or a precise oligonucleotide that recognizes an adaptor that is added to the cut-end of restriction-digested genomic DNA (Genomewalker™)

Figure 2:
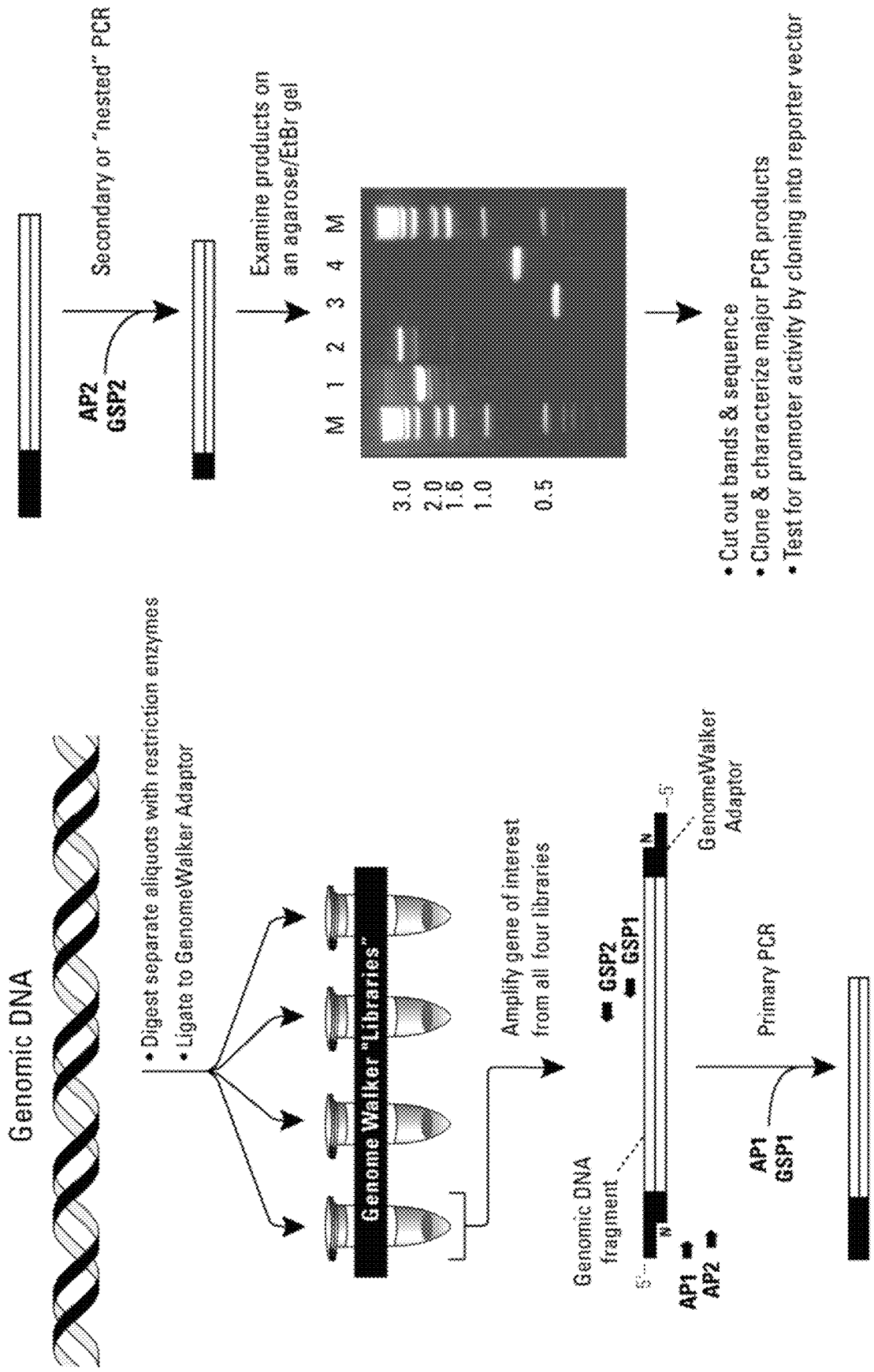
FIG. 2 depicts a diagragm of the general GenomeWalker™ methods. In the method, nested primers are designed that match the end of the "target" gene, called Gene-Specific Primer ("GSP") 1 and 2. A set of GSP1/2 primers is designed for each end of the transgene. Genomic DNA of a transgenic plant is then cut with a restriction endonuclease enzyme that creates small and large pieces which all have a blunt (squared-off) end, such as BsaBI, FspI, SnaBI, NruI.

The Genomewalker™ method for cloning flanking sequences can be done using a Clontech™ kit produced by TakaraBio USA (formerly Clontech Laboratories, Inc.) (Catalog no 636405). The illustration in FIG. 2, copied from the instruction manual, summarizes the GenomeWalker™ method.

The method, in brief, is as follows. First, nested primers are designed that match the end of the gene, called Gene-Specific Primer ("GSP") 1 and 2. A set of GSP1/2 primers is designed for each end of the transgene. Next, genomic DNA of a transgenic plant is cut with a restriction endonuclease enzyme that creates small and large pieces which all have a blunt (squared-off) end, such as BsaBI, FspI, SnaBI, NruI. Examples of recognition sequence and blunt end formed is shown in Table 2.

TABLE 2

| blunt-cutting enzyme | recognition sequence and blunt end formed |
|---|---|
| FspI | . . . TGC GCA . . . |
|  | . . . ACG CGT . . . |
| NruI | . . . TCG CGA . . . |
|  | . . . AGC GCT . . . |
| SnaBI | . . . TAC GTA . . . |
|  | . . . ATG CAT . . . |

Each restriction endonuclease cuts at a precise and distinct code of bases (e.g., TACGTA for SnaBI). Whereas they are code-dependent, the positions of these sites are randomly located throughout the genome. The Clontech™ kit manual recommends that at least four separate digests, each with a different restriction endonuclease, be prepared for each genomic target, to increase the chances of a site that is close to an inserted transgene.

The pieces are then "glued" (ligated) to a short piece of DNA (an "adaptor") using the enzyme T4 DNA ligase. The kit comes with two nested primers that bind to two different sites on the adaptor ("AP1" and "AP2"). The resulting mixture of ligated fragments is a "library," which is used to "check out" any desired flanking sequence by doing two polymerase chain reactions (PCR) in succession. The library is used as a template for the first PCR with GSP1 and AP1 (the outermost nested primers), creating a series of bands. The band product of the first PCR is then used as a template for a second PCR reaction using GSP2 and AP2 (the innermost nested primers). Any PCR product that has both AP1/GSP1 and AP2/GSP2 binding recognition will be amplified to a strongly intense band, and is a likely flanking candidate. This band can be then cloned, sequenced, and tested for event-specificity. The serial PCR reactions can be performed with GSP1/2 primers from both ends of the transgene. Preferably, the cutting-site for the restriction endonuclease used to create the fragments is relatively close to an inserted transgene (ideally within about 2 kilobases).

Figure 4:
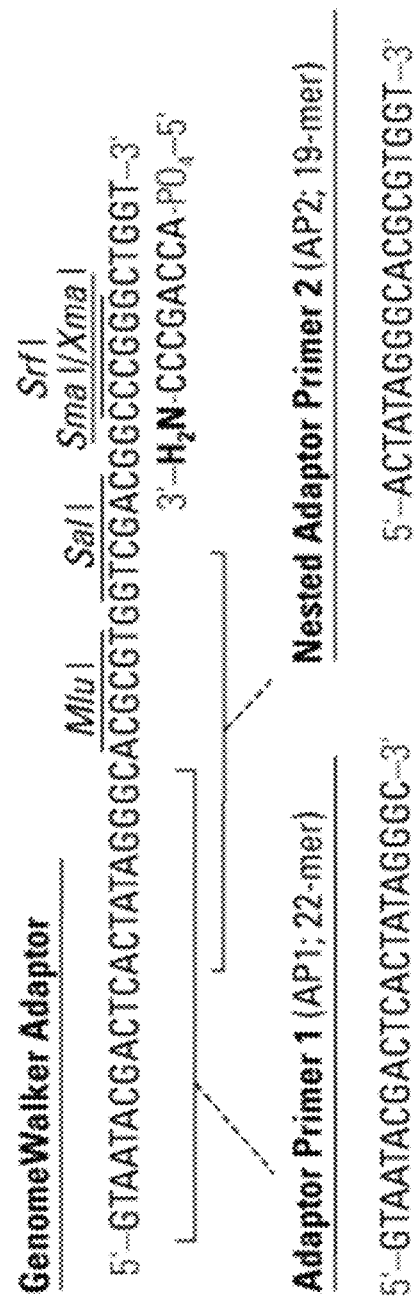
FIG. 4 is an illustration showing the sequences of the Genomewalker™ adaptor (SEQ ID NO: 53) and nested adaptor primers 1 and 2 (SEQ ID NOS: 54 and 55, respectively).
Figure 3:
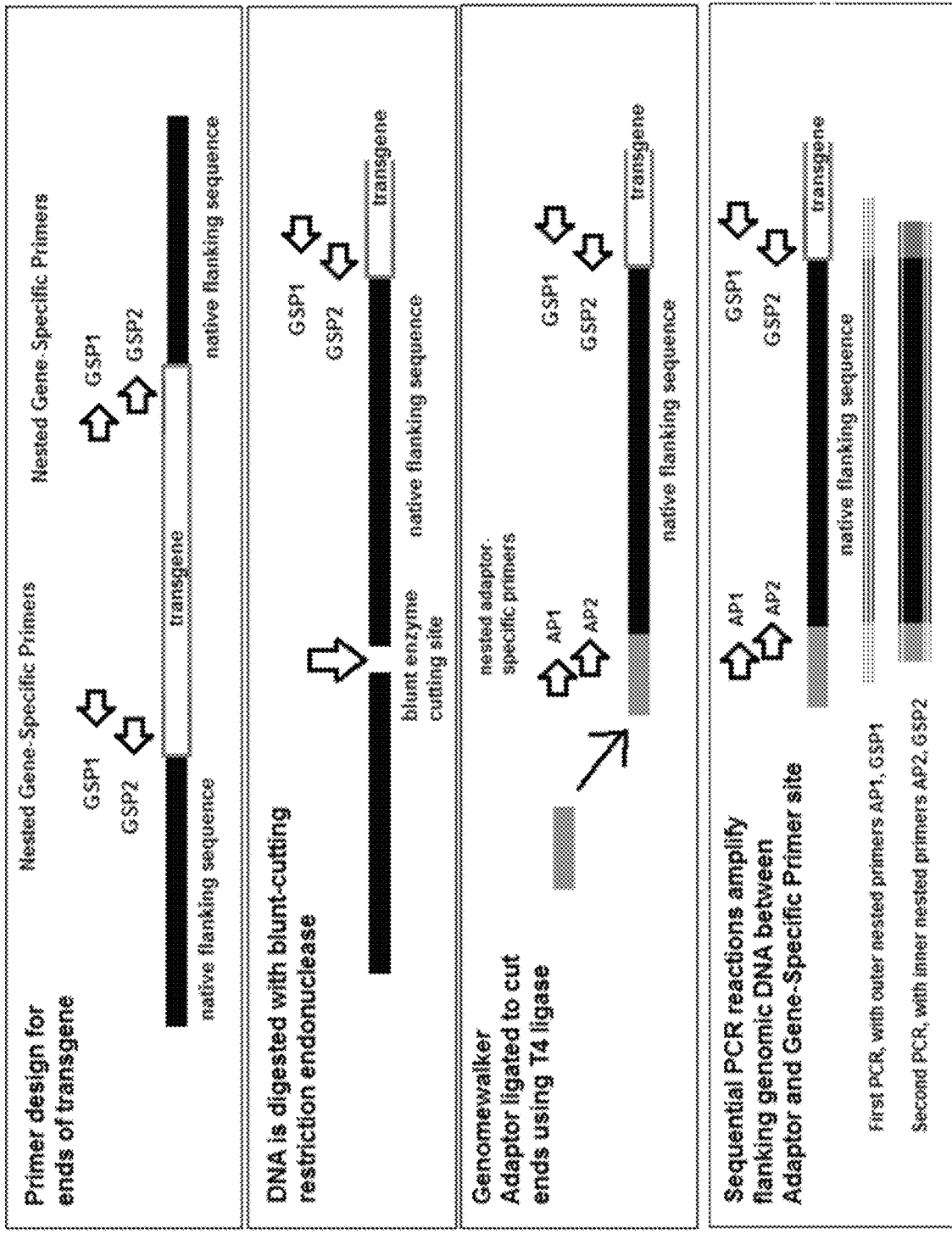
FIG. 3 is an illustration showing one scenario of a flanking sequence being PCR-cloned from one end of the gene using the Genomewalker™ method.

FIG. 3 shows a scenario of a flanking sequence being PCR-cloned from one end of the gene. However, it is possible that sequences flanking either side of the gene insertion could be successfully cloned, depending on the likelihood of the blunt enzyme site being in close enough proximity to the transgene insertion for PCR-amplification. The illustrations shown in FIG. 4, from the Genomewalker™ manual, shows the sequences of the Genomewalker™ adaptor (SEQ ID NO: 53) and nested adaptor primers 1 and 2 (SEQ ID NOS: 54 and 55, respectively).

Various modifications can be made to the foregoing GenomeWalker™ protocol. For example, it may be desirable to prepare, for each transgenic event, a single GenomeWalker™ library from genomic DNA that is cut with multiple restriction endonucleases together. In one example, the restriction endonucleases FspI, NruI, and SnaBI could be used. This modification may facilitate the process of finding flanking sequences since a single library, instead of three libraries per event, may allow more events to be analyzed with less time and reagents. In addition, a single library may help facilitate replicate PCR reactions to be performed, and bands that do not appear in both/all replicate reactions are likely artifacts and can be overlooked.

Like GenomeWalker™, TAIL-PCR is a method for identifying unknown sequences adjacent to known DNA sequences. In one version of the method, nested, insertion-specific primers are used together with arbitrary degenerate primers (AD primers), which are designed to differ in their annealing temperatures. Alternating cycles of high and low annealing temperature yield specific products bordered by an insertion-specific primer on one side and an AD primer on the other. Further specificity is obtained through subsequent rounds of TAIL-PCR, using nested insertion-specific primers. See generally, Y. G. Liu Y-G and Y. Chen, "High-efficiency thermal asymmetric interlaced [TAIL] PCR for amplification of unknown flanking sequences," *Bio/Techniques* 43(5):649 (2007) ("Liu & Chen"); see also Y. G. Liu and R. F. Whittier, "Thermal asymmetric interlaced PCR: automatable amplification and sequencing of insert end fragments from P1 and YAC clones for chromosome walking," *Genomics* 25(3):674-681 (1995); T. Singer and E. Burke, "High-throughput TAIL-PCR as a tool to identify DNA flanking insertions," *Methods of Mol. Biol.* 236:241-271 (2003).

Figure 5A:
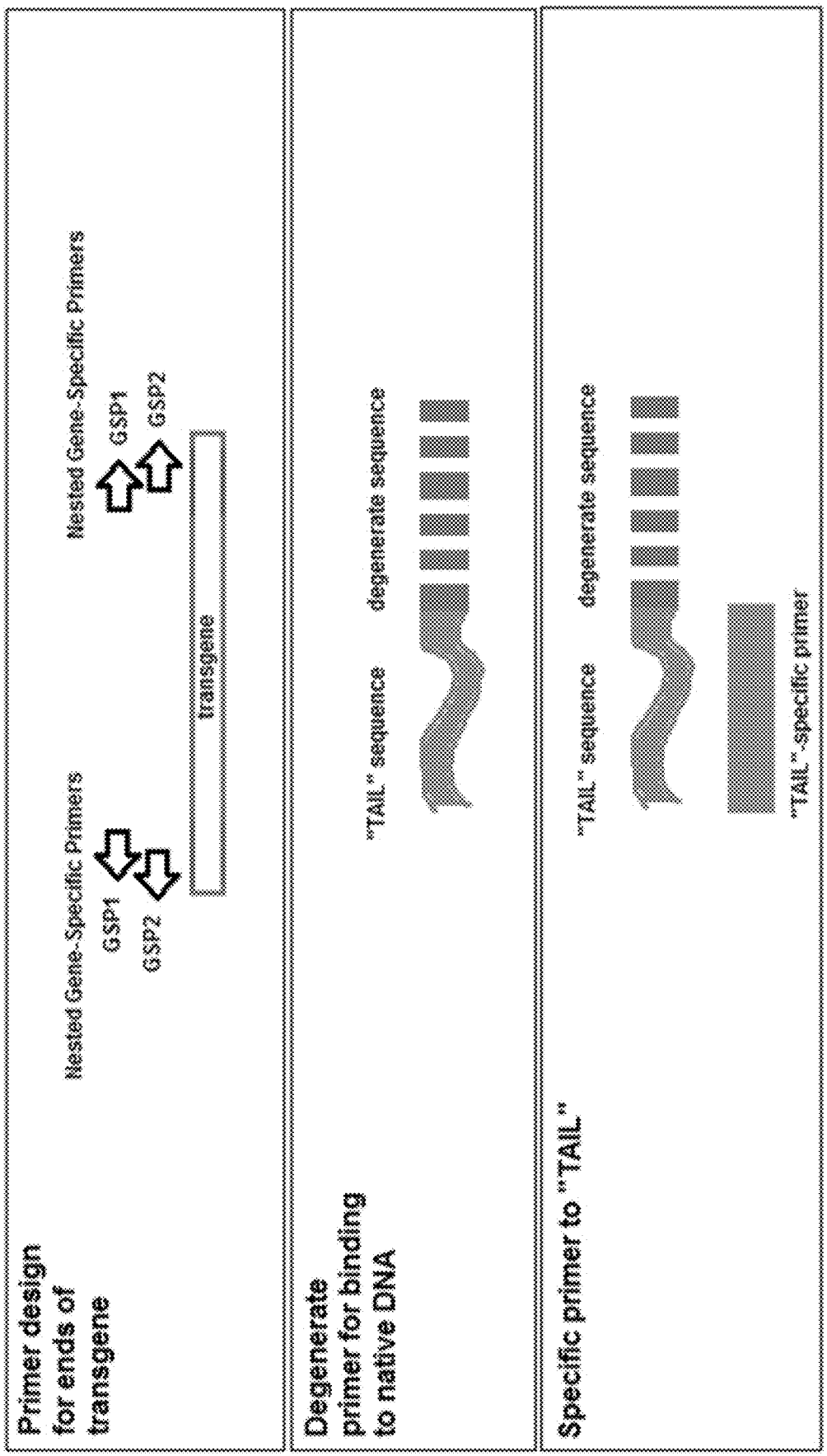
FIGS. 5A and 5B are illustrations showing one embodiment of the TAIL-PCR method. In the diagram, the TAIL-PCR procedure uses unequal concentrations of specific and random (degenerate) primers, the latter of which have a tail at one end that hybridizes to a specific primer.
Figure 5B:
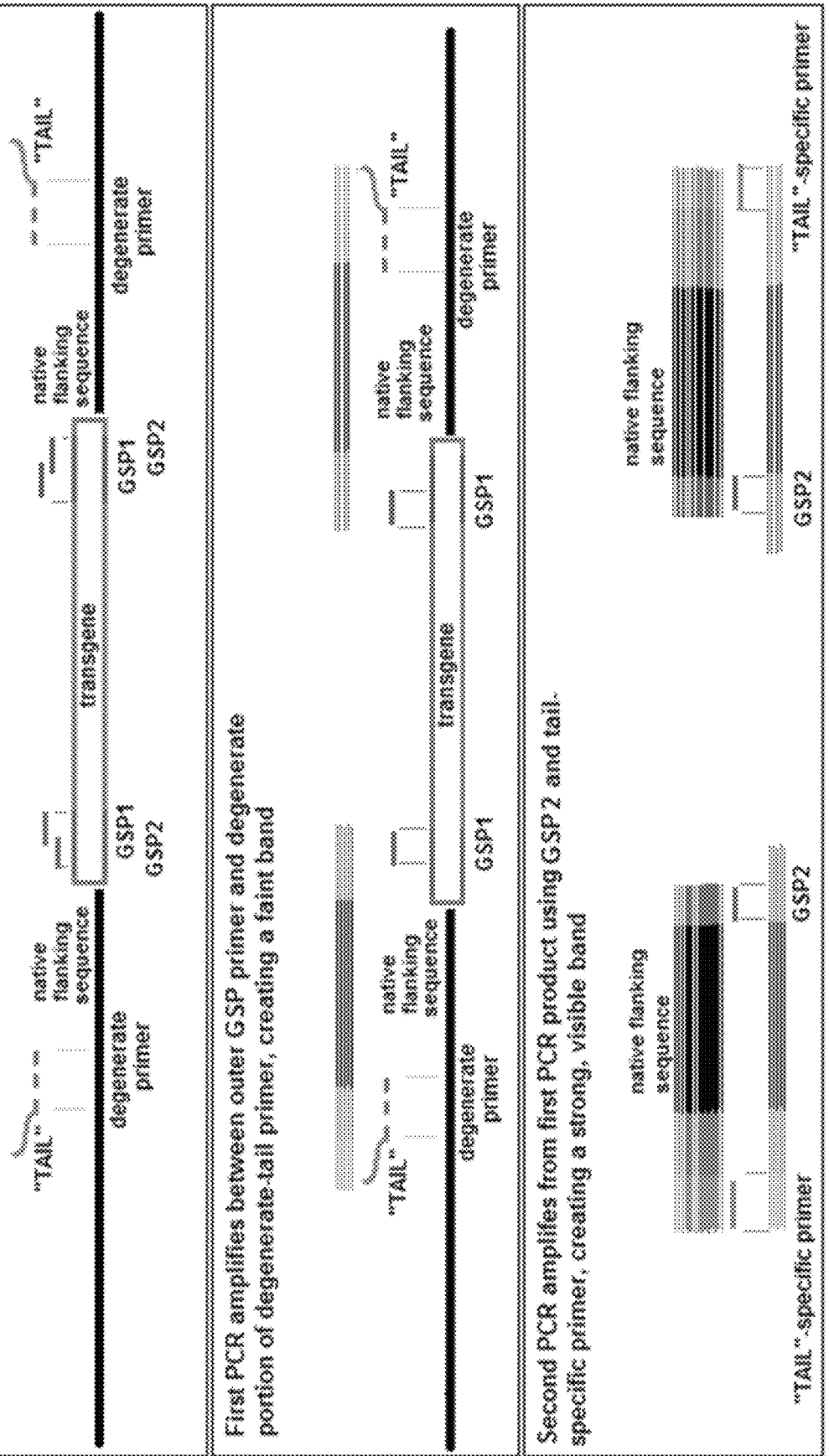
Figure 6A:
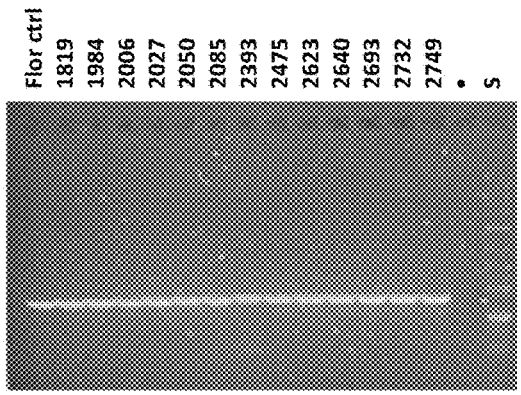
FIGS. 6A-6P show photographs of an electrophoresis gel showing PCR bands from reactions using primers disclosed herein. The gels shown are from an event-specific PCR of 13 transgenic St. Augustinegrass events, using primers for characterized flanking sequences to transgene insertions. The gels are as follows: (A) results of a positive control PCR reaction using primers for a St Augustinegrass native gene (kaurene oxidase) present in all DNA samples tested. (B) results of a transgene-specific set of primers contained within the GA2OX transgene cassette, present in all transgenic events but negative in the non-transgenic control. (C-P) results of event-specific PCR described herein, using primers which detect and amplify the diagnostic flanking sequence for a specific transgenic event: (C) using identifier primers for 1819 Sn 1 (SEQ ID NO: 1); (D) using identifier primers for 1984 RU FNS 1 (SEQ ID NO: 2); (E) using identifier primers for 2006 TAIL GO 1 (SEQ ID NO: 3); (F) using identifier primers for 2027 ZS 2 (SEQ ID NO: 4); (G) using identifier primers for 2050 TAIL GO 1(SEQ ID NO: 5), (H) using identifier primers for 2085 GO Sn 1 (SEQ ID NO: 6); (I) using identifier primers for 2085 SZ Sn 1 (SEQ ID NO: 7); (J) using identifier primers for 2393 GO Sn 1 (SEQ ID NO: 8); (K) using identifier primers for 2475 TAIL GO 1 (SEQ ID NO: 9); (L) using identifier primers for 2623 TAIL GOBI 1-3 (SEQ ID NO: 10); (M) using identifier primers for 2640 RU Fs 1 (SEQ ID NO: 11); (N) using identifier primers for 2693 RU Sn 1 (SEQ ID NO: 12); (O) using identifier primers for 2732 RU Fs 1 (SEQ ID NO: 13); (P) using identifier primers for 2749 RUrev468 1-2 (SEQ ID NO: 14). The results of each set of PCR reactions show expected event-specificity. Lanes marked with an "S" show size markers (2 log ladder, New England Biolabs, part no N3200) and lanes marked "•" are empty.
Figure 6B:
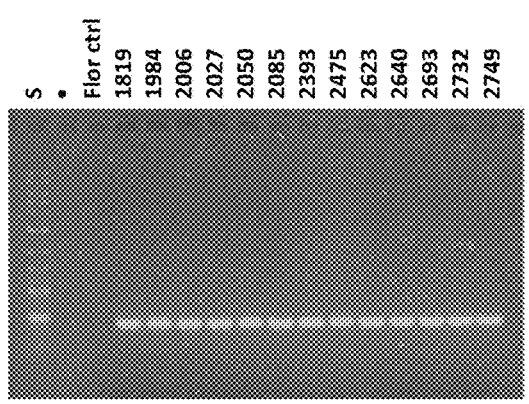
Figure 6C:
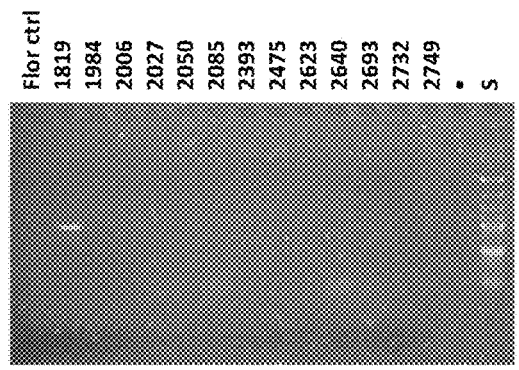
Figure 6D:
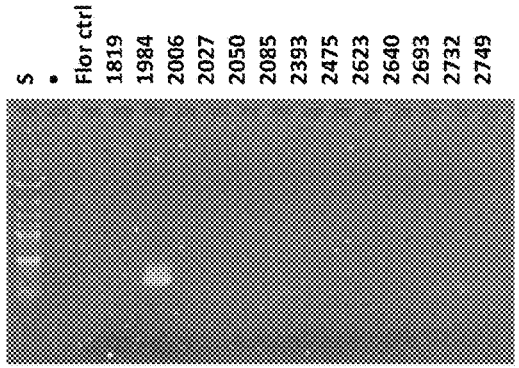
Figure 6E:
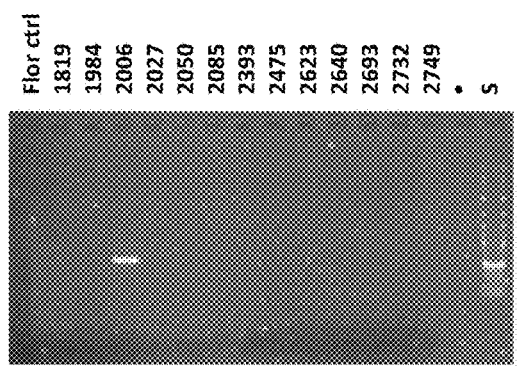
Figure 6F:
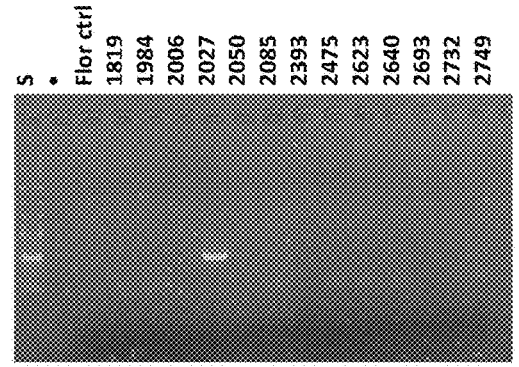
Figure 6G:
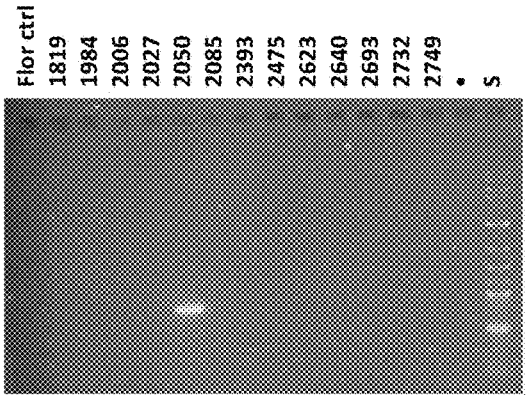
Figure 6H:
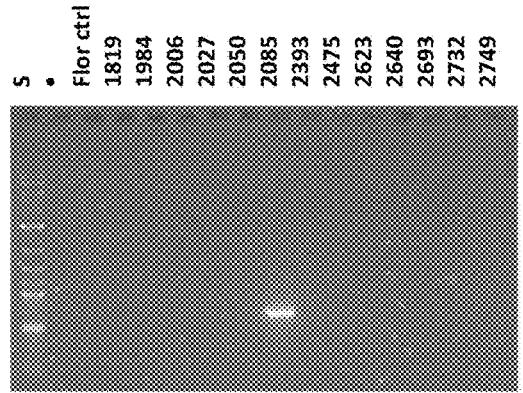
Figure 6I:
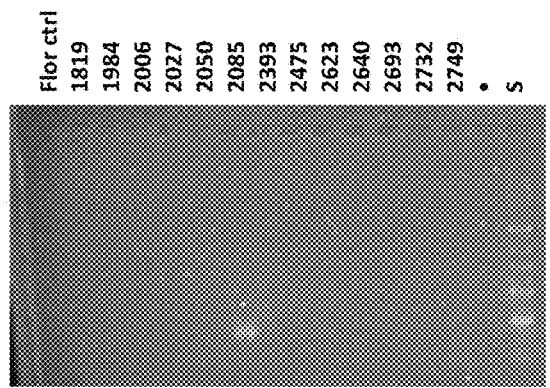
Figure 6J:
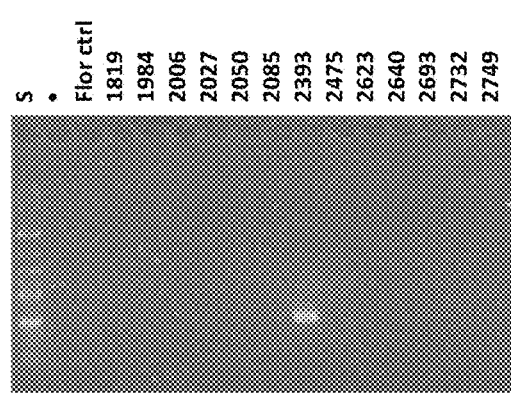
Figure 6K:
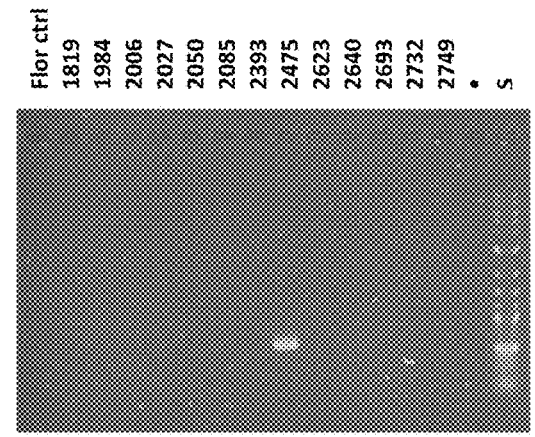
Figure 6L:
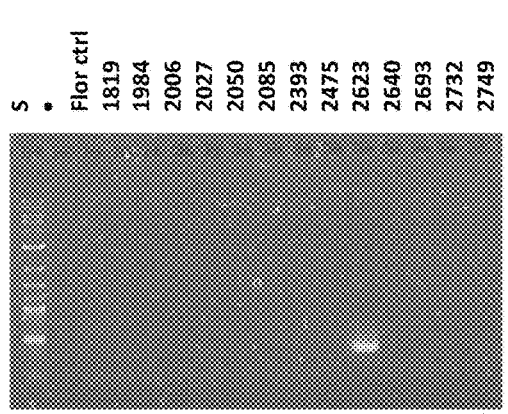

One embodiment of the TAIL-PCR method is summarized in the diagram of FIG. 5. As seen in the diagram, the foregoing TAIL-PCR procedure uses unequal concentrations of specific and random (degenerate) primers, the latter of which have a tail at one end that hybridizes to a tail-specific primer.

In some embodiments of the invention, the method of TAIL-PCR utilized to identify unknown portions of DNA involves the following steps:

a. Using PCR (polymerase chain reaction) to amplify a portion of DNA from a genomic template that spans two small target sequences homologous to precise primers, thereby creating a visible DNA fragment that can be cloned and sequenced.

b. Creating pairs of nested primers that match the ends of the transgene (Gene-Specific Primers, or "GSPs"), facing outward into the flanking DNA.
c. Creating a two-part primer consisting of an inner "degenerate" portion made of random primers of various sequences, and an outer "tail" portion. To increase the chances of the random primers finding a binding site in the native DNA near the integrated transgene, a series of 3 sets of degenerate primers are used, all of which are linked to the identical "tail" portion.
d. Creating a tail-specific primer that will bind to the "tail" portion of the two-part primer.

In one embodiment, the method of TAIL-PCR involves preparing genomic DNA from a transgenic plant to use as a template. The first PCR reaction uses a first nested gene-specific primer ("GSP1") combined with the degenerate tail-primer in a PCR reaction. This PCR reaction uses as a template the genomic DNA of the transgenic plant. The PCR reaction is done as a set of four, using one of each of the four degenerate tail-primers paired with a GSP1. The degenerate primers are provided in 3-fold excess over the GSP1. A different set of PCR reactions is done for each of both ends of the transgene (in this case, the EPSPS end and the GA2OX end), using the GSP1 primer designed for that end. The results of this first PCR reaction may then be detected using gel electrophoresis as a series of bands of all sizes, due to the random nature of the primers.

The second PCR reaction uses the "nested" gene-specific primer ("GSP2") paired with a primer that is specific for the tail portion of the degenerate primer ("TAIL primer"). This PCR reaction uses as a template the band (fragment) mixture that is produced from the first PCR reaction. This time, all four PCR reactions produced with different degenerate primers may be amplified with the TAIL-specific primer paired with GSP2 for that end. If a flanking sequence is recognized by any of the primer pairs, the results of this second PCR reaction should be detected using gel electrophoresis as a strong, visible band (fragment) that can be cloned and sequenced. One end of the sequence should contain the tail primer homology; the other end of the sequence should contain GSP2 homology; and in between should be native plant DNA that is flanking that end of the integrated transgene, and is likely to be a unique integration site for that transgenic event.

The below Table 3 and Table 4 provide a non-exhaustive list of gene-specific primers, degenerate, and TAIL primers that can be used in the TAIL-PCR embodiment described above:

TABLE 3

Gene-Specific Primers used for both Genomewalker ™ and TAIL-PCR methods

| Sequence No. | Primer | Primer name | Sequence: 5'-3' |
|---|---|---|---|
| (SEQ ID NO: 18) | GSP1 for HT end | PRU761 f1-1 | CATAATATCTTCGTCCCA TAGGTGTC |
| (SEQ ID NO: 40) | GSP2 for HT end | PRU761 f1-2 | CATGATCAACAAAATAA TCATCAGGTCG |
| (SEQ ID NO: 20) | GSP1 for DWF end | PGO761 f1-1 | GCATAGTTCTAGTTATCA GCGCTACATATATAAGG |
| (SEQ ID NO: 41) | GSP2 for DWF end | PGO761 f1-2 | CATTTTATATTTAGCACA CGTTCCCTATATTGTTAG |

TABLE 3-continued

Gene-Specific Primers used for both Genomewalker ™ and TAIL-PCR methods

| Sequence No. | Primer | Primer name | Sequence: 5'-3' |
|---|---|---|---|
| (SEQ ID NO: 42) | GSP1 for middle | ZD fwd | CACCTTTATCGTCAGTGT GTGGTCAGGTTTC |
| (SEQ ID NO: 16) | GSP2 for middle | Sp3 rev | GCAGAGACACAGAGCCT TCATTAACCAAACTTC |
| (SEQ ID NO: 43) | GSP1 for middle | Sp3fwd | GAAGTTTGGTTAATGAA GGCTCTGTGTCTCTGC |
| (SEQ ID NO: 44) | GSP2 for middle | ZDrev | GAAACCTGACCACACAC TGACGATAAAGGTG |
| SEQ ID NO: 45 | alternate GSP1 for HT end | PRUrev608 | GATGCCGTTTGCTCACGG CGGGGTTGGTG |
| SEQ ID NO: 46 | alternate GSP2 for HT end | PRUrev468 | GTACTGTGTACGATTACG ACGGAAGAAAACATA |
| SEQ ID NO: 47 | alternative GSP1 for DWF end | 415 GOB1 5-1 | GAATAATTTAACTTCATG ACAGAGATG |
| SEQ ID NO: 28 | alternative GSP2 for DWF end | 415 GOB1 5-2 | GAACGTATATTCTAAGCA ATAATGATTTC |

TABLE 4

Degenerate and TAIL Primers used herein for TAIL-PCR, based on Liu and Chen (2007)

| Sequence No. | Primer | Primer name | Sequence: 5'-3' |
|---|---|---|---|
| (SEQ ID NO: 48) | Degenerate 1 Primer | LAD1-1 | ACGATGGACTCCAGAGCGGCCGC (G/C/A)N(G/C/A)NNNGGAA |
| (SEQ ID NO: 49) | Degenerate 2 Primer | LAD1-2 | ACGATGGACTCCAGAGCGGCCGC (G/C/T)N(G/C/T)NNNGGTT |
| (SEQ ID NO: 50) | Degenerate 3 Primer | LAD1-3 | ACGATGGACTCCAGAGCGGCCGC (G/C/A)(G/C/A)N(G/C/A) NNNCCAA |
| (SEQ ID NO: 51) | Degenerate 4 Primer | LAD1-4 | ACGATGGACTCCAGAGCGGCCGC (G/C/T)(G/A/T)N(G/C/T) NNNCGGT |
| (SEQ ID NO: 52) | Tail-specific Primer | AC1 | ACGATGGACTCCAGAG |

Kits

Kits comprising any of the products (e.g., nucleic acid molecules, primers, probes, markers) described herein are also provided. In one aspect, the kit comprises any primer pair derived from SEQ ID NO: 1, SEQ ID NO: 2, SEQ ID NO: 3, SEQ ID NO: 4, SEQ ID NO: 5, (SEQ ID NO: 6, SEQ ID NO: 7), SEQ ID NO: 8, SEQ ID NO: 9, SEQ ID NO: 10, SEQ ID NO: 11, SEQ ID NO: 12, SEQ ID NO: 13, and/or SEQ ID NO: 14, that, in a DNA amplification reaction produces an amplicon diagnostic for St. Augustinegrass Ss026-1819, Ss026-1984, Ss026-2006, Ss026-2027, Ss026-2050, (Ss026-2085), Ss026-2393, Ss026-2475, Ss026-2623, Ss026-2640, Ss026-2693, Ss026-2732, and/or Ss026-2749, respectively. A kit may comprise any primer pair derived from the nucleotide sequence of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, or SEQ ID NO: 35. In another aspect, the kit comprises any primer pair derived from any of the genetic elements of plasmid pSCO761 diagnostic for events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749. In another aspect, the kit comprises any primer pair derived from SEQ ID NO: 36, SEQ ID NO: 37, SEQ ID NO: 38, or SEQ ID NO: 39.

In a particular aspect, the kit comprises one or more of the following primer pairs: Ss026-1819 event primer 1 (SEQ ID NO: 15) and Ss026-1819 event primer 2 (SEQ ID NO: 16); Ss026-1984 event primer 1 (SEQ ID NO: 17) and Ss026-1984 event primer 2 (SEQ ID NO: 18); Ss026-2006 event primer 1 (SEQ ID NO: 19) and Ss026-2006 event primer 2 (SEQ ID NO: 20); Ss026-2027 event primer 1 (SEQ ID NO: 21) and Ss026-2027 event primer 2 (SEQ ID NO: 16); Ss026-2050 event primer 1 (SEQ ID NO: 22) and Ss026-2050 event primer 2 (SEQ ID NO: 20); Ss026-2085 event primer 1 (SEQ ID NO: 23) and Ss026-2085 event primer 2 (SEQ ID NO: 20) (for SEQ ID NO: 6); Ss026-2085 event primer 1 (SEQ ID NO: 24) and Ss026-2085 event primer 2 (SEQ ID NO: 25)(for SEQ ID NO: 7); Ss026-2393 event primer 1 (SEQ ID NO: 26) and Ss026-2393 event primer 2 (SEQ ID NO: 20); Ss026-2475 event primer 1 (SEQ ID NO: 27) and Ss026-2475 event primer 2 (SEQ ID NO: 28); Ss026-2623 event primer 1 (SEQ ID NO: 29) and Ss026-2623 event primer 2 (SEQ ID NO: 30); Ss026-2640 event primer 1 (SEQ ID NO: 31) and Ss026-2640 event primer 2 (SEQ ID NO: 18); Ss026-2693 event primer 1 (SEQ ID NO: 32) and Ss026-2693 event primer 2 (SEQ ID NO: 33); Ss026-2732 event primer 1 (SEQ ID NO: 34) and Ss026-2732 event primer 2 (SEQ ID NO: 18); Ss026-2749 event primer 1 (SEQ ID NO: 35) and Ss026-2749 event primer 2 (SEQ ID NO: 18).

In another aspect, the kit comprises a DNA specific for the transgene/junction regions of events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749. In a particular aspect, the kit comprises a DNA molecule comprising SEQ ID NO: 1 (event Ss026-1819), SEQ ID NO: 2 (event Ss026-1984), SEQ ID NO: 3 (event Ss026-2006), SEQ ID NO: 4 (event Ss026-2027), SEQ ID NO: 5 (event Ss026-2050), SEQ ID NO: 6 (event Ss026-2085), SEQ ID NO: 7 (event Ss026-2085), SEQ ID NO: 8 (event Ss026-2393), SEQ ID NO: 9 (event Ss026-2475), SEQ ID NO: 10 (event Ss026-2623), SEQ ID NO: 11 (event Ss026-2640), SEQ ID NO: 12 (event Ss026-2693), SEQ ID NO: 13 (event Ss026-2732), SEQ ID NO 14 (event Ss026-2749), or combinations thereof In another aspect, the kit comprises a DNA probe that specifically hybridizes to a nucleic acid molecule set forth in SEQ ID NOs: 1, 2, 3, 4, 5, 6, 7, 8, 9, 10, 11, 12, 13, 14, complements thereof, fragments thereof, or combinations thereof, under standard stringency conditions.

Kits comprising any of the products (e.g., nucleic acid molecules, primers, probes, markers) described herein may include a solid support. The nucleic acid molecules, including but not limited to probes and primers, may be attached to a substrate. The nucleic acid molecules may be directly attached to the substrate or attached via a linker. The substrate includes but is not limited to smooth supports (e.g., metal, glass, plastic, silicon, and ceramic surfaces) as well as textured and porous materials. Substrate materials include, but are not limited to acrylics, carbon (e.g., graphite, carbon-fiber), cellulose (e.g., cellulose acetate), ceramics, controlled-pore glass, cross-linked polysaccharides (e.g., agarose or SEPHAROSE® (crosslinked, beaded-form of agarose), gels, glass (e.g., modified or functionalized glass), graphite, inorganic glasses, inorganic polymers, latex, mica, nanomaterials (e.g., highly oriented pyrolitic graphite (HOPG) nanosheets), nitrocellulose, NYLON® (aliphatic polyamides), optical fiber bundles, organic polymers, paper, plastics, polacryloylmorpholide, poly(4-methylbutene), poly(ethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON® (Polytetrafluoroethylene (PTFE)).

Substrates need not be flat and can include any type of shape including spherical shapes (e.g., beads) or cylindrical shapes (e.g., fibers). The nucleic acid molecules, including but not limited to probes and primers, may be attached to any portion of the solid support (e.g., may be attached to an interior portion of a porous solid support material).

Substrates may be patterned, where a pattern (e.g., stripes, swirls, lines, triangles, rectangles, circles, arcs, checks, plaids, diagonals, arrows, squares, or cross-hatches) is etched, printed, embedded, or layered onto a substrate. For example, the probes and primers described herein may be arranged in an array on a solid support (e.g., attached to the support in a pattern). The substrate can be substantially flat or planar. Alternatively, the surface can be rounded or contoured. Exemplary contours that can be included on a surface are wells, depressions, pillars, ridges, and channels.

The nucleic acid molecules, including but not limited to probes and primers, may be attached to a substrate through a stable chemical or physical interaction. The attachment may be through a covalent bond. However, attachments need not be covalent or permanent. For example, the materials may be attached to a substrate through a "spacer molecule" or "linker group." Such spacer molecules are molecules that have a first portion that attaches to the nucleic acid molecule and a second portion that attaches to the substrate. Thus, when attached to the substrate, the spacer molecule separates the substrate and the nucleic acid, but is attached to both. Methods of attaching nucleic acids to a substrate are well known in the art, and include but are not limited to chemical coupling.

Kits comprising any of the products (e.g., nucleic acid molecules, primers, probes, markers) described herein may be in a buffer or solution. For example, the probes and primers may be provided suspended in a buffer. The probes and primers described herein may be lyophilized.

The sequences disclosed herein, probes and primers, may be labeled. The label may be a chemiluminescent label, paramagnetic label, an MRI contrast agent, fluorescent label, bioluminescent label, or radioactive label.

Areas Comprising the Events

St. Augustinegrass events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and Ss026-2749, are tolerant to glyphosate herbicide and possess enhanced turfgrass quality. Grasses comprising these events are thus useful in various areas, e.g., a turfgrass stand. As such, the invention provides for turfgrass stands comprising St. Augustinegrass event event Ss026-1819, event Ss026-1984, event Ss026-2006, event Ss026-2027, event Ss026-2050, event Ss026-2085, event Ss026-2393, event Ss026-2475, event Ss026-2623, event Ss026-2640, event Ss026-2693, event Ss026-2732, and/or event Ss026-2749. The turfgrass stand may be cultivated in private and public areas. In a particular aspect, the turfgrass stand is grown or located on a sports field (e.g., golf course), home lawn or public ground. In another aspect, the invention provides for a turfgrass stand wherein at least 50%, 60%, 70%, 80%, 90%, 95%, 96%, 97%, 98%, 99%, or more of the turfgrass stand comprises St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749.

Turfgrass stands comprising events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749 can be effectively managed for weed control by the application of a glyphosate containing herbicide. As such, the invention provides for methods of controlling weeds in a turfgrass stand comprising applying an effective amount of glyphosate to a turfgrass stand comprising events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732, and/or Ss026-2749.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

The following examples show various embodiments of the invention. It should be appreciated by those of skill in the art that modifications can be made without departing from the spirit and scope of the invention.

EXAMPLES

Example 1

Creating and Selecting for Transgenic Plants

All transgenic St. Augustinegrass events were generated by microprojectile bombardment of St. Augustinegrass cv "Floratam" inflorescence-derived embryogenic callus material using a linear DNA fragment derived from pSCO761 (FIG. 1), the transgene insert of the invention, by digestion with the restriction enzyme MluI. This DNA fragment contains two transgene expression cassettes that confer glyphosate and enhanced turfgrass characteristics. The first cassette includes the rice ubiquitin promoter (P-Os.UBQ, also referred to as P-RUBQ) and rice actin 1 intron (I-Os.Act1, also referred to as R-Act intron) (see U.S. Pat. No. 5,641,876), operably connected to a glyphosate-tolerant 5-enol-pyruvylshikimate-3-phosphate synthase (EPSP synthase) from Arabidopsis and operably connected to a Zea mays alcohol dehydrogenase transcriptional terminator. The second transgene expression cassette includes the Os.GOS2 promoter, operably connected to gibberellic acid 2-oxidase from spinach (Lee et al., Plant Physiology (2005) 138: 243-254) and operably connected to a Solanum pennellii histone H1 gene transcriptional terminator.

Post-bombardment, glyphosate-tolerant transgenic calli were selected on media containing 1.0 mM glyphosate and plants were subsequently regenerated on media containing 0.1 mM glyphosate. Transgenic events were produced and plants containing the pSCO761 transgene fragment were selected from this population based on a superior combination of characteristics, including glyphosate tolerance and enhanced turfgrass quality.

Example 2

Identifying Nucleotide Sequences Adjacent to Trangene Using TAIL-PCR

The flanking sequence identifiers for Ss026-2006, Ss026-2050, Ss026-2475, Ss026-2623 and Ss026-2749 were identified using the TAIL-PCR method described above. Genomic DNA of each was purified from greenhouse-grown leaf tissue using the DNeasy® Plant Mini Kit (Qiagen Cat No 69106). DNA (approx. 50-100 ng) was used as a template for PCR, in a 20-µL volume reaction, using the Advantage® 2 PCR Kit (TaKara Bio USA, part 639207). Both the GA2OX and EPSPS ends of the gene were tested for flanking sequence identification. For each end, 4 PCR preactions were performed, each with a different degenerate (LAD) primer (Table 4) together with an outer-nested gene-specific primer (GSP1) (Table 3). Therefore, a standard TAIL-PCR test used 8 separate PCR reactions for each transgenic event. Each reaction contained: 1× Advantage® 2 PCR buffer, 200 µM mixed dNTPs, 1.0 µM degenerate primer, 0.3 µM GSP1, 0.5 units Advantage® 2 polymerase, ~50 ng genomic DNA template. The first PCR reaction used the following program, we call "TAIL1": 93° C.-2', 95° C.-1', 11×(94° C.-30", 60° C.-1, 72° C.-3'), 94° C.-30", 25° C.-2', ramping to 72° C. at 0.5° C./s, 72° C.-3', 26×(94° C.-20", 58° C.-1', 72° C.-3'), 72° C.-5', hold at 10° C. Then TAIL1 PCR reactions (~0.2 µL) were used as template for a second (TAIL2) reaction, which contained the inner-nested gene-specific primer (GSP2) (Table 3) and a primer (AC1) matching a conserved "tail" region present on all of the LAD primers (Table 4). Each reaction contained: 1× Advantage® 2 PCR buffer, 200 µM mixed dNTPs, 0.3 µM ea AC1 and GSP2 primers, 0.5 units Advantage® 2 polymerase, ~0.2 µL TAIL1 reaction. The second PCR reaction used the following program, we call "TAIL2": 2×(94° C.-20", 65° C.-1', 72° C.-3'), 14×(94° C.-20", 68° C.-1', 72° C.-3', 94° C.-20", 68° C.-1', 72° C.-3', 94° C.-20", 50° C.-1', 72° C.-3'), 72° C.-5', hold at 10° C. Then 5 µL each TAIL1 and corresponding TAIL2 reactions are resolved on a test gel. The desired result is a simple pattern of intense bands in TAIL2 each of which have a slightly larger counterpart in TAIL1, the likely template of nested priming to produce the stronger TAIL2 band. TAIL2 reactions showing promising bands are then resolved on a prep gel, and desired bands are excised, gel-extracted, and cloned into a TOPO vector (Invitrogen™ part no K450002, Thermo Fisher Scientific Inc.) and sent to a facility for sequencing.

A successfully cloned flanking sequence should have AC1 primer sequence at one end, GSP2 sequence at the other end, and a clear junction between pSCO761 transgene and native genomic DNA Example 3

Identifying Nucleotide Sequences Adjacent to Trangene Using Genomewalker™

The flanking sequence identifiers for Ss026-1819, Ss026-1984, Ss026-2027, Ss026-2085, Ss026-2393, Ss026-2640, Ss026-2693 and Ss026-2732 were identified using the Genomewalker™ method described above. Aliquots of ~2-3 μg genomic DNA were digested to completion with blunt-cutting restriction endonucleases. Some of the digests employed a single restriction endonuclease and sets of libraries were prepared, each using a single enzyme. Alternatively, 2 or more enzymes were used, to prepare a library of smaller fragments. Digested DNA was then purified away from the digest buffers using either a gel/PCR column cleanup method (Macherey-Nagel Co., Cat No 740609) or a silica resin precipitate binding method (GeneClean® II kit, MP Biomedicals LLC-USA, Cat No 111001400), and collected in a total of 25 μL nuclease-free water or buffer. Then 5 μL digested, purified DNA was used in a 8-4, total volume ligation to 1.9 μL 25 μM stock of Genomewalker™ double-stranded adaptor at 16° C. for at least 16 H. The resulting mixture of genomic DNA fragments attached to adaptor DNA was diluted to 40 μL with TE buffer, pH 8.0, creating the final Genomewalker™ library. Sometimes two separate ligations were used to prepare replicate libraries, to rule out bands produced by ligation artifacts. PCR was conducted using 1 μL library as template, using the Advantage® 2 PCR Kit (TaKara Bio USA, part 639207) in 20- or 25-μL volumes, using the following program we call "FLANK": 7×(94° C.-25", 72° C.-3'), 32×(94° C.-25", 67° C.-3'), 1×(67° C.-6'), and using the outer nested gene-specific primer and outer nested adaptor primer 1 (AP1). Afterward, this PCR reaction (~0.2 μL) is used as a template for a second PCR reaction we call "FLANK2", using the inner-nested gene-specific primer and inner-nested adaptor primer 2 (AP2). PCR is conducted the same way, but this time using the following program: 5×(94° C.-25", 72° C.-5'), 20×(94° C.-25", 67° C.-3'), 1×(67° C.-7'). Afterward, 5 μL each of FLANK and FLANK2 PCR reactions are resolved together by electrophoresis, to analyze the fragments. Ideally, the FLANK2 reaction showed a small number of intense bands, each of which had a slightly larger counterpart in the corresponding FLANK reaction, reflecting its immediate progenitor produced by the outer-nested primers. If duplicate libraries were produced, only bands that were consistent with both are of importance, regardless of intensity. FLANK2 reactions showing promising bands were then resolved on a prep gel, desired bands are excised, gel-extracted, and cloned into a TOPO vector (Invitrogen™ part no K450002, Thermo Fisher Scientific Inc.) and sent to a facility for sequencing.

A successfully-cloned fragment should show the AP2 sequence joined to a site for the blunt-cutting endonuclease used to cut the genomic DNA. On the other end should be the gene-specific inner-nested primer. In between should be genomic DNA joined to that end of the pSCO761 construct.

If identifying a flanking sequence adjoining the GA2OX or EPSPS cassette ends was not successful, and Southern data suggested possible truncated fragment insertions, then a second set of FLANK1 and FLANK2 PCR reactions was performed on the Genomewalker® library of that event, this time using two pairs of nested primers located near the center of the sequence of pSCO761, where the EPSPS and GA2OX genes are joined at their 3'UTR ends. One nested pair (ZD fwd and Sp3 rev) (Table 3) reflect the scenario of a transgene insertion truncated to where most of the GA2OX cassette is missing. Another nested pair (Sp3fwd and ZDrev) (Table 3) reflect the scenario of a transgene insertion truncated to where most of the EPSPS cassette is missing.

Example 4

Verification of Flanking Sequences Using PCR Test for Genomic Contiguity and Event Specificity Once sequence analysis of a fragment produced via TAIL-PCR or Genomewalker® deemed a fragment to be a candidate for a flanking sequence, two or three 20-30 bp oligonucleotides matching the genomic DNA portion were ordered, and used as PCR primers paired with a transgene-specific oligonucleotide matching a region outside the GSP2 sequence, usually GSP1. Then, a PCR reaction was performed against genomic DNA samples of various independent ETQ St Augustinegrass events, including the "target" event. Genomic DNA (approx. 50 ng) was used as a template in 25-4, volumes of PCR reaction mix (GoTaq® Flexi DNA Polymerase, Promega Corporation, part no M8295) containing: 1×PCR buffer, 0.625 units Taq polymerase, 0.2 mM dNTPs, 1.5 mM MgCl2, 0.2 μM each primer. The PCR program for amplifying a fragment of 1 kb expected length: 95° C.-5', 40×(94° C.-18", 60° C.-35", 72° C.-1'30"), 72° C.-10', 10° C.-hold.

A result that confirms the sequence to be a flanking identifier for an event is:

A band of expected size amplified out of genomic DNA for that particular transgenic event No similar band produced out of any other transgenic event tested The band product was then sent for sequencing to verify its identity with the original clone. Furthermore, the oligonucleotides used in the test for event specificity (one from the genomic DNA and one from the transgene) were designated as be the screening tools for PCR-identification of this event. If more than one oligonucleotide selected from the genomic sequence was effective in amplifying an event-specific band when paired with the transgene-specific oligonucleotide, one was selected, usually which produced the smallest effective band.

Example 5

Identifying a Nucleotide Sequence Flanking the Transgene in Event Ss026-1819

Event: Ss026-1819; Sequence name: 1819 ZS Sn 1 (SEQ ID: NO 1).
Method: Genomewalker®
Enzyme(s) for creating Genomewalker® library: FspI, NruI, SnaBI
Nested primers (GSP1, GSP2): ZD fwd, Sp3 rev
Date of identification: Dec. 17, 2015
Sequence of 1819 ZS Sn 1 (SEQ ID NO: 1)(1114 bp); Italicized is genomic DNA, non-italicized is transgene, underlined are primers 1819 ZS Sn 1 3-1 (SEQ ID: NO 14) and Sp3rev (SEQ ID: NO 15):

```
GGTCCTTTATAGGGAAAGCATATCATAGAGAATTCTAATTCTCATATATC

ATATAGGGTAGGTTGTGGTATTTCATTGCTACAAACATGTCTTATTTTAC

AATAAGACATGTCATTTGGATACTTCTCTTCAACTTCGAAGTATTTTGAT

ACAAATAGTTATAGTTGAAGTTAATTTTACGAAAGAAAATAAGGCGGATT

ATGGGAGTGTGTGACTTGAATTATTAATTCGGCCATGCAGATAGAGAATT

GGGCTCCCCGACCCCGAACTGCCTCTCCCAGCTCTCCTGGTCCGAGGCCT
```

-continued

TCCACATCCCGATGAACGACATCTGCTCCAACGCCCCGAGGAACATTGCC

AACGGTAACCCGAACATCTCCAACCTCTGCTCCACCGTGAAGCAGTTCGC

CACCACCGTGTCCGAGCTGGCCAACAAGCTCGCCAACATCCTCGTCGAGA

AGCTCGGCCATGACGAGCTGACCTTCATCGAGGAGAAGTGCTCCCCGAAC

ACGTGCTACCTCAGGATGAACCGCTACCCGCCGTGCCCAAAGTACTCCCA

CGTGCTCGGCCTCATGCCACATACCGACTCCGACTTCCTCACCATCCTCT

ACCAGGACCAGGTGGGCGGCCTCCAGCTCGTGAAGGACGGCCGCTGGATT

TCCGTGAAGCCGAACCCAGAGGCCCTCATCGTGAACATCGGCGACCTCTT

CCAGGCCTGGTCTAACGGCGTGTACAAGTCCGTGGTGCATAGGGTGGTGG

CCAACCCGAGGTTCGAGAGGTTCTCTACCGCCTACTTCCTCTGCCCGTCC

GGCGACGCCGTGATCCAGTCCTACCGCGAGCCGTCTATGTACCGCAAGTT

CAGCTTCGGCGAGTACAGGCAGCAGGTCCAGCAGGACGTGCGCGAGTTCG

GCCACAAGATCGGCCTCTCCCGCTTCCTCATCTGCAACGAGCTCGAATTC

GCATGGCGTGGGATAATACAGACTGTATATAGGAGGAATAATGGTTTGCT

GCTTGTAGCTCTGTAAATAGGAAAATGAAGCTCAGCTTTTACTTTCAGTC

ATCTAGTTCGGTAGTGTAGGCCGGGTTTGCT<u>GAAGTTTGGTTAATGAAGG

CTCTGTGTCTCTGC</u>

Example 6

Identifying a Nucleotide Sequence Flanking the Transgene in Event Ss026-1984

Event: Ss026-1984
Sequence name: 1984 RU FNS (SEQ ID NO: 2)
Method: Genomewalker®
Enzyme(s) for creating Genomewalker® library: FspI, NruI, SnaBI
Nested primers (GSP1, GSP2): PRU 761 fl-1, PRU 761 fl-2
Date of identification: Sep. 16, 2016
Sequence of 1984 RU FNS 1 (SEQ ID NO: 2)(230 bp); Italicized is genomic DNA, non-italicized is transgene, underlined are primers 1984 RU FNS 1 3-2 (SEQ ID NO: 16) and PRU 761 fl-1 (SEQ ID NO: 17):

<u>*TGGCTGGACAGGGATTTCGTGACT*</u>*GGGTTCCACGAGGGGAAGAAGAAAAG*

*AAGAAAGGAAGCACAGAAGATGTTGCAGGAGAAGGAGGGGAAGAACAGAA*

*TCGTGGTACCGCGGCCGCAAGCTTGTCGACCTGATGATTATTTTGTTGAT*

*CATGATTTTCTTTTGGCTATTTGATTTTTTGAAAGATATTTTTTTCCCTG*

*GGAAG*<u>ACACCTATGGGACGAAGATATTATG</u>

Example 7

Identifying a Nucleotide Sequence Flanking the Transgene in Event Ss026-2006

Event: Ss026-2006
Sequence name: 2006 TAIL GO 1 (SEQ ID NO: 3)
Method: TAIL-PCR
Nested primers (GSP1, GSP2): PGO 761 fl-1, PGO 761 fl-2
Date of identification: Jul. 15, 2015

Sequence of 2006 TAIL GO 1 (SEQ ID NO: 3)(669 bp); Italicized is genomic DNA, non-italicized is transgene, underlined are primers 2006 TAIL GO 1 3-1 (SEQ ID NO: 18) and PGO 761 fl-1 (SEQ ID NO: 19):

<u>*ATCCACATGTGCATCTCGTTATGGCCTGGGT*</u>*GCCTGGCCATTCTTTTGTT*

*GCATTGCATTGCCACCTACCGTGCGTGCTTATATTAGTTAGAGTAAGTTG*

*ATTAAACTACTTAGCTCGTCAAATAATGCGCGTCTGAGCGCCGCTTGCCA*

*GGAGAATTAAGTATGTGTCAATGGGCAACAATCAACGAGAGGTGGGACAT*

*GCTGTTCGGTCTTGTGTCCTGATCCGCCCGTTTGTATTGTTTGTTTATAT*

*GCAGTTAATTATGCGGTCTCGAGAGCGAGTATTGTAATCGCAAGAGGTTG*

*CAGCCAGCACTACCGCCGATATCTTGTTAGAGGTCGCAGTAACCTGCTGG*

*TAGGAGTAGGACTGTAGGAGTAACATGGTAAGTGGACTCCTCATCTTGTT*

*GTATCCGGCGTCCTGTACAGTGTACAGTACAGCTTGGGCAAAGGCCCAAA*

*GAGATTCCGTCGTGGCGATGGCGATCCGGATCCATCGAGCGCACGACACT*

*TGACAGGTCGCACCTTGCAGGCCCGTCAATAATTTGTACCGCGGCCGCAA*

*GCTTTCTAGAATCCGAAAAGTTTCTGCACCGTTTTCACCCCCTAACTAAC*

*AATATAGGGAACGTGTGCTAAATATAAAATGAGA*<u>CCTTATATATGTAGCG

CTGATAACTAGAACTATGC</u>

Example 8

Identifying a Nucleotide Sequence Flanking the Transgene in Event Ss026-2027

Event: Ss026-2027
Sequence name: 2027 ZS 2 (SEQ ID NO: 4)
Method: Genomewalker®
Nested primers (GSP1, GSP2): ZD fwd, Sp3 rev
Date of identification: Jul. 15, 2015
Sequence of 2027 ZS 2 (SEQ ID NO: 4)(482 bp); Italicized is genomic DNA, non-italicized is transgene, underlined are primers 2027 ZS2 3-1 (SEQ ID NO: 20) and Sp3 rev (SEQ ID NO: 15):

<u>*CTTAGGTGGAAGGCGAAGAAGGCCCCCTT*</u>CCGGGCAGAGGCCCTCATCGT

GAACATCCGCGACCTCTTCCAGGCCTGGTCTAACGGCGTGTACAAGTCCG

TGGTGCATAGGGTGGTGGCCAACCCGAGGTTCGAGAGGTTCTCTACCGCC

TACTTCCTCTGCCCGTCCGGCGACGCCGTGATCCAGTCCTACCGCGAGCC

GTCTATGTACCGCAAGTTCAGCTTCGGCGAGTACAGGCAGCAGGTCCAGC

AGGACGTGCGCGAGTTCGGCCACAAGATCGGCCTCTCCCGCTTCCTCATC

TGCAACGAGCTCGAATTCGCATGGCGTGGGATAATACAGACTGTATATAG

GAGGAATAATGGTTTGCTGCTTGTAGCTCTGTAAATAGGAAAATGAAGCT

CAGCTTTTACTTTCAGTCATCTAGTTCGGTAGTGTAGGCCGGGTTTGCT<u>G

AAGTTTGGTTAATGAAGG</u>CTCTGTGTCTCTGC

Example 9

Identifying a Nucleotide Sequence Flanking the Transgene in Event Ss026-2050

Event: Ss026-2050
Sequence name: 2050 TAIL GO 1 (SEQ ID NO: 5)
Method: TAIL-PCR
Nested primers (GSP1, GSP2): PGO 761 fl-1, PGO 761 fl-2
Date of identification: Jul. 15, 2015
Sequence of 2050 TAIL GO 1 (SEQ ID NO: 5)(790 bp); Italicized is genomic DNA, non-italicized is transgene, underlined are primers 2050 TAIL GO 1 3-3 (SEQ ID NO: 21) and PGO 761 fl-1 (SEQ ID NO: 19)":

GTTGACGTGCGTACGAACAAACGAGTTTCAGCAACGGCCGTCGGTGCTTC
GTGCGTGCTCTTGTCCATCTCTGTCTGTCACTCATCTATAATTTAATTAA
TTTGCTGCACACAATTTAATTATATATCACTTTTACCAACGGCTAACCAC
CTGCATGAGTACGTGTCTTTGTTTGTGGCTGCACTCTCCTGTGGGAAGA
TTACTAGAAGGATCCTGCTGCTGCTAGTATCATATCATATATCGACGATG
GACGGACGGATACGATGTTTAATTGCCTGATAAGCACTCACATCCAACCC
CCAAACCCTCGCTGACACTGAATGGATTGAATTCGGCCTCCAAATCCAGC
TGCTGCAAATCAGTCCTGTTAGGCGGCCGCTGCTAATTCTTCAATACTAC
TCCAATACTCCTACGGTACTGTGTACAATTCAATTCAATTCACCCTGCTG
CTGCTGCCTCAACTACGAGCATAGCATGCATCATCTAGCCTGCTGCCGGC
CCAACTCCCAACTACCTGCAGCCGGTCTCTTAATTCCCATTCCATCGAGG
CCGACACCAACGACAGGGATCCACCGACGACCGAAACTGCTGGACACCAT
GCCCATGGCCATGCATGCACCCATCATCAGCTAGCACCTCCGATCCCCAG
GCCATCTCAGCTCCGTCCTCGTCAGTCATCGCTCGTCACAAACCACGCAC
CGTTTTCACCCCCTAACTAACAATATAGGGAACGTGTGCTAAATATAAAA
TGAGACCTTATATATGTAGCGCTGATAACTAGAACTATGC

Example 10

Identifying Two Nucleotide Sequences Flanking Regions Adjacent the Transgene Insertions in Event Ss026-2085

Event: Ss026-2085
Sequence name: 2085 GO Sn 1 (SEQ ID NO: 6)
Method: Genomewalker®
Enzymes used to create Genomewalker® library: FspI, NruI, SnaBI
Nested primers (GSP1, GSP2): PGO 761 fl-1, PGO 761 fl-2
Date of identification: Sep. 28, 2016
Sequence of 2085 GO Sn 1 (SEQ ID NO: 6)(678 bp); Italicized is genomic DNA, non-italicized is transgene, underlined are primers 2085 GO Sn 1 3-2 (SEQ ID NO: 22) and PGO 761 fl-1 (SEQ ID NO: 19):

GAGCCGACTCATGCCTAATGCTTCTCTAGATTCGAAACATTGATCTCAAT
GTGATATCTTTATAACTTGATATTTTGACTATAGACCCTTCAATGAAAAA
GCTCAACCTCCAGAGGGTGTAGTACCAGGCATCAAACATGGACTGGCAAG
GGAGCTTTTGAGCTCACTGCTCTGACCAGTATAATGCGTGCAAAGATGGT
AGCTCTTTAGTGAACTCTTTGTTATATGAAACAACCAATACTTGCTTGGT
AGTAGACCTGATCATTTTTGGGTCGTGCCGAGCCGAAAAAAGCCTAGTT
GATTTTGGACCAAAGATTCGTTCTTGCGGCTGTCCCACGGGCTTTGTCGA
CTGGGCTCTTTTTTAGTTGAAAATAAATCAAATAAATTGTCTGGGCAGAC
TCGAACCAACCTGATTTTTTTTGGGCTTGGTTTTCGCTAAACGCACCCAA
TCCTATAGGCATCATGAGTGGGCAAATCCTAGTGGACTTGAAGGCCCAT
GGGCTGGGCGGGCTGGGCCAAAAAATTCTCAGGTATACTTGGTAGCCATC
TCTCCTGAAGTTGTCGTATTTCCGAAAAGTTTCTGCACCGTTTTCACCCC
CTAACTAACAATATAGGGAACGTGTGCTAAATATAAAATGAGACCTTATA
TATGTAGCGCTGATAACTAGAACTATGC

Event: Ss026-2085
Sequence name: 2085 SZ Sn 1 (SEQ ID NO: 7)
Method: Genomewalker®
Enzymes used to create Genomewalker® library: FspI, NruI, SnaBI
Nested primers (GSP1, GSP2): Sp3fwd, ZDrev
Date of identification: Sep. 28, 2016
Sequence of 2085 SZ Sn 1 (SEQ ID NO: 7) (358 bp); Italicized is genomic DNA, non-italicized is transgene, underlined are primers 2085 SZ Sn 1 3-2 (SEQ ID NO: 23) and 2085 SZ Sn 1 5-1 (SEQ ID NO: 24):

TATTACAGCGCCTTCTAATAATGTCAGTAAGCCAACCACCCGGGTGGACA
TATGAGCATCCCAGAAATGGTGTAAACTGTTAACTTACAAAGGCATACCT
TCGTACTTTTTAGGGGAAAAAGACTCTACGCTCTGCTGTTCTTTTGAGCC
CCAACTAGCGTGAACTCAAGCTGACTGAGTCCGCAACGCCAACATCTCCG
ACCCACCGTTCGAGGAGACCTACAAGAACCTCCTGCTCAAGCACAACATC
ACCCCGCTCACCACCACCACGACCACGACGACCACCACGGCGACCATCGA
GGTGAGGGATCTCCCACTCATCGACCTCTCCAGGCTCGTGGCCACCGCCG
CCAAGGAG

Example 11

Identifying a Nucleotide Sequence Flanking the Transgene in Event Ss026-2393

Event: Ss026-2393
Sequence name: 2393 GO Sn 1 (SEQ ID NO: 8)
Method: Genomewalker®
Enzymes used to create Genomewalker® library: FspI, NruI, SnaBI
Nested primers (GSP1, GSP2): PGO761 fl-1, PGO 761 fl-2
Date of identification: Jun. 21, 2016
Sequence of 2393 GO Sn 1 (SEQ ID NO: 8) (551 bp); Italicized is genomic DNA, non-italicized is transgene, underlined are primers 2393 GO Sn 1 3-2 (SEQ ID NO: 25) and PGO 761 fl-1 (SEQ ID NO: 19):

*CGGTGCGCCTTCGCCCACTTTCGGTTAGTTCGGTTGGTTTATCAACCACC*

*GGTCAATAGTATTTTTCTCTCATAATAAATCAGTACCAGCTATCGATTAT*

*TAACCAACCAGTAGTATTTTTCTCTCACAACAAATCAGCACCAACAACCA*

*ACCAACCGAAAAGAGTTTTTTTTCCGCTGCCGGTGGGCCCACTCCCATCT*

*AGTTGCACCACGCACGCCCCCAGCGAGCGTAGTTGACTCGTATTGCAGCC*

*ACGAAACGAGGCCCCCACCCTTCCTTCCTTTTTTTTGCTATCCACCCGC*

*AACGAGAGGCCAGGAGCGGCCGCCAAATATCTTCTATACGCCCCGCGATC*

*TCTACCGCCCCGACAAAATAAAAATCGCGCACCAAAATATCTCCCCCGCC*

*GGAGGGAGCACGAGATGGTACCGCGGCCGCAAGCTTTCTAGAATCCGCAA*

*AGTTTCTGCACCGTTTTCACCCCCTAACTAACAATATAGGGAACGTGTGC*

*TAAATATAAAATGAGA*<u>CCTTATATATGTAGCGCTGATAACTAGAACTATG</u>

<u>C</u>

Example 12

Identifying a Nucleotide Sequence Flanking the Transgene in

Event Ss026-2475
Event: Ss026-2475
Sequence name: 2475 TAIL GO 1 (SEQ ID NO: 9)
Method: TAIL-PCR
Nested primers (GSP1, GSP2): PGO761 fl-1, PGO 761 fl-2
Date of identification: Oct. 16, 2015
Sequence of 2475 TAIL GO 1 (SEQ ID NO: 9) (571 bp); Italicized is genomic DNA, non-italicized is transgene, underlined are primers 2475 TAIL GO 1 3-2 (SEQ ID NO: 26) and 415 GOBI 5-2 (SEQ ID NO: 27):

<u>CTCGCGACATCCGAAAACTAGAGGA</u>CAAAAAGAGTCAGATCGGAGAGTTG

ATTGGATTGGATGAGTTTGATGGCCGCGAAGGCATCGGTTTGGATTCCCC

AGATTACCAATTCAGTCTATGGCTGTCTCCAAGATGTCATGATACAACAA

TCAAGCACGAACCATCAGCATAGCATAGGTCCTTCCATAGTTCTGTCGCA

ATCAGCAGCTTTCTGTACCATGCCAGTACGTTGTAGCAAAGACAAGTTTT

TGTTTTGTACACCTGCTGATGTGTTTTGTAACCGTCGTTGTAGGACCAGT

TGTCTGATAGTGGTACCGCGGCCGCAAGCTTTCTAGAATCCGAAAAGTTT

CTGCACCGTTTTCACCCCCTAACTAACAATATAGGGAACGTGTGCTAAAT

ATAAAATGAGACCTTATATATGTAGCGCTGATAACTAGAACTATGCAAGA

AAAACTCATCCACCTACTTTAGTGGCAATCGGGCTAAATAAAAAGAGTC

GCTACACTAGTTTCGTTTTCCTTAGTAATTAAGTGGGAAAAT<u>GAAATCAT</u>

<u>TATTGCTTAGAATATACGTTC</u>

Example 13

Identifying a Nucleotide Sequence Flanking the Transgene in Event Ss026-2623

Event: Ss026-2623
Sequence name: 2623 TAIL GOBI 1-3 (SEQ ID NO: 10)
Method: TAIL-PCR
Nested primers (GSP1, GSP2): 415 GOBI 5-1, 415 GOBI 5-2
Date of identification: May 11, 2017
Sequence of 2623 TAIL GO 1 (SEQ ID NO: 10) (345 bp); Italicized is genomic DNA, non-italicized is transgene, underlined are primers 2623 GOBI 1-3 D (SEQ ID NO: 28) and 761 EPJ 5-2 (SEQ ID NO: 29):

<u>ATGCTTCAAGCTGGTCAGATCCG</u>TAAGTTTCCTCTCATAAACCCCAGCGA

AGAAATACTGATGGAACTGCTTCTCCAAATCGGCCCAAGTTATGATGGAA

TTGGCCGGAAGTGAAGTAAACCAAGCAAAGGCTGGACCAGACAAAGATGA

TGAAAACAGCCTGACTCTAAGCTCATCTTGCATAGCTGCCTCTCCACACT

GAATAATGAATTTATTGATGTGCTCAACTGTGGAGGTTTCGTTTATAGTG

CCCTTTTCCCCTCTTCCTGATCTTGTTTAGCATGGCGGAAATTTTAAACC

CCCCATCATCTCCCCCAACAA<u>CGGCGGATCGCAGATCTACATCCG</u>

Example 14

Identifying a Nucleotide Sequence Flanking the Transgene in Event Ss026-2640

Event: Ss026-2640
Sequence name: 2640 RU Fs 1 (SEQ ID NO: 11)
Method: Genomewalker®
Enzyme(s) used to create library: FspI, NruI, SnaBI
Nested primers (GSP1, GSP2): PRU761 fl-1, PRU 761 fl-2
Date of identification: Jun. 23, 2016
Sequence of 2640 RU Fs 1 (SEQ ID NO: 11) (572 bp); Italicized is genomic DNA, non-italicized is transgene, underlined are primers 2640 RU Fs 1 3-1 (SEQ ID NO: 30) and PRU761 fl-1 (SEQ ID NO: 17):

<u>GTATTTTGGACGAGCATACTGCATACA</u>ATAATACTTTGGTTGCTCATATCA

TTTGATTCGTATATGGGGTGGTGTGAAATAATGATAATTTTTTTGTTTGG

TTAGGTGAACTGTACCATCCCATCTAAAATGAAGTTATCTCACCTAATAT

TTTTTCTGCTAATAAAAATGAATCATATAATTCAAGTAACTTGGTTGAAC

CCTCCGTTCAAAATCATCTCATACATGCATCACATGATGATTGCACCAAA

CACACCCTCCGCCGCGTTAATGCCGGAGATTACTGGAGAAACTGAAGAAA

AGAAAGGGAGAGGGGAGTCGAGCTCTGGGCCGCCAAAACCCTTTGCTCCG

TTGATTCAGGCCCAACATGGAAATGGGCTAGGCCAGCGACGACTTGTGAC

GAAAAGCGGAATTCCGGACAACTGGGCGCATGTGGTCCAAACAAAGGATA

CCGCGGCCGCAAGCTTGTCGACCTGATGATTATTTTGTTGATCATGATTT

TCTTTTGGCTATTTGATTTTTTGAAAGATATTTTTTTCCCTGGGA<u>AGACA</u>

<u>CCTATGGGACGAAGATATTATG</u>

Example 15

Identifying a Nucleotide Sequence Flanking the Transgene in Event Ss026-2693

Event: Ss026-2693
Sequence name: 2693 RU Snl 3-5 (SEQ ID NO: 12)
Method: Genomewalker®
Enzyme(s) used to create library: FspI, NruI, SnaBI
Nested primers (GSP1, GSP2): PRU761 fl-1, PRU 761 fl-2
Date of identification: Nov. 3, 2016
Sequence of 2693 RU Snl (SEQ ID NO: 12) (358 bp); Italicized is genomic DNA, non-italicized is transgene, underlined are primers 2693 RU Sn 1 3-5 (SEQ ID NO: 32) and PGG2 rev (SEQ ID NO: 33):

GAAGTACAAACTGTCCAAAAAATAGAATGAAGATATTCTGAACGTATTGG

CAAAGATTTAAACATATAATTATATAATTTTATAGTTTGTGCATTCGTCA

TATCGCACATCATTAAGGACATGTCTTACTCCATCCCAATTTTTATTTAG

TAATTAAAGACAATTGACTTATTTTTATTATTTATCTTTTTTCGATTAGA

TGCAAGGTACTTACGCACACACTTTGTGGTCATGTGCATTTGTGAGTGCA

CCTCCTCAATACAAGTTCAACTAGCAACACATCTCTAATATTACTCGCCT

ATTTAATACATTTAGGTAGCAATATCTGAATTCAAGCACTCCACCATCAC

CAGACCAC

Example 16

Identifying a Nucleotide Sequences Flanking the Transgene in Event Ss026-2732

Event: Ss026-2732
Sequence name: 2732 RU Fs 1 (SEQ ID NO: 13)
Method: Genomewalker®
Enzyme(s) used to create library: FspI, NruI, SnaBI
Nested primers (GSP1, GSP2): PRU761 fl-1, PRU 761 fl-2
Date of identification: Jun. 23, 2016
Sequence of 2732 RU Fs 1 (SEQ ID NO: 13) (683 bp); Italicized is genomic DNA, non-italicized is transgene, underlined are primers 2732 RU Fs 1 3-2 (SEQ ID NO: 31) and PRU 761 fl-1 (SEQ ID NO: 17):

CGGCCTGTTTATCTTTGGACTATGTCCAACAGAGCCATGTGGTTCAATGT

TCATCGCTATCGTGACAAGCGTTGTCATGGTAATGAGGTTCCCAAGATCA

TGTTGCTTGATGTTCATACTGGAAGTGCAGAAACTCATGGGAGGTTTGAA

GTCGTAGTTTGGACATCACGCATACCCCCGTACCACAGCTACCTGGTGAG

CTGCGAGATGGGGCACCAATTCTGATGGCCAAGAAGAAGCGGCCTCACT

CCACGGTGTGATTCAAACTCATCTGCAGATACCAACACGATGTAACTGTC

TCTGTTCATCAACAATTTTAATTTCATTGCTGGAGTCAGTTTAACATGTT

ACAAGTTGCCAGACATTATCTGAAATTTTTTCTTAATTTGCAGTTGGCAG

GGACAATATGTAATGAATGAGGCTATCCATGGACACACTGGTAGCAGCAG

ATGATGCTTGCATCTGCAGACGGCGTGCCCTCTCCCTCATCAGAGCTTGG

AGCGAAATAACATCTGGCTCTACTTTAGTGGTACACAGGGTACCAGGGCA

AGTGAGCGGTACCGCGGCCGCAAGCTTGTCGACCTGATGATTATTTTGTT

GATCATGATTTTCTTTTGGCTATTTGATTTTTTGAAAGATATTTTTTTCC

CTGGGAAGACACCTATGGGACGAAGATATTATG

Example 17

Identifying a Nucleotide Sequences Flanking the Transgene in Event Ss026-2749

Event: Ss026-2749
Sequence name: 2749 RUrev468 1-2 (SEQ ID NO: 14)
Method: TAIL-PCR
Nested primers (GSP1, GSP2): PRUrev608, PRUrev468
Date of identification: May 11, 2017
Sequence of 2749 RUrev468 1-2 (SEQ ID NO: 14) (172 bp); Italicized is genomic DNA, non-italicized is transgene, underlined are primers 2749 RU468 1-2 3-3 (SEQ ID NO: 32) and PRU761 fl-1 (SEQ ID NO: 17):

TGGAGGAAGAGAAGATAGAGAGAATCACCCCCACGTGCTTGCGCTGCGGG

CGCTCGGAAGAAGAATTTGACGGTTGCAGCCCGGAAAGGGCGAAAGGGAA

AAGGGAAAAGGGTACGGTGTAGGTTCCCACGATCTTTCCCTGGGAAGACA

CCTATGGGACGAAGATATTATG

Summary of Data from Examples 1-17

Tables 5 and 6 below summarize the molecular data of St. Augustinegrass events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 and Ss026-2749 compared to St. Augustinegrass "Floratam" events. The St. Augustinegrass events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 and Ss026-2749 showed superior field performance (see Example 11). The table shows the estimated number of transgene copies inserted into the genome of St. Augustinegrass events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 and Ss026-2749 based on band count from Southern hybridization of genomic DNA digested with either BamHI or PstI. As described in Examples 1-10 above, the flanking sequences were identified using either GenomeWalker (as described in the Clontech Universal GenomeWalker™ Kit (Takara Bio USA, part no 636405) or TAIL-PCR (using a protocol substantially similar to that described in Liu & Chen [2007]).

TABLE 5

Summary of the St. Augustinegrass events compared to St. Augustinegrass "Floratam" events.

| line | # bands EP | # bands 2OX | Seq identifier name | Method |
|---|---|---|---|---|
| Ss026-1819 | 2 | 2 | 1819 ZS Sn 1 | Genomewalker |
| Ss026-1984 | 3 | 1 | 1984 RU FNS | Genomewalker |
| Ss026-2006 | 5 | 3 | 2006 TAIL GO 1 | TAIL PCR |

TABLE 5-continued

Summary of the St. Augustinegrass events compared to St. Augustinegrass "Floratam" events.

| line | # bands EP | # bands 2OX | Seq identifier name | Method |
|---|---|---|---|---|
| Ss026-2027 | 2 | 2 | 2027 ZS 2 | Genomewalker |
| Ss026-2050 | 3 | 2 | 2050 TAIL GO 1 | TAIL PCR |
| Ss026-2085 | 7 | 9 | 2085 GO Sn 1 | Genomewalker |
| Ss026-2085 | 7 | 9 | 2085 SZ Sn 1 | Genomewalker |
| Ss026-2393 | 5 | 2 | 2393 GO Sn 1 | Genomewalker |
| Ss026-2475 | 10 | 5 | 2475 TAIL GO 1 | TAIL PCR |
| Ss026-2623 | 2 | 3 | 2623 TAIL GOB1 1-3 | TAIL PCR |
| Ss026-2640 | 15 | 16 | 2640 RU Fs 1 | Genomewalker |
| Ss026-2693 | 5 | 5 | 2693 RU Sn 1 | Genomewalker |
| Ss026-2732 | 6 | 7 | 2732 RU Fs 1 | Genomewalker |
| Ss026-2749 | 5 | 4 | 2749 RUrev468 1-2 | TAIL PCR | bands EP = Number detected by probe of EPSPS gene portion
bands 2OX = Number detected by probe of GA2OX gene portion

TABLE 6

Primer sequences used for flanking sequence identification:

| Primer Set | SEQ. ID. NO. | Primer Name | Primer sequence | NTs | Flanking Sequence |
|---|---|---|---|---|---|
| 1a | 15 | Primer 1: 1819 RU Sn 1 3-1 | GGTCCTTTATAGGGAAA GCATATCATAG | 28 | 1819 ZS Sn 1 |
| 1b | 16 | Primer 2: Sp3 rev | GCAGAGACACAGAGCCT TCATTAACCAAACTTC | 33 | 1819 ZS Sn 1 |
| 2a | 17 | Primer 1: 1984 RU FNS 3-2 | TGGCTGGACAGGGATTT CGTGACT | 24 | 1984 RU FNS |
| 2b | 18 | Primer 2: PRU761 f1-1 | CATAATATCTTCGTCCCA TAGGTGTC | 26 | 1984 RU FNS |
| 3a | 19 | Primer 1: 2006 TAIL GO 1 3-1 | ATCCACATGTGCATCTCG TTATGGCCTGGGT | 31 | 2006 TAIL GO 1 |
| 3b | 20 | Primer 2: PGO761 f1-1 | GCATAGTTCTAGTTATCA GCGCTACATATATAAGG | 35 | 2006 TAIL GO 1 |
| 4a | 21 | Primer 1: 2027 ZS2 3-1 | CTTAGGTGGAAGGCGAA GAAGGCCCCCTT | 29 | 2027 ZS 2 |
| 4b | 16 | Primer 2: Sp3 rev | GCAGAGACACAGAGCCT TCATTAACCAAACTTC | 33 | 2027 ZS 2 |
| 5a | 22 | Primer 1: 2050 TAIL GO 1 3-3 | GTTGACGTGCGTACGAA CAAACGAGTTTCAG | 31 | 2050 TAIL GO 1 |
| 5b | 20 | Primer 2: PGO761 f1-1 | GCATAGTTCTAGTTATCA GCGCTACATATATAAGG | 35 | 2050 TAIL GO 1 |
| 6a | 23 | Primer 1: 2085 GO Sn 1 3-2 | GAGCCGACTCATGCCTA ATGCTTCTCTAG | 29 | 2085 GO Sn 1 |
| 6b | 20 | Primer 2: PGO761 f1-1 | GCATAGTTCTAGTTATCA GCGCTACATATATAAGG | 35 | 2085 GO Sn 1 |
| 7a | 24 | Primer 1: 2085 SZ Sn 1 3-2 | TATTACAGCGCCTTCTAA TAATGTC | 25 | 2085 SZ Sn 1 |
| 7b | 25 | Primer 2: 2085 SZ Sn 1 5-1 | CTCCTTGGCGGCGGTGGC CACGAGCCTGGA | 30 | 2085 SZ Sn 1 |
| 8a | 26 | Primer 1: 2393 GO Sn 1 3-2 | CGGTGCGCCTTCGCCCAC TTTCGGTTAG | 28 | 2393 GO Sn 1 |
| 8b | 20 | Primer 2: PGO761 f1-1 | GCATAGTTCTAGTTATCA GCGCTACATATATAAGG | 35 | 2393 GO Sn 1 |
| 9a | 27 | Primer 1: 2475 TAIL GO 1 3-2 | CTCGCGACATCCGAAAA CTAGAGG | 24 | 2475 TAIL GO1 |
| 9b | 28 | Primer 2: 415 GOB1 5-2 | GAACGTATATTCTAAGC AATAATGATTTC | 29 | 2475 TAIL GO1 |
| 10a | 29 | Primer 1: 2623 GOB1 LAD13 D | ATGCTTCAAGCTGGTCAG ATCCG | 23 | 2623 TAIL GOB1 1-3 |

TABLE 6-continued

Primer sequences used for flanking sequence identification:

| Primer Set | SEQ. ID. NO. | Primer Name | Primer sequence | NTs | Flanking Sequence |
|---|---|---|---|---|---|
| 10b | 30 | Primer 2: 761 EPJ 5-2 | CGGATGTAGATCTGCGA TCCGCCG | 24 | 2623 TAIL GOB1 1-3 |
| 11a | 31 | Primer 1: 2640 RU Fs 1 3-1 | GTATTTTGGACGAGCATA CTGCATAC | 26 | 2640 RU Fs 1 |
| 11b | 18 | Primer 2: PRU761 fl-1 | CATAATATCTTCGTCCCA TAGGTGTC | 35 | 2640 RU Fs 1 |
| 12a | 32 | Primer 1: 2693 RU Sn 1 3-5 | GAAGTACAAACTGTCCA AAAAATAG | 25 | 2693 RU Sn 1 |
| 12b | 33 | Primer 2: PGO2 rev | GTGGTCTGGTGATGGTG GAGTGCTTGAATTCAG | 33 | 2693 RU Sn 1 |
| 13a | 34 | Primer 1: 2732 RU Fs 1 3-2 | CGGCCTGTTTATCTTTGG ACTATG | 24 | 2732 RU Fs 1 |
| 13b | 18 | Primer 2: PRU761 fl-1 | CATAATATCTTCGTCCCA TAGGTGTC | 26 | 2732 RU Fs 1 |
| 14a | 35 | Primer 1: 2749 RU468 1-2 3-3 | TGGAGGAAGAGAAGATA GAGAGAATC | 26 | 2749 RUrev468 1-2 |
| 14b | 18 | Primer 2: PRU761 fl-1 | CATAATATCTTCGTCCCA TAGGTGTC | 26 | 2749 RUrev468 1-2 |

FIG. 6 shows a photograph of an electrophoresis gel showing PCR bands from reactions using primers disclosed herein. The gels shown are from a series of PCR tests on identical sets of 14 genomic DNA samples extracted from St. Augustinegrass cv Floratam, including a non-transgenic control and 13 transgenic events described herein. These PCR reactions differ only in the primers used. One set of primers (A) recognizes and amplifies a 0.7-kb band from a native gene sequence, which should be present in all 14 samples. One set of primers (B) recognizes and amplifies a 0.43-kb fragment within the GA2OX cassette of the transgene, and should be present in all 13 transgenic events and absent in the non-transgenic Floratam. Each of the other PCR tests is using a set of primers which recognizes transgene-junction to native DNA which is unique to one of each event. This test demonstrates the ability of unique transgene junction PCR to identify a specific transgene event and distinguish it from non-transgenic plant material, as well as from other events transformed with the same transgene sequence.

PCR conditions: DNA (approx. 50 ng) was assayed in 25-μL volumes of PCR reaction mix (Promega GoTaq® Flexi DNA Polymerase) containing: 1×PCR buffer, 0.625 units Taq polymerase, 0.2 mM dNTPs, 1.5 mM MgCl2, primers, 0.2 μM each primer.

PCR program: 95° C.-2', 40×(94° C.-18", 60° C.-35", 72° C.-1'45"), 72° C.-10', 10° C.-hold.

DNA samples:
Floratam nontransgenic control
Floratam transgenic line Ss026-1819
Floratam transgenic line Ss026-1984
Floratam transgenic line Ss026-2006
Floratam transgenic line Ss026-2027
Floratam transgenic line Ss026-2050
Floratam transgenic line Ss026-2085
Floratam transgenic line Ss026-2393
Floratam transgenic line Ss026-2475
Floratam transgenic line Ss026-2623
Floratam transgenic line Ss026-2640
Floratam transgenic line Ss026-2693
Floratam transgenic line Ss026-2732
Floratam transgenic line Ss026-2749

Primer sets:
A. Detects a native St Augustinegrass gene, kaurene oxidase (Ral KO 5-1/Ral KO 3-1)
B. Detects all pSCO761 transgenics, primes within GA2OX gene cassette (761DWJ5-2/761 DWJ3-2)
C. Event-specific for Ss026-1819 (1819 RU Sn 1 3-1/Sp3 rev)
D. Event-specific for Ss026-1984 (1984 RU FNS 1 3-2/PRU761 fl-1/)
E. Event-specific for Ss026-2006 (2006 TAIL GO 1 3-1/PGO761 fl-1)
F. Event-specific for Ss026-2027 (2027 ZS2 3-1/Sp3 rev)
G. Event-specific for Ss026-2050 (2050 TAIL GO 1 3-3/PGO761 fl-1)
H. Event-specific for Ss026-2085 (2085 GO Sn 1 3-2/PGO761 fl-1)
I. Event-specific for Ss026-2085 (/2085 SZ Sn 1 3-2/2085 SZ Sn 1 5-1)
J. Event-specific for Ss026-2393 (2393 GO Sn 1 3-2/PGO761 fl-1)
K. Event-specific for Ss026-2475 (2475 TAIL GO 1 3-2/415 GOBI 5-2)
L. Event-specific for Ss026-2623 (2623 GOBI LAD1-3 D/761 EPJ 5-2)
M. Event-specific for Ss026-2640 (2640 RU Fs 1 3-1/PRU761 fl-1)
N. Event-specific for Ss026-2693 (2693 RU Sn 1 3-5/PGO2 rev)

O. Event-specific for Ss026-2732 (2732 RU Fs 1 3-2/ PRU761 fl-1)
P. Event-specific for Ss026-2749 (2749 RU468 1-2 3-3/ PRU761 fl-1)

Example 18

Selecting for Plants Exhibiting Glyphosate Tolerance and/or Enhanced Turfgrass Qualities Transgenic St. Augustinegrass comprising event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 or Ss026-2749 can be tested for tolerance to glyphosate vegetative injury. St. Augustinegrass plants comprising events Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 and Ss026-2749 show no damage to Roundup® Pro (glyphosate containing herbicide formulation) sprayed in a booth at 3.0 lbs acid equivalence or an amount equivalent to 128 ounces Roundup® Pro per acre. The standard recommended rate is 1.25 to 2.5% Roundup® Pro or amount equivalent to 32 to 64 ounces Roundup® Pro per acre. Therefore, treating a turfgrass stand comprising St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 or Ss026-2749 with a glyphosate-containing herbicide is useful for controlling weeds and other unwanted plants in the turfgrass stand.

Transgenic St. Augustinegrass comprising event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 or Ss026-2749 can also be tested for enhanced turfgrass qualities, such as reduced vertical growth, which confers various advantages on St. Augustingrass, including denser growth. St. Augustinegrass plants comprising event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 or Ss026-2749 exhibit more compact, denser growth as compared to the Floratam cultivar of St. Augustinegrass. Therefore, planting a turfgrass stand comprising St. Augustinegrass event Ss026-1819, Ss026-1984, Ss026-2006, Ss026-2027, Ss026-2050, Ss026-2085, Ss026-2393, Ss026-2475, Ss026-2623, Ss026-2640, Ss026-2693, Ss026-2732 or Ss026-2749 is useful for enhancing the turfgrass qualities of the resulting turfgrass stand.

The invention claimed is:

1. A transgenic plant, plant tissue, or plant part thereof, comprising the following nucleic acid molecules:
   a nucleic acid sequence with at least 95% sequence identity to SEQ ID NO: 37;
   a nucleic acid sequence with at least 95% sequence identity to SEQ ID NO: 39; and
   SEQ ID NO: 3, SEQ ID NO: 4, SEQ ID NO: 5, SEQ ID NO: 8, SEQ ID NO: 9, SEQ ID NO: 11, or SEQ ID NO: 13.

2. The plant or plant part thereof of claim 1, wherein the part is a cell, tuber, crown, stem, tiller, cuttings including un-rooted cuttings, rooted cuttings, and callus cuttings or callus-generated plantlets; apical meristems, pollen, ovule, flower, shoot, stolon, propagule, seed, runner, corm, rhizome, root, or leaf.

3. The plant or plant part thereof of claim 2, wherein the plant is turfgrass.

4. The plant or plant part thereof of claim 3, wherein the turfgrass is St. Augustine grass.

5. The plant or plant part thereof of claim 3, wherein the turfgrass possesses desirable characteristics of: glyphosate tolerance, shorter growth habit, darker green color, and/or fuller stand.

6. A transgenic plant cell comprising the nucleic acid of claim 1, which is operably linked to regulatory elements allowing transcription and/or expression of the nucleic acid sequence in plant cells.

7. The transgenic plant cell of claim 6, wherein said nucleic acid sequence or a vector comprising said nucleic acid sequence is stably integrated into the genome of the plant cell.

8. A transgenic plant, plant tissue, or plant part comprising plant cells of claim 7.

9. The progeny derived from any of the plants, plant tissues, or plant parts of claim 8, wherein the progeny comprises the following nucleic acid molecules:
   a nucleic acid sequence with at least 95% sequence identity to SEQ ID NO: 37;
   a nucleic acid sequence with at least 95% sequence identity to SEQ ID NO: 39; and
   SEQ ID NO: 3, SEQ ID NO: 4, SEQ ID NO: 5, SEQ ID NO: 8, SEQ ID NO: 9, SEQ ID NO: 11, or SEQ ID NO: 13.

10. A St. Augustine grass plant or part thereof comprising the following nucleic acid molecules:
    a nucleic acid sequence with at least 98% sequence identity to SEQ ID NO: 37;

a nucleic acid sequence with at least 98% sequence identity to SEQ ID NO: 39; and SEQ ID NO: 3, SEQ ID NO: 4, SEQ ID NO: 5, SEQ ID NO: 8, SEQ ID NO: 9, SEQ ID NO: 11, or SEQ ID NO: 13.

11. A turfgrass stand, lawn, sports field, or golf course comprising a St. Augustine grass plant comprising the following nucleic acid molecules:

a nucleic acid sequence with at least 95% sequence identity to SEQ ID NO: 37;

a nucleic acid sequence with at least 95% sequence identity to SEQ ID NO: 39; and SEQ ID NO: 3, SEQ ID NO: 4, SEQ ID NO: 5, SEQ ID NO: 8, SEQ ID NO: 9, SEQ ID NO: 11, or SEQ ID NO: 13.

12. The transgenic propagule of claim 2, that comprises in its genome a recombinant DNA molecule that expresses a nucleotide sequence that encodes an EPSPS enzyme that confers glyphosate resistance to a plant and a recombinant DNA molecule that expresses a nucleotide sequence that encodes GA2OX enzyme that confers enhanced turfgrass quality in grasses.

13. A method of vegetatively propagating a plant comprising the steps of: (a) collecting tissue capable of being propagated from the plant according to claim 10; (b) cultivating the tissue to obtain proliferated shoots; and (c) rooting the proliferated shoots to obtain rooted plantlets.

14. The method of claim 13, further comprising growing at least a first plant from the rooted plantlets.

15. A method for controlling weeds in a field comprising growing the plant or part thereof of claim 2, and treating the field with an effective amount of an herbicide comprising glyphosate.

16. A method for controlling weeds in a field comprising growing the plant or part thereof of claim 10, and treating the field with an effective amount of an herbicide comprising glyphosate.

17. The transgenic plant, plant tissue, or plant part thereof, of claim 1, comprising the following nucleic acid molecules:

a nucleic acid sequence of SEQ ID NO: 37;

a nucleic acid sequence of SEQ ID NO: 39; and

SEQ ID NO: 3, SEQ ID NO: 4, SEQ ID NO: 5, SEQ ID NO: 8, SEQ ID NO: 9, SEQ ID NO: 11, or SEQ ID NO: 13.

18. The St. Augustine grass plant or part thereof of claim 10, comprising the following nucleic acid molecules:

a nucleic acid sequence of SEQ ID NO: 37;

a nucleic acid sequence of SEQ ID NO: 39; and

SEQ ID NO: 3, SEQ ID NO: 4, SEQ ID NO: 5, SEQ ID NO: 8, SEQ ID NO: 9, SEQ ID NO: 11, or SEQ ID NO: 13.

19. The turfgrass stand, lawn, sports field, or golf course of claim 11, wherein the St. Augustine grass plant comprises the following nucleic acid molecules:

a nucleic acid sequence of SEQ ID NO: 37;

a nucleic acid sequence of SEQ ID NO: 39; and

SEQ ID NO: 3, SEQ ID NO: 4, SEQ ID NO: 5, SEQ ID NO: 8, SEQ ID NO: 9, SEQ ID NO: 11, or SEQ ID NO: 13.

* * * * *